(12) United States Patent
Liu et al.

(10) Patent No.: US 8,937,072 B2
(45) Date of Patent: Jan. 20, 2015

(54) SUBSTITUTED CYANOANILINE COMPOUNDS, PREPARATION AND USE THEREOF

(75) Inventors: Changling Liu, Shenyang (CN); Guang Huang, Shenyang (CN); Jie Lan, Shenyang (CN); Shulin Hao, Shenyang (CN); Zhinian Li, Shenyang (CN); Huichao Li, Shenyang (CN); Aiying Guan, Shenyang (CN); Airu Jiang, Shenyang (CN); Ying Xu, Shenyang (CN)

(73) Assignees: Sinochem Corporation, Beijing (CN); Shenyang Research Institute of Chemical Industry Co., Ltd., Shenyang, Liaoning (CN)

( * ) Notice: Subject to any disclaimer, the term of this patent is extended or adjusted under 35 U.S.C. 154(b) by 0 days.

(21) Appl. No.: 14/118,509

(22) PCT Filed: Jun. 15, 2012

(86) PCT No.: PCT/CN2012/077011
§ 371 (c)(1),
(2), (4) Date: Nov. 18, 2013

(87) PCT Pub. No.: WO2012/171484
PCT Pub. Date: Dec. 20, 2012

(65) Prior Publication Data
US 2014/0213598 A1   Jul. 31, 2014

(30) Foreign Application Priority Data

Jun. 17, 2011 (CN) ............ 2011 1 0163314
Jun. 17, 2011 (CN) ............ 2011 1 0163457
Jun. 17, 2011 (CN) ............ 2011 1 0163460
Jun. 17, 2011 (CN) ............ 2011 1 0163496

(51) Int. Cl.

| | | |
|---|---|---|
| A61K 31/495 | (2006.01) | |
| C07D 237/12 | (2006.01) | |
| A01N 37/34 | (2006.01) | |
| A01N 59/04 | (2006.01) | |
| C07D 213/74 | (2006.01) | |
| C07C 255/58 | (2006.01) | |
| C07D 237/24 | (2006.01) | |
| C07D 239/52 | (2006.01) | |
| C07D 241/26 | (2006.01) | |
| C07C 255/59 | (2006.01) | |
| C07C 255/60 | (2006.01) | |
| A01N 37/44 | (2006.01) | |
| A01N 43/40 | (2006.01) | |
| A01N 43/54 | (2006.01) | |
| A01N 43/58 | (2006.01) | |
| A01N 43/60 | (2006.01) | |

(52) U.S. Cl.
CPC ............ *A01N 37/34* (2013.01); *A01N 59/04* (2013.01); *C07D 213/74* (2013.01); *C07C 255/58* (2013.01); *C07D 237/24* (2013.01); *C07D 239/52* (2013.01); *C07D 241/26* (2013.01); *C07C 255/59* (2013.01); *C07C 255/60* (2013.01); *A01N 37/44* (2013.01); *A01N 43/40* (2013.01); *A01N 43/54* (2013.01); *A01N 43/58* (2013.01); *A01N 43/60* (2013.01)
USPC ........................ 514/255.06; 544/224

(58) Field of Classification Search
CPC ...................................... C07D 237/24
USPC ............... 514/241, 255.06; 544/180, 224
See application file for complete search history.

(56) References Cited

U.S. PATENT DOCUMENTS 3,926,611 A   12/1975  Tomlin et al.
4,614,742 A    9/1986  Ishikawa et al.

FOREIGN PATENT DOCUMENTS

| CN | 101391981 A | 3/2009 |
| GB | 1383306 A | 2/1975 |
| JP | 10-182995 A | 7/1998 |
| JP | 2000169743 | 12/2001 |
| WO | 2012/171484 A1 | 12/2012 |

OTHER PUBLICATIONS

International Search Report for Application No. PCT/CN2012/77011 mailed on Aug. 2, 2012 (In English).

*Primary Examiner* — Taofiq A Solola
(74) *Attorney, Agent, or Firm* — Smith, Gambrell & Russell, LLP

(57) ABSTRACT

Disclosed is a substituted cyanoaniline compound or a salt thereof, wherein the compound has a structure represented by General Formula I. The compound of General Formula I has broad-spectrum fungicidal activity in the field of agriculture and effectively prevents against a variety of pathogens such as cucumber downy mildew, wheat powdery mildew, maize rust disease, rice blast and cucumber gray mold. In particular, even at a low dose, the compound effectively prevents and treats rice blast, cucumber gray mold, maize rust disease and cucumber downy mildew. Moreover, the raw materials for preparing the compounds are widely available and the synthesis method therefor is simple and convenient.

12 Claims, No Drawings

SUBSTITUTED CYANOANILINE COMPOUNDS, PREPARATION AND USE THEREOF

FIELD OF THE INVENTION

The present invention relates to fungicide. Specifically to a kind of substituted cyanoaniline compounds, preparation and use thereof.

BACKGROUND OF THE INVENTION

Diphenylamine and fluazinam are known fungicides, the former is mainly used to control storage diseases of fruits and vegetables, and the latter is mainly used to control diseases of field crops.

Patent CN101391981A disclosed the compounds having the following general formulas as intermediates to synthesize new polyhaloacridone compounds having fluorescene activities and potential pharmaceutical activity, in this patent, compound IV-A (KC1), compound IV-B (KC2), compound IV-D (KC3), compound IV-E (KC4), compound IV-H (KC5), compound IV-C (KC6), IV-O (KC7), IV-P (KC8), IV-Q (KC9), IV-R (KC 10), IV-U (KC11) were reported without any bio-activity data; U.S. Pat. No. 4,614,742 A disclosed compound 6 (KC7), 7 (KC8) and 8 (KC12), showing bacteriostatic diameter of 22.5 mm, 10.2 mm, 15.5 mm and 13.8 mm, 0 mm, 0 mm against blast of rice and canker of citrus fruit respectively at 500 ppm, compounds 6 and 7 exhibited 100% and 90% respectively control against pear scab; JP 2000169743 A reported the production process of Phthalocyanine compounds, in which compound KC 13 was mentioned.

Pesticide Science (1988), 24(2), 111-21 reported compounds XXIX (KC1), XXX (KC 14), XXXI (KC15) had some activity on relevant diseases at high dose such as plasmopora viticola; Journal of Medicinal Chemistry (1978), 21(9), 906-13 disclosed compound 28g (KC16) with some anti-inflammatory activity.

KC1

![KC1 structure]

KC2

![KC2 structure]

KC3

![KC3 structure]

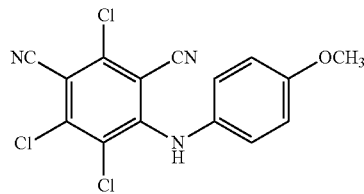

KC4

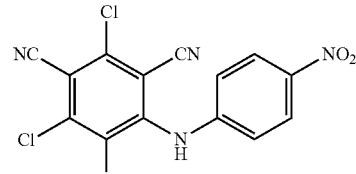

KC5

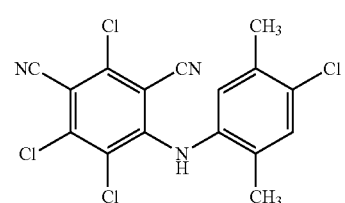

KC6

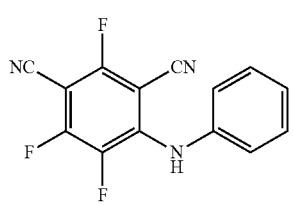

KC7

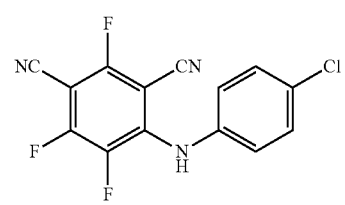

KC8

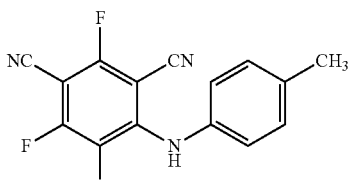

KC9

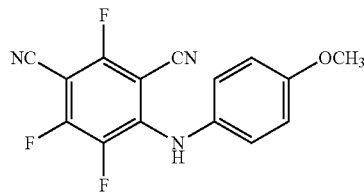

KC10

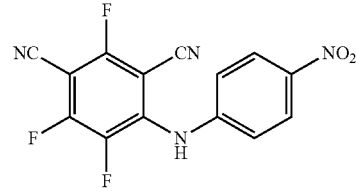

KC11

-continued

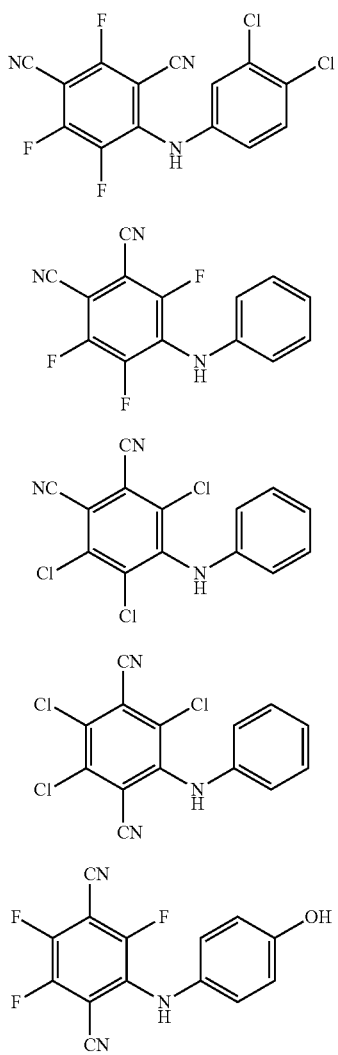

KC12

KC13

KC14

KC15

KC16

CN101391981A also disclosed the following compounds IV-I (KC17), IV-J (KC18), IV-K (KC19), IV-L (KC20) as intermediates to synthesize new polyhaloacridone compounds having fluorescene activities and potential pharmaceutical activity, but there was no any bioactivity reported.

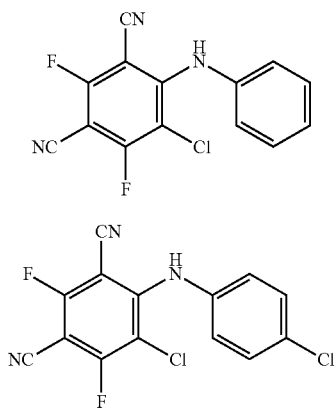

KC17

KC18

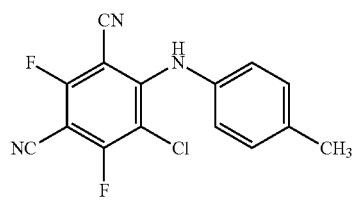

KC19

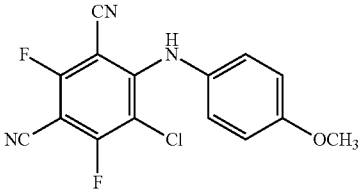

KC20

Substituted cyanoaniline compounds disclosed in the prior art, in which the substituents on the right phenyl ring are mostly single substituent, however, substituted cyanoaniline compounds having general formula of the present invention, its right phenyl ring are double or multiple substituted phenyl group, or other nitrogen-containing 6-member heterocycle, were not reported.

SUMMARY OF THE INVENTION

New pesticides with novel structure and excellent property are needed by modern agricultural production. The object of the present invention is to provide a kind of substituted cyanoaniline compounds to control a variety of plant pathogens/diseases at very low doses, which can be used to prepare substances to control pathogens in agriculture and other field.

Detailed description of the invention is as follows:

The present invention provides a kind of substituted cyanoaniline compounds having general formula I:

$$A-\underset{\underset{R_1}{|}}{N}-Q \qquad 1$$

wherein:

$R_1$ is selected from H, $C_1$-$C_4$alkyl, $C_1$-$C_4$alkylcarbonyl, $C_1$-$C_4$alkylsulfonyl, benzyl or phenethyl;

A is selected from $A_1$, $A_2$ or $A_3$

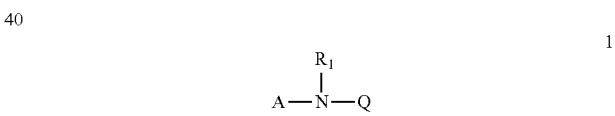

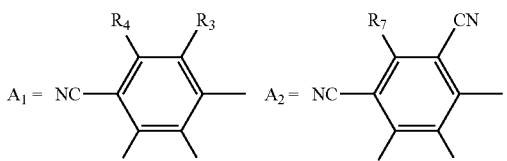

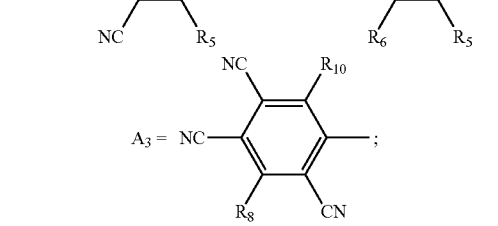

$R_2$, $R_3$, $R_4$, $R_5$, $R_6$, $R_7$, $R_8$, $R_9$, $R_{10}$ mutually independently may be the same or different, selected from halo, $C_1$-$C_8$ alkoxy, $C_1$-$C_8$haloalkoxy, $NR_{12}R_{13}$, $C_1$-$C_8$alkylthio, $C_1$-$C_8$haloalkylthio, $C_1$-$C_8$ alkylsulfinyl, $C_1$-$C_8$ haloalkylsulfinyl, $C_1$-$C_8$ alkylsulfonyl, $C_1$-$C_8$haloalkylsulfonyl, $C_3$-$C_8$ alkenyloxy, $C_3$-$C_8$haloalkenyloxy, $C_3$-$C_8$alkynyloxy, $C_3$-$C_8$haloalkynyloxy, $C_1$-$C_8$alkylcarbonyloxy, $C_1$-$C_8$alkylcarbonylamino, $C_1$-$C_8$alkylsulfonyloxy, $C_1$-$C_8$alkoxy$C_1$-$C_8$alkoxy or $C_1$-$C_8$ alkoxycarbonyl$C_1$-$C_8$alkoxy;

Q is selected from phenyl, pyridinyl, pyrimidinyl, pyridazinyl, pyrazinyl, sym-triazinyl or unsym-triazinyl, which is mutually independently optionally substituted by $(R_{11})n$, $R_{11}$ is selected from halo, $NO_2$, CN, $C_1$-$C_8$alkyl, $C_1$-$C_8$haloalkyl, $C_3$-$C_6$cycloalkyl, $C_1$-$C_8$ alkoxy, $C_1$-$C_8$haloalkoxy, $C_1$-$C_8$ alkylthio, $C_1$-$C_8$ haloalkylthio, $C_2$-$C_8$alkenyl, $C_2$-$C_8$haloalkenyl, $C_2$-$C_8$alkynyl, $C_2$-$C_8$ haloalkynyl, $C_3$-$C_8$alkenyloxy, $C_3$-$C_8$haloalkenyloxy, $C_3$-$C_8$alkynyloxy, $C_3$-$C_8$haloalkynyloxy, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$ haloalkylcarbonyl, $C_1$-$C_8$alkylcarbonyloxy, $C_1$-$C_8$ alkylcarbonylamino, $C_1$-$C_8$alkylsulfonyloxy, $C_1$-$C_8$alkoxycarbonyl, $C_1$-$C_8$alkoxycarbonyl$C_1$-$C_8$alkyl, $C_1$-$C_8$ alkoxycarbonylamino, $C_1$-$C_9$alkoxy$C_1$-$C_8$alkoxy, $C_1$-$C_8$alkoxycarbonyl$C_1$-$C_8$alkoxy, phenylaminocarbonyl, halophenylaminocarbonyl, CHO, $CO_2H$, $CO_2Na$, $CO_2NH_4$, $C(=O)NR_{12}R_{13}$, $OC(=O)NR_{12}R_{13}$, $C(=S)NR_{12}R_{13}$ or $SO_2NR_{12}R_{13}$; n=0-5;

$R_{12}$, $R_{13}$ mutually independently may be the same or different, selected from H, $C_1$-$C_6$ alkyl, $C_1$-$C_6$haloalkyl or $C_3$-$C_6$ cycloalkyl;

But when Q is phenyl, n≠0 or 1; at the same time, the following compounds are excluded:

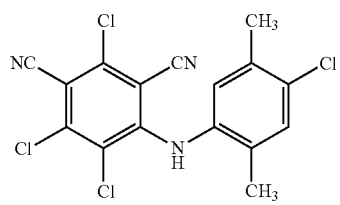

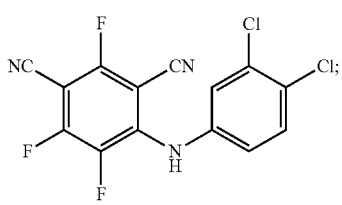

Or the salts formed from the compounds of general formula I.

The preferred compounds of general formula I of this invention are:

$R_1$ is H;

A is $A_1$, wherein $R_2$, $R_3$ and $R_4$ are Cl;

Q is phenyl, which is mutually independently optionally substituted by $(R_{11})n$, $R_{11}$ is selected from halo, $NO_2$, CN, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl or $C(=O)NHCH_3$; n=2-4; the structure is represented by general formula I-1:

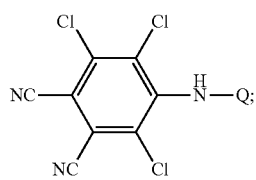

Or, in general formula I $R_1$ is H;

A is $A_2$, wherein $R_5$, $R_6$ and $R_7$ are same, selected from F or Cl;

Q is selected from phenyl, pyridin-2-yl, pyridin-3-yl, pyridin-4-yl, pyrimidin-2-yl, pyrazin-2-yl or pyridazin-3-yl, which is mutually independently optionally substituted by $(R_{11})n$, $R_{11}$ is selected from halo, $NO_2$, CN, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl, $C(=O)NHCH_3$, phenylaminocarbonyl, 4-Clphenylaminocarbonyl, $CO_2H$ or $CO_2Na$; n=0-5; but when Q is phenyl, n≠0 or 1; at the same time, the following compounds are excluded:

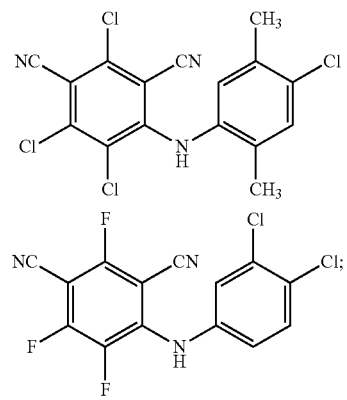

The structure is represented by general formula I-2:

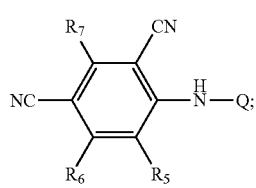

Or, in general formula I $R_1$ is H;

A is $A_3$, wherein $R_8$, $R_9$ and $R_{10}$ are same, selected from F or Cl;

Q is selected from phenyl, pyridin-2-yl, pyridin-3-yl, pyridin-4-yl or pyrimidin-2-yl, which is mutually independently optionally substituted by $(R_{11})n$, $R_{11}$ is selected from halo, $NO_2$, CN, $C_1$-$C_4$alkyl, $C_1$-$C_4$haloalkyl, $C_1$-$C_4$alkoxy, $C_1$-$C_4$ haloalkoxy, $C_1$-$C_4$alkoxycarbonyl or $C(=O)NHCH_3$; n=2-4;

The structure is represented by general formula I-3:

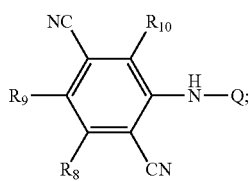

Or the salts formed from the compounds of general formula I-1, I-2 or I-3 with hydrochloric acid, sulfuric acid, phosphoric acid, trifluoroacetic acid, methylsulfonic acid, acetic acid, p-toluenesulfonic acid, sodium or potassium.

Further more, the preferred compounds of general formula I-1 of this invention are:

Q is selected from phenyl, which is mutually independently optionally substituted by $(R_{11})n$, $R_{11}$ is selected from F, Cl, Br, $NO_2$, CN, methyl, isopropyl, tert-butyl, trifluoromethyl, methoxyl, trifluoromethoxyl, methoxycarbonyl or $C(=O)NHCH_3$; n=2-4;

Or, in general formula I-2
$R_5$, $R_6$ and $R_7$ are same, selected from F or Cl;
Q is selected from phenyl, pyridin-2-yl, pyridin-3-yl, pyridin-4-yl, pyrimidin-2-yl, pyrazin-2-yl or pyridazin-3-yl, which is mutually independently optionally substituted by $(R_{11})n$, $R_{11}$ is selected from F, Cl, Br, $NO_2$, CN, methyl, ethyl, isopropyl, tert-butyl, trifluoromethyl, methoxyl, trifluoromethoxyl, methoxycarbonyl, ethoxycarbonyl, $C(=O)NHCH_3$, phenylaminocarbonyl, 4-Clphenylaminocarbonyl, $CO_2H$ or $CO_2Na$; n=0-5; but when Q is phenyl, n≠0 or 1; at the same time, the following compounds are excluded:

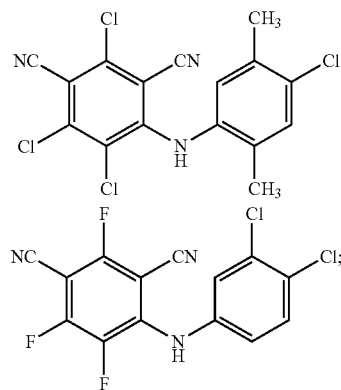

Or, in general formula I-3
$R_8$, $R_9$ and $R_{10}$ are same, selected from F or Cl;
Q is selected from phenyl, pyridin-2-yl, pyridin-3-yl, pyridin-4-yl or pyrimidin-2-yl, which is mutually independently optionally substituted by $(R_{11})n$, $R_{11}$ is selected from F, Cl, Br, $NO_2$, CN, methyl, isopropyl, trifluoromethyl, methoxyl, trifluoromethoxyl, methoxycarbonyl, ethoxycarbonyl or $C(=O)NHCH_3$; n=2-4;

Or the salts formed from the compounds of general formula I-1, I-2 or I-3 with hydrochloric acid, sulfuric acid, phosphoric acid, trifluoroacetic acid, methylsulfonic acid, acetic acid, p-toluenesulfonic acid, sodium or potassium.

Most preferred compounds of formula I-1 of this invention are:

Q is selected from 2-F-4-$NO_2$phenyl, 2-Cl-4-$NO_2$phenyl, 2-Cl-5-$NO_2$phenyl, 2-Cl-4-$CF_3$phenyl, 2-Cl-5-$CF_3$phenyl, 2,4-2$NO_2$phenyl, 3-$CF_3$-4-Clphenyl, 2,4-2Clphenyl, 2-Cl-4-Brphenyl, 2-Br-4-Clphenyl, 2,6-2Clphenyl, 3-$CF_3$-4-Clphenyl, 2,3,4-3Fphenyl, 2-Br-6-CN-4-$NO_2$phenyl, 2,6-2F-4-$NO_2$phenyl, 2,6-2Cl-4-$NO_2$phenyl, 2,6-2Br-4-$NO_2$phenyl, 2-Br-6-Cl-4-$NO_2$phenyl or 2-$CH_3$-3-Cl-4,6-2$NO_2$phenyl;

Or, in general formula I-2
When $R_5$, $R_6$ and $R_7$ are F, Q is selected from 2-Cl-4-$CF_3$phenyl, 2-Cl-4-$NO_2$phenyl, 2,4-2Clphenyl, 2-Cl-4-Brphenyl, 2-Br-4-Clphenyl, 2,6-2Clphenyl, 2,6-2Br-4-$NO_2$phenyl, 2,6-2Cl-4-$NO_2$phenyl, 2,6-2Cl-4-$CF_3$phenyl or 2-Br-6-CN-4-$NO_2$phenyl;

When $R_5$, $R_6$ and $R_7$ are Cl, Q is selected from 2,6-2Fphenyl, 2-Cl-4-$CF_3$phenyl, 2-Cl-5-$CF_3$phenyl, 2-F-5-$CF_3$phenyl, 2-Cl-4-$NO_2$phenyl, 2-$NO_2$-4-Clphenyl, 2,4-2Clphenyl, 2-Cl-4-Brphenyl, 2-Br-4-Clphenyl, 2,6-2Clphenyl, 2,4,6-3Clphenyl, 2,3,4-3Fphenyl, 2,4-2$NO_2$phenyl, 3-$CF_3$-4-CNphenyl, 2,6-2F-4-$NO_2$phenyl, 2,4-2Cl-6-CNphenyl, 2,6-2Cl-4-CNphenyl, 2,6-2Cl-4-$CF_3$phenyl, 2-Cl-6-F-4-$NO_2$phenyl, 2,6-2Cl-4-$NO_2$phenyl, 2-Br-6-Cl-4-$NO_2$phenyl, 2-Br-6-CN-4-$NO_2$phenyl, 2,6-2Br-4-$NO_2$phenyl, 2,6-2Cl-4-$COOCH_3$phenyl, 2-$CH_3$-6-Cl-4-$NO_2$phenyl, 2-$CH_3$-4-Cl-6-$NO_2$phenyl, 2,6-2$NO_2$-3-Cl-4-$CF_3$phenyl, 2-$CH_3$-3-Cl-4,6-2$NO_2$phenyl, 2,3,5-3Cl-4,6-2CNphenyl, 5-Br-pyridin-2-yl, 3-Cl-5-$CF_3$-pyridin-2-yl, 3,5,6-3Cl-pyridin-2-yl, 3,4,5,6-4Cl-pyridin-2-yl, 2-Cl-pyridin-3-yl, 6-Br-pyridin-3-yl, 2,5-2Cl-pyridin-3-yl, 2-Cl-pyridin-4-yl, 3-Br-pyridin-4-yl, 3,5-2Cl-pyridin-4-yl, pyrimidin-2-yl, 4,6-2$OCH_3$pyrimidin-2-yl, 4-$CF_3$-5-$C_2H_5OCO$pyrimidin-2-yl, 6-Cl-pyrazin-2-yl or 6-Cl-pyridazin-3-yl;

Or, in general formula I-3
When $R_8$, $R_9$ and $R_{10}$ are F, Q is selected from 2,4-2Clphenyl, 2-Cl-4-Brphenyl, 2-Br-4-Clphenyl, 2,6-2Clphenyl, 2-F-4-$NO_2$phenyl, 2-Cl-4-$NO_2$phenyl, 2-Cl-5-$NO_2$phenyl, 2-Cl-4-$CF_3$phenyl, 2-$OCH_3$-4-$NO_2$phenyl, 2-$NO_2$-4-Clphenyl, 3-$CF_3$-4-Clphenyl, 2,6-2Cl-4-$NO_2$phenyl, 2,6-2Br-4-$NO_2$phenyl, 2,6-2Cl-4-$CF_3$phenyl, 2-Br-6-CN-4-$NO_2$phenyl, 2-Br-6-Cl-4-$NO_2$phenyl or 3,5-2Cl-pyridin-4-yl;

When $R_8$, $R_9$ and $R_{10}$ are Cl, Q is selected from 2,4-2Clphenyl, 2-Cl-4-Brphenyl, 2-Br-4-Clphenyl, 2,6-2Clphenyl, 2,4-2$NO_2$phenyl, 2-Cl-4-$NO_2$phenyl, 2-Cl-5-$NO_2$phenyl, 2-$NO_2$-4-Clphenyl, 2-$OCH_3$-4-$NO_2$phenyl, 3-$CF_3$-4-Clphenyl, 2-F-4-$NO_2$phenyl, 2-Cl-4-$CF_3$phenyl, 2-Cl-5-$CF_3$phenyl, 3-$CF_3$-4-CNphenyl, 2,6-2Cl-4-$NO_2$phenyl, 2,6-2Br-4-$NO_2$phenyl, 2,6-2F-4-$NO_2$phenyl, 2-Cl-6-F-4-$NO_2$phenyl, 2-Br-6-Cl-4-$NO_2$phenyl, 2,6-2Cl-4-$CF_3$phenyl, 2-Br-6-CN-4-$NO_2$phenyl, 2-$CH_3$-3-Cl-4,6-2$NO_2$phenyl, 2,5-2Cl-pyridin-3-yl, 3,5-2Cl-pyridin-4-yl or pyrimidin-2-yl;

Or the salts formed from the compounds of general formula I-1, I-2 or I-3 with hydrochloric acid, sulfuric acid, phosphoric acid, trifluoroacetic acid, methylsulfonic acid, acetic acid, p-toluenesulfonic acid, sodium or potassium.

Even more preferred compounds of formula I-1 of this invention are:

Q is selected from 2-F-4-$NO_2$phenyl, 2-Cl-4-$NO_2$phenyl, 2-Cl-5-$NO_2$phenyl, 2-Cl-4-$CF_3$phenyl, 2,4-2Clphenyl, 2-Cl-4-Brphenyl, 2-Br-4-Clphenyl, 2,6-2Clphenyl, 2-Br-6-CN-4-$NO_2$phenyl, 2,6-2F-4-$NO_2$phenyl, 2,6-2Cl-4-$NO_2$phenyl, 2,6-2Br-4-$NO_2$phenyl or 2-Br-6-Cl-4-$NO_2$phenyl; namely, the compounds having the following structures:

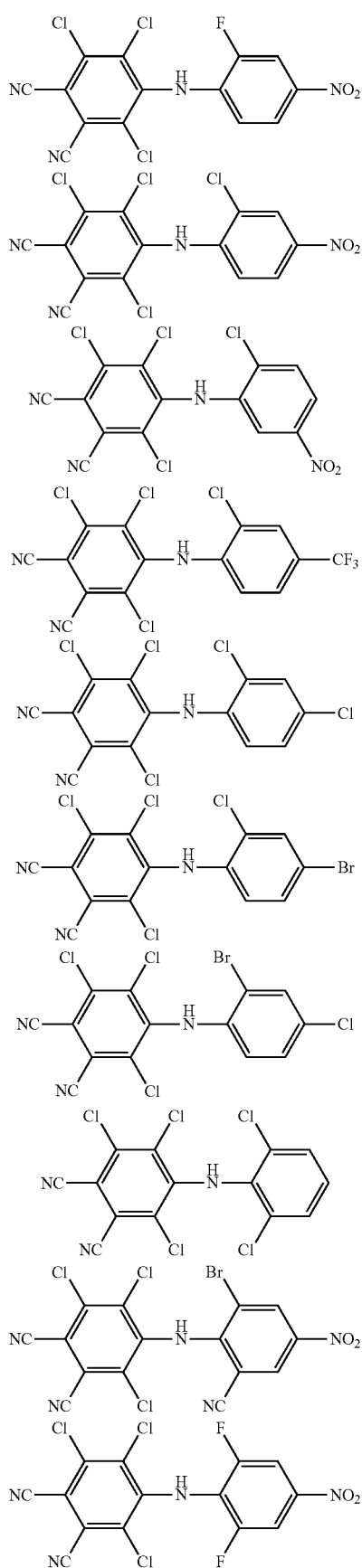

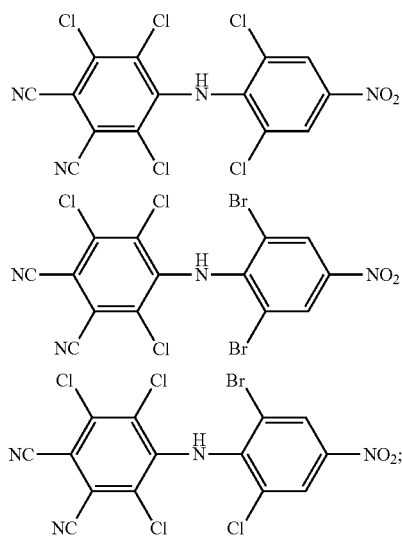

Or, in general formula I-2

When $R_5$, $R_6$ and $R_7$ are F, Q is selected from 2-Cl-4-CF₃phenyl, 2,4-2Clphenyl, 2-Cl-4-Brphenyl, 2-Br-4-Clphenyl, 2,6-2Clphenyl or 2,6-2Br-4-NO₂phenyl;

When $R_5$, $R_6$ and $R_7$ are Cl, Q is selected from 2-Cl-4-CF₃phenyl, 2-Cl-5-CF₃phenyl, 2-F-5-CF₃phenyl, 2-Cl-4-NO₂phenyl, 2,4-2NO₂phenyl, 2-NO₂-4-Clphenyl, 2,4-2Clphenyl, 2-Cl-4-Brphenyl, 2-Br-4-Clphenyl, 2,6-2Clphenyl, 2,3,4-3Fphenyl, 2,4,6-3Clphenyl, 2,6-2F-4-NO₂phenyl, 2,4-2Cl-6-CNphenyl, 2,6-2Cl-4-CNphenyl, 2,6-2Cl-4-CF₃phenyl, 2,6-2Cl-4-COOCH₃phenyl, 2-Cl-6-F-4-NO₂phenyl, 2,6-2Cl-4-NO₂phenyl, 2-Br-6-Cl-4-NO₂phenyl, 2-Br-6-CN-4-NO₂phenyl, 2,6-2Br-4-NO₂phenyl, 2-CH₃-6-Cl-4-NO₂phenyl, 2-CH₃-3-Cl-4,6-2NO₂phenyl, 2,3,5-3Cl-4,6-2CNphenyl, 3-Cl-5-CF₃-pyridin-2-yl, 3,5,6-3Cl-pyridin-2-yl, 3,4,5,6-4Cl-pyridin-2-yl, 2,5-2Cl-pyridin-3-yl, 3,5-2Cl-pyridin-4-yl, 6-Cl-pyrazin-2-yl or 6-Cl-pyridazin-3-yl; namely, the compounds having the following structures:

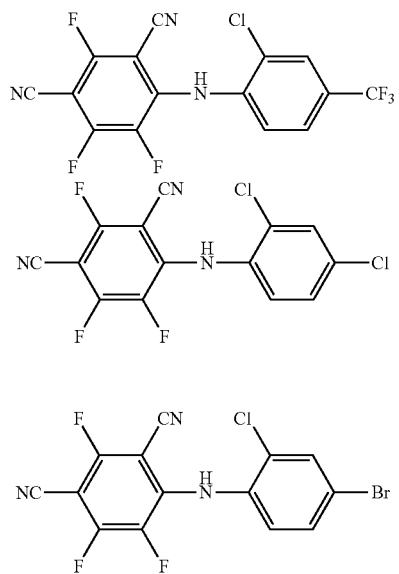

-continued
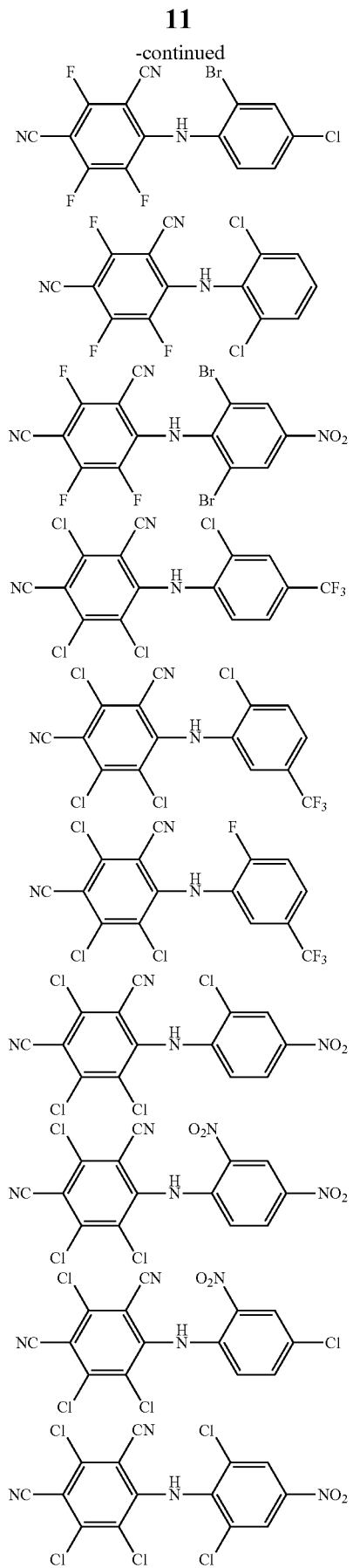
-continued
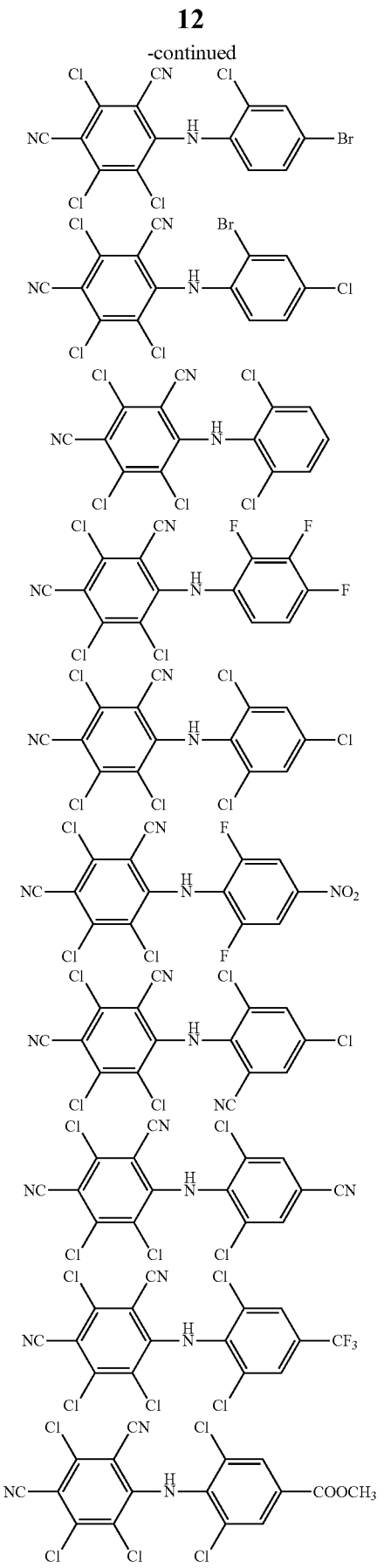

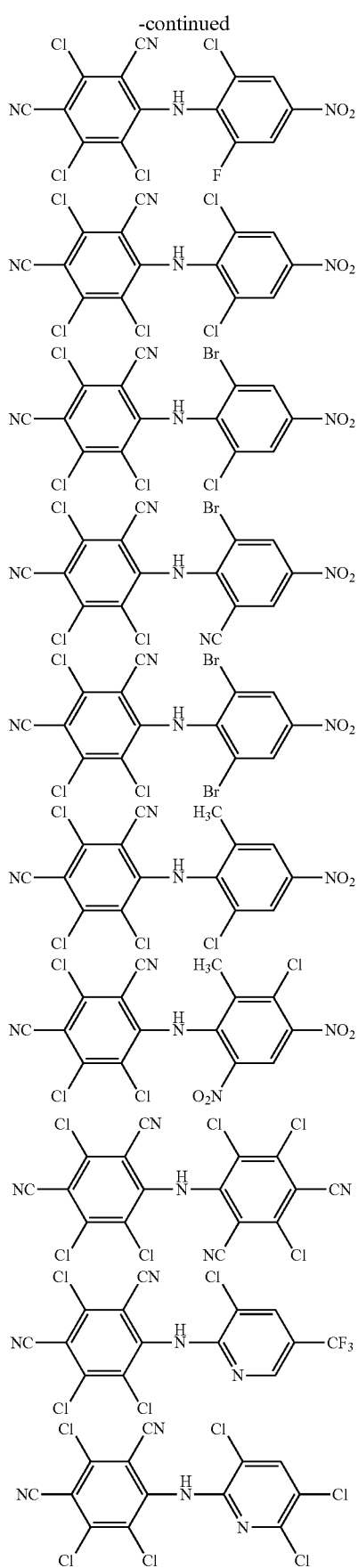

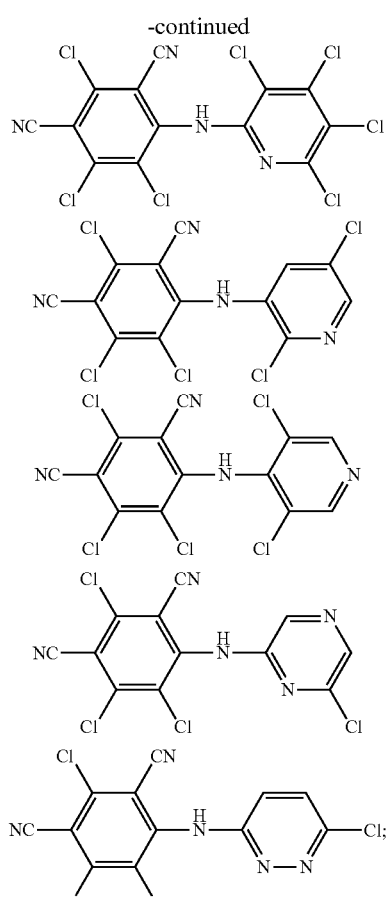

Or, in general formula I-3,

When $R_8$, $R_9$ and $R_{10}$ are F, Q is selected from 2,4-2Clphenyl, 2-Cl-4-Brphenyl, 2-Br-4-Clphenyl, 2,6-2Clphenyl, 2-Br-6-CN-4-NO$_2$phenyl or 2-Br-6-Cl-4-NO$_2$phenyl;

When $R_8$, $R_9$ and $R_{10}$ are Cl, Q is selected from 2-F-4-NO$_2$phenyl, 2-Cl-4-CF$_3$phenyl, 2,4-2Clphenyl, 2-Cl-4-Brphenyl, 2-Br-4-Clphenyl, 2,6-2Clphenyl, 2,6-2Cl-4-NO$_2$phenyl, 2,6-2Br-4-NO$_2$phenyl, 2,6-2F-4-NO$_2$phenyl, 2-Cl-6-F-4-NO$_2$phenyl, 2-Br-6-Cl-4-NO$_2$phenyl, 2,6-2Cl-4-CF$_3$phenyl, 2,5-2Cl-pyridin-3-yl or 3,5-2Cl-pyridin-4-yl; namely, the compounds having the following structures:

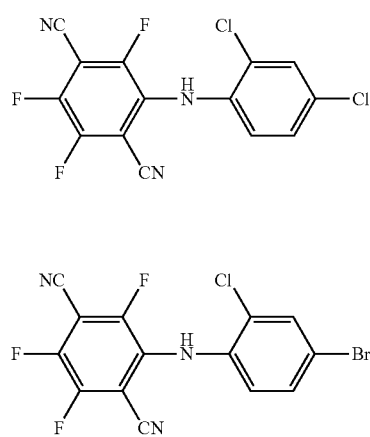

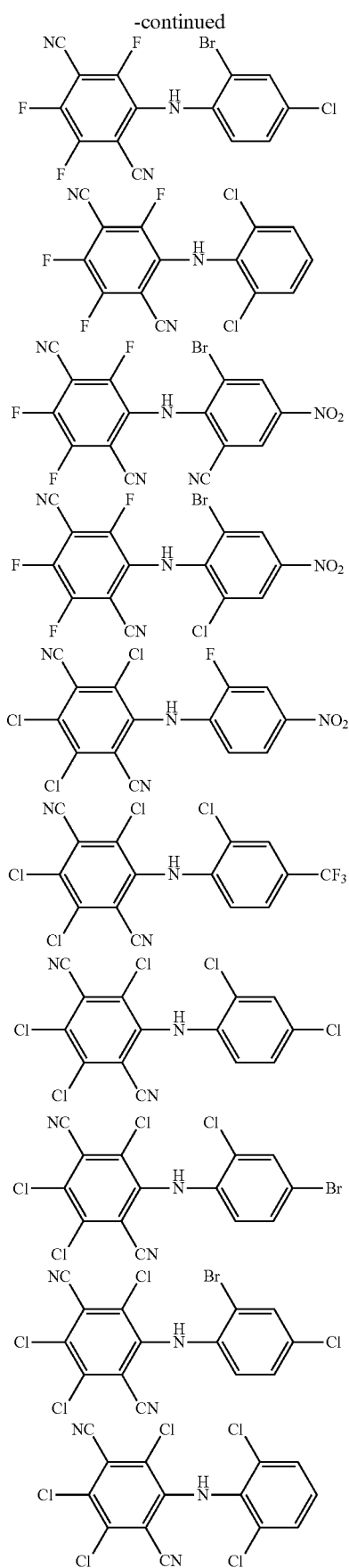

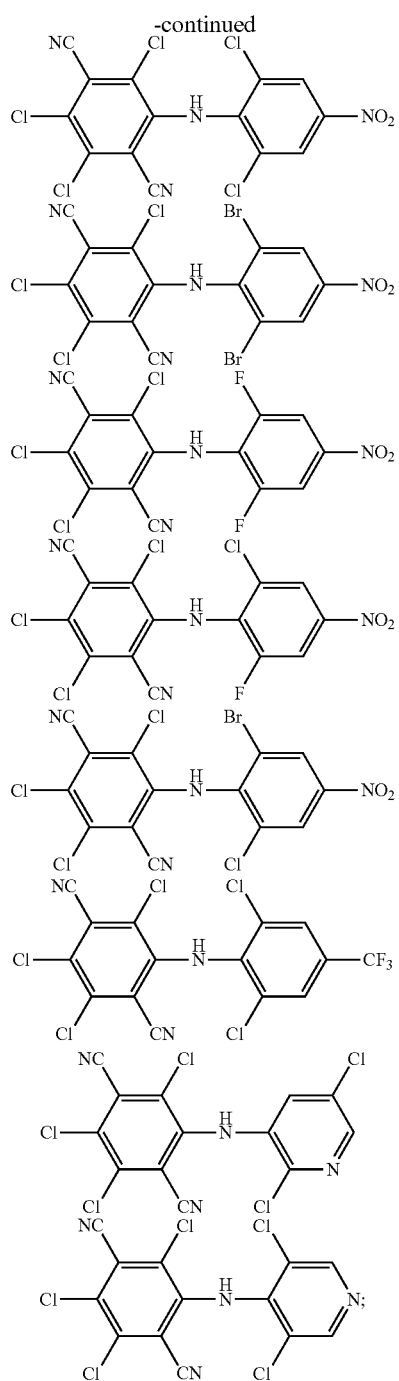

Or the salts formed from the compounds of general formula I-1, I-2 or I-3 with hydrochloric acid, sulfuric acid, phosphoric acid, trifluoroacetic acid, methylsulfonic acid, acetic acid, p-toluenesulfonic acid, sodium or potassium.

The terms used above to definite the compounds of general formula I represent substitutes as follow:

The "halogen" or "halo" is fluorine, chlorine, bromine or iodine.

The "alkyl" stands for straight or branched chain alkyl, such as methyl, ethyl, propyl, isopropyl or tert-butyl.

The "cycloalkyl" is substituted or unsubstituted cyclic alkyl, such as cyclopropyl, cyclopentyl or cyclohexyl. The substitute(s) is(are) methyl, halogen, etc.

The "haloalkyl" stands for straight or branched chain alkyl, in which hydrogen atoms can be all or partly substituted with halogen, such as chloromethyl, dichloromethyl, trichloromethyl, fluoromethyl, difluoromethyl, trifluoromethyl, etc.

The "alkoxy" refers to straight or branched chain alkyl, which is linked to the structure by oxygen atom.

The "haloalkoxy" refers to straight or branched chain alkoxy, in which hydrogen atoms may be all or partly substituted with halogen, such as chloromethoxy, dichloromethoxy, trichloromethoxy, fluoromethoxy, difluoromethoxy, trifluoromethoxy, chlorofluoromethoxy, trifluoroethoxy, etc.

The "alkylthio" refers to straight or branched chain alkyl, which is linked to the structure by sulfur atom.

The "haloalkylthio" refers to straight or branched chain alkylthio, in which hydrogen atoms may be all or partly substituted with halogen, such as chloromethylthio, dichloromethylthio, trichloromethylthio, fluoromethylthio, difluoromethylthio, trifluoromethylthio, chlorofluoromethylthio, etc.

The "alkylamino" refers to straight or branched chain alkyl, which is linked to the structure by nitrogen atom.

The "haloalkylamino" refers to straight or branched chain alkylamino, in which hydrogen atoms may be all or partly substituted with halogen.

The "alkenyl" refers to straight or branched chain alkenyl, such as ethenyl, 1-propenyl, 2-propenyl and different isomer of butenyl, pentenyl and hexenyl. Alkenyl also includes polyene, such as propa-1,2-dienyl and hexa-2,4-dienyl.

The "haloalkenyl" stands for straight or branched chain alkenyl, in which hydrogen atoms can be all or partly substituted with halogen.

The "alkynyl" refers to straight or branched chain alkynyl, such as ethynyl, 1-propynyl, 2-propynyl and different isomer of butynyl, pentynyl and hexynyl. Alkynyl also includes groups including more than one triple bonds, such as hexa-2,5-diynyl.

The "haloalkynyl" stands for straight or branched chain alkynyl, in which hydrogen atoms can be all or partly substituted with halogen.

The alkenoxyl refers to straight or branched chain alkynes is linked to the structure by oxygen, The haloalkenoxyl stands for a straight-chain or branched alkenoxyl, in which hydrogen atoms may be all or partly substituted with halogen. The alkynoxyl refers to straight or branched chain alkynes is linked to the structure by oxygen. The haloalkynoxyl stands for a straight-chain or branched alkynoxyl, in which hydrogen atoms may be all or partly substituted with halogen.

The "alkylsulfinyl" means a straight-chain or branched alkyl is linked to the structure by (—SO—), such as methylsulfinyl.

The "haloalkylsulfinyl" stands for a straight-chain or branched alkylsulfinyl, in which hydrogen atoms may be all or partly substituted with halogen.

The "alkylsulfonyl" means a straight-chain or branched alkyl is linked to the structure by (—$SO_2$—), such as methylsulfonyl.

The "haloalkylsulfonyl" stands for a straight-chain or branched alkylsulfonyl, in which hydrogen atoms may be all or partly substituted with halogen.

The "alkylcarbonyl" means alkyl is linked to the structure by carbonyl, such as $CH_3CO$—, $CH_3CH_2CO$—.

The "haloalkylcarbonyl" stands for a straight-chain or branched alkylcarbonyl, in which hydrogen atoms may be all or partly substituted with halogen, such as $CF_3CO$—.

The "alkylcarbonyloxy" such as $CH_3COO$—, $CH_3CH_2NHCOO$—. The "alkylcarbonylamino" such as $CH_3CONH$—, $CH_3CH_2NHCONH$—. The "alkylsulfonyloxy" means alkyl-$S(O)_2$—O—. The "alkoxyalkoxy" means alkyl-O-alkyl-O—, such as $CH_3OCH_2O$—. The "alkoxycarbonylalkoxy" stands for alkyl —O—CO-alkyl-O—. The "alkoxycarbonyl" means alkyl-O—CO—. The "alkoxycarbonylalkyl" means alkoxycarbonyl-alkyl-, such as $CH_3OCOCH_2$—. The "alkoxycarbonylamino" means alkyl-O—CO—NH—. The "phenylaminocarbonyl" means phenyl-NH—CO—. The "halophenylaminocarbonyl" stands for phenylaminocarbonyl, in which hydrogen atoms on phenyl ring may be all or partly substituted with halogen, such as 4-Clphenyl-NH—CO—, 2,4-2Clphenyl-NH—CO—.

In the general formula I, part of preferred substituents of $R_1$, $R_2$, $R_3$, $R_4$, $R_5$, $R_6$, $R_7$, $R_8$, $R_9$, $R_{10}$ and $R_{11}$ are separately listed in table 1, table 2 and table 3, but without being restricted thereby.

TABLE 1

| $R_1$ substituents ||| 
|---|---|---|
| $R_1$ | $R_1$ | $R_1$ |
| H | $t$-$C_4H_9$ | $t$-$C_4H_9CO$ |
| $CH_3$ | $CH_3CO$ | $CH_3SO_2$ |
| $C_2H_5$ | $C_2H_5CO$ | $C_2H_5SO_2$ |
| $n$-$C_3H_7$ | $n$-$C_3H_7CO$ | $i$-$C_3H_7SO_2$ |
| $i$-$C_3H_7$ | $i$-$C_3H_7CO$ | Ph |
| $n$-$C_4H_9$ | $n$-$C_4H_9CO$ | $PhC_2H_5$ |

TABLE 2

| $R_2(R_3, R_4, R_5, R_6, R_7, R_8, R_9, R_{10})$ substituents |||||
|---|---|---|---|---|
| $R_2(R_3, R_4, R_5, R_6, R_7, R_8, R_9, R_{10})$ | $R_2(R_3, R_4, R_5, R_6, R_7, R_8, R_9, R_{10})$ | $R_2(R_3, R_4, R_5, R_6, R_7, R_8, R_9, R_{10})$ | $R_2(R_3, R_4, R_5, R_6, R_7, R_8, R_9, R_{10})$ | $R_2(R_3, R_4, R_5, R_6, R_7, R_8, R_9, R_{10})$ |
| F | $CF_3O$ | $CF_3CH_2NH$ | $CF_3SO_2$ | $CH_3CONH$ |
| Cl | $CF_3CH_2O$ |  | $CF_3CH_2SO_2$ | $C_2H_5CONH$ |
| Br | $NH_2$ | $CH_3S$ | $CH_2$=$CHCH_2O$ | $CH_3SO_2O$ |
| I | $CH_3NH$ | $C_2H_5S$ | $CCl_2$=$CHCH_2O$ | $C_2H_5SO_2O$ |
| $CH_3O$ | $(CH_3)_2N$ | $CCl_3S$ | $CBr_2$=$CHCH_2O$ | $CH_3OCH_2O$ |
| $C_2H_5O$ | $C_2H_5NH$ | $CH_3SO$ | $CH$≡$CCH_2O$ | $C_2H_5OCH_2O$ |
| $n$-$C_3H_7O$ | $n$-$C_3H_7NH$ | $C_2H_5SO$ | C—Cl=$CCH_2O$ | $CH_3OCH_2CH_2O$ |
| $i$-$C_3H_7O$ | $i$-$C_3H_7NH$ | $CH_3SO_2$ | C—I=$CCH_2O$ | $C_2H_5OCH_2CH_2O$ |
| $n$-$C_4H_9O$ | $n$-$C_4H_9NH$ | $C_2H_5SO_2$ | $CH_3CO_2$ | $CH_3OCOCH_2O$ |
| $i$-$C_4H_9O$ | $t$-$C_4H_9NH$ | $CF_3CH_2SO$ | $C_2H_5CO_2$ | $C_2H_5OCOCH_2O$ |

TABLE 3

$R_{11}$ substituents

| $R_{11}$ | $R_{11}$ | $R_{11}$ | $R_{11}$ |
|---|---|---|---|
| — | $CH_3CH_2O$ | $CH_3SO$ | PhNHCO |
| F | $n\text{-}C_3H_7O$ | $CH_3CH_2SO$ | 4-ClPhNHCO |
| Cl | $i\text{-}C_3H_7O$ | $CF_3SO$ | CHO |
| Br | $n\text{-}C_4H_9O$ | $CH_3SO_2$ | $CO_2H$ |
| I | t-BuO | $CH_3CH_2SO_2$ | $CO_2Na$ |
| $NO_2$ | $CF_3O$ | $CF_3SO_2$ | $CO_2NH_4$ |
| CN | $CF_3CH_2O$ | $CH_3CO$ | $CONH_2$ |
| $CH_3$ | $CF_3CF_2O$ | $CH_3CH_2CO$ | $CONHCH_3$ |
| $C_2H_5$ | $CH_3S$ | $CH_2BrCO$ | $CONHCH_2CH_3$ |
| $n\text{-}C_3H_7$ | $C_2H_5S$ | $CF_3CO$ | $CONH(CH_2)_2CH_3$ |
| $i\text{-}C_3H_7$ | $CCl_3S$ | $CH_3COO$ | $CONHCH(CH_3)_2$ |
| $n\text{-}C_4H_9$ | $CH_2{=}CH$ | $CH_2CH_3COO$ | $CONH(CH_2)_3CH_3$ |
| $i\text{-}C_4H_9$ | $CH_2{=}CHCH_2$ | $CH_3CONH$ | $CONHC(CH_3)_3$ |
| $CH_2F$ | $CCl_2{=}CH$ | $CH_3CH_2CONH$ | $CON(CH_3)_2$ |
| $CH_2Cl$ | $CCl_2{=}CHCH_2$ | $CH_3OCONH$ | $CON(CH_2CH_3)_2$ |
| $CH_2Br$ | $CH{\equiv}C$ | BocNH | $CSNH_2$ |
| $CHF_2$ | $CH{\equiv}CCH_2$ | $CH_3SO_2O$ | $CSNHCH_3$ |
| $CF_3$ | $CCl{\equiv}C$ | $CH_3CH_2SO_2O$ | $CSNHCH_2CH_3$ |
| $CF_3CH_2$ | $CH_2C{\equiv}CCl$ | $CH_3OCH_2$ | $CSN(CH_3)_2$ |
| $CF_3CF_2$ | $CH{=}CH_2CH_2O$ | $CH_3OCH_2CH_2O$ | $CSN(CH_2CH_3)_2$ |
| $(CF_3)_2CF$ | $CCl_2{=}CHCH_2O$ | $CH_3OCOCH_2$ | $SO_2NH_2$ |
| cyclopropyl-CH_2- | $CH{\equiv}CCH_2O$ | $CH_3CH_2OCOCH_2$ | $SO_2NHCH_3$ |
| $CH_3O$ | $CCl{\equiv}CCH_2O$ | $CH_3OCOCH_2O$ | $SO_2NH(CH_3)_2$ |

"—" stands for no substituent. As the same in the following.

In the general formula (I)(A is $A_1$, $A_2$ or $A_3$): When Q is phenyl, the substituted groups of phenyl refer to Table 4. When Q is pyridinyl, the substituted groups of pyridinyl refer to Tables 5-7. When Q is pyrimidinyl, the substituted groups of pyrimidinyl refer to Tables 8-10. When Q is pyridazinyl, the substituted groups of pyridazinyl refer to Tables 11-12. When Q is pyrazinyl, the substituted groups refer to Table 13. When Q is triazinyl, the substituted groups refer to Tables 14-17.

TABLE 4

| $(R_{11})n$ | $(R_{11})n$ | $(R_{11})n$ |
|---|---|---|
| 2-F | 2-Br | 2-$CH_3$-4-Cl-6-$CON(CH_3)_2$ |
| 2,4-2F | 2,6-2Br-4-$NO_2$ | 2-$CH_3$-4-Cl-6-$CONHCH(CH_3)_2$ |
| 2,6-2F | 2,6-2Br-4-$OCF_3$ | 2-$CH_3$-4-Cl-6-$CONHC(CH_3)_3$ |
| 2-F-5-$CH_3$ | 2-Br-4-CN | 2-$CH_3$-4-Br-6-$CO_2CH_3$ |
| 2-F-5-$NO_2$ | 4-Br | 2-$CH_3$-4-Br-6-$CONH_2$ |
| 2-F-4-CN | 2-I | 2-$CH_3$-4-Br-6-$CON(CH_3)_2$ |
| 2,3,4-3F | 4-I | 2-$CH_3$-4-$NO_2$-6-F |
| 2-F-4-$NO_2$ | 2-$NO_2$ | 2-$CH_3$-6-Cl-4-$NO_2$ |
| 2,6-2F-4-$CF_3$ | 2-$NO_2$-4-Cl | 2-$CH_3$-4-$NO_2$-6-Br |
| 2,5-2F-4-$CO_2C_2H_5$ | 2-$NO_2$-4-CN | 2-$CH_3$-4-$NO_2$-6-CN |
| 2,6-2F-4-$NO_2$ | 2-$NO_2$-5-Cl | 2-$CH_3$-4-$NO_2$-6-$CF_3$ |
| 2-Br-6-CN-4-$NO_2$ | 2,6-2$NO_2$-4-Cl | 2-$CH_3$-4-$NO_2$-6-$OCH_3$ |

TABLE 4-continued

| (R₁₁)n | (R₁₁)n | (R₁₁)n |
| --- | --- | --- |
| 2-Cl-6-F-4-NO$_2$ | 2,6-2NO$_2$-4-SOCH$_3$ | 2-CH$_3$-4-NO$_2$-6-SO$_2$CH$_3$ |
| 2-Br-6-Cl-4-NO$_2$ | 2,6-2NO$_2$-4-SO$_2$CH$_3$ | 2-CH$_3$-4-NO$_2$-6-CO$_2$H |
| 2,6-2F-4-OCF$_3$ | 2-NO$_2$-4,6-2Cl— | 2-CH$_3$-4-NO$_2$-6-CO$_2$CH$_3$ |
| 2-F-4-NO$_2$-6-Cl | 2-NO$_2$-4-Cl-6-F | 2-CH$_3$-4,6-2CN |
| 2-F-4-CN-5-CO$_2$CH$_3$ | 2-NO$_2$-4-CN-6-Cl | 2-CH$_3$-4-CN-6-NO$_2$ |
| 2-F-4-CN-5-NO$_2$ | 2-NO$_2$-3-C$_2$H$_5$-6-CO$_2$CH$_3$ | 2-CH$_3$-4-CN-6-CF$_3$ |
| 2-F-4-CN-6-OCH$_3$ | 2-NO$_2$-4-CO$_2$CH$_3$-6-SCH$_3$ | 4-CH$_3$ |
| 2-F-4-NO$_2$-6-Cl | 2-NO$_2$-4-CO$_2$CH$_3$-6-SOCH$_3$ | 2-CH$_3$-4-CN-6-SO$_2$CH$_3$ |
| 2-F-4-NO$_2$-6-Br | 2-NO$_2$-4-CO$_2$CH$_3$-6-SO$_2$CH$_3$ | 2-CH-4-CN-6-CO$_2$CH$_3$ |
| 2-F-4-CN-6-Cl | 2-NO$_2$-4-CO$_2$CH$_3$-6-OCH$_3$ | 2-CH$_3$-4-CN-6-CONH$_2$ |
| 3-F-6-CN | 2-NO$_2$-4-CO$_2$CH$_3$-6-OCH$_2$CH=CH$_2$ | 2-CH$_3$-4-CN-6-CONHCH$_3$ |
| 3-F-4-CN | 2,6-2NO$_2$-3-Cl-4-CF$_3$ | 2-CH$_3$-4-CN-6-CONHCH(CH$_3$)$_2$ |
| 4-F | 2,6-2NO$_2$-3-SCH$_3$-4-CF$_3$ | 2-CH$_3$-4-CF$_3$-6-Br |
| 2-Cl | 2,6-2NO$_2$-3-SOCH$_3$-4-CF$_3$ | 2-CH$_3$-4-CF$_3$-6-NO$_2$ |
| 2,3-2Cl | 2,6-2NO$_2$-3-SO$_2$CH$_3$-4-CF$_3$ | 2-CH$_3$-4-CF$_3$-6-CN |
| 2,4-2Cl | 2,6-2NO$_2$-4-OCH$_3$ | 2-CH$_3$-4-CF$_3$-6-OCH$_3$ |
| 2,4,5-3Cl | 2,6-2NO$_2$-3-OCH$_3$-4-CF$_3$ | 2-CH$_3$-4-CF$_3$-6-CO$_2$CH$_3$ |
| 2,4,6-3Cl | 3-NO$_2$ | 2-CH$_3$-4-CO$_2$C$_2$H$_5$-6-F |
| 2,5-2Cl | 4-NO$_2$ | 2-CH$_3$-4-CO$_2$CH$_3$-6-Cl |
| 2,6-2Cl | 2-CN-5-Cl | 2-CH$_3$-4-CO$_2$CH$_3$-6-NO$_2$ |
| 2-Cl-4-NO$_2$ | 2,4-2Cl-6-CN | 2-CH$_3$-4-CO$_2$CH$_3$-6-CN |
| 2-Cl-5-NO$_2$ | 2-CN-4-NO$_2$-6-Br | 2-CH$_3$-4-CO$_2$CH$_3$-6-CF$_2$ |
| 2-Cl-5-CN | 2-CN-4-Cl-6-NO$_2$ | 3-CH$_3$ |
| 2-Cl-5-CH$_3$ | 2-CN-4-Cl-6-CF$_3$ | 3,4-2CH$_3$ |
| 2-Cl-3-CH$_3$ | 2-CN-4,6-2NO$_2$ | 2,6-2C$_6$H$_5$-4-Cl |
| 2-Cl-3,5-2t-Bu | 2-CN-4-OCH$_3$-6-NO$_2$ | 2-C$_2$H$_5$-6-Br-4-NO$_2$ |
| 2-Cl-4-CF$_3$ | 2-CN-4-SCH$_3$-6-NO$_2$ | 2-C$_2$H$_5$-4,6-2NO$_2$ |
| 2-Cl-5-CF$_3$ | 2-CN-4-SO$_2$CH$_3$-6-NO$_2$ | 2-C$_2$H$_5$-4-NO$_2$-6-CN |
| 2-Cl-4-CH=CH$_2$ | 2-CN-4-SO$_2$CH$_3$-6-CF$_3$ | 2-C$_2$H$_5$-4-NO$_2$-6-Cl |
| 2,6-2Cl-4-CN | 2-CN-4-OCOCH$_3$-6-CF$_3$ | 2-C$_2$H$_5$-4-NO$_2$-6-COCH$_3$ |
| 2,6-2Cl-4-CF$_3$ | 2-CN-4-OCOCH$_2$CH$_3$-6-CF$_3$ | 4-C$_2$H$_5$ |
| 2,6-2Cl-3-CH$_3$ | 2-CN-4-NHCOCH$_3$-6-CF$_3$ | 2-(CH$_2$)$_2$CH$_3$-4-NO$_2$-6-OC$_2$H$_5$ |
| 2,6-2Cl-4-NO$_2$ | 2-CN-4-NHCOCH$_2$CH$_3$-6-CF$_3$ | 2-(CH$_2$)$_2$CH$_3$-4-NO$_2$-6-CF$_3$ |
| 2,6-2Cl-4-C≡CH | 3-CN-5-NO$_2$ | 2-(CH$_2$)$_2$CH$_3$-4-NO$_2$-6-CO$_2$CH$_3$ |
| 2,6-2Cl-4-CO$_2$H | 3-CN-5-OCH$_3$ | 2-(CH$_2$)$_2$CH$_3$-4-NO$_2$-6-SO$_2$CH$_3$ |
| 2,6-2Cl-4-CO$_2$CH$_3$ | 4-CN | 2-n-C$_3$H$_7$-4-CN |
| 2,6-2Cl-4-CONH$_2$ | 2-CH$_3$ | 2-n-C$_4$H$_9$-4-CN |
| 2,6-2Cl-4-CON(CH$_3$)$_2$ | 2,5-2CH$_3$ | 2-t-Bu-4-NO$_2$-6-Cl |
| 2,6-2Cl-4-CONHC(CH$_3$)$_3$ | 2,4,6-3CH$_3$ | 4-t-Bu |
| 2,6-2Cl-4-SO$_2$NH$_2$ | 2-CH$_3$-3-Cl | 2-CH$_2$Cl-4-CN |
| 2,6-2Cl-4-SO$_2$NHCH$_3$ | 2-CH$_3$-4-CN | 2-CF$_3$-4,6-2Cl |
| 2-Cl-4-NO$_2$-5-t-Bu | 2-CH$_3$-4-Cl | 2-CF$_3$-4-CN |
| 2-Cl-4-NO$_2$-5-CF$_3$ | 2,6-2CH$_3$-4-Cl | 2-CH$_3$-4-Cl-6-NO$_2$ |
| 2-Cl-4-NO$_2$-6-Br— | 2-CH$_3$-4-Br | 2-CF$_3$-4-Cl-6-NO$_2$ |
| 2-Cl-4-NO$_2$-6-SCH$_3$ | 2-CH$_3$-5-Cl | 3-CF$_3$ |
| 2-Cl-4-CN-5-Br | 2-CH$_3$-4-OCF$_3$ | 3-CF$_3$-4-CN |
| 2-Cl-4-CN-6-CON(CH$_3$)$_2$ | 2-CH$_3$-4-CO$_2$H | 3-CF$_3$-4-Cl |
| 3-Cl | 2-CH$_3$-4-CO$_2$Na | 3,5-2CF$_3$ |
| 3,4-2Cl | 2-CH$_3$-4-CO$_2$CH$_3$ | 4-CF$_3$ |
| 3,5-2Cl | 2-CH$_3$-4-CO$_2$C$_2$H$_5$ | 2-OCH$_3$-4-NO$_2$ |
| 3-Cl-4-CN | 2-CH$_3$-4-SO$_2$CH$_3$ | 2-OCH$_3$-4-NO$_2$-6-Cl |
| 3-Cl-4-NHCO$_2$CH$_3$ | 2-CH$_3$-6-CO$_2$H | 2-OCH$_3$-4-CN-6-Cl— |
| 3-Cl-4-NHBoc | 2-CH$_3$-4,6-2NO$_2$ | 3,4-2OCH$_3$ |
| 3,5-2Cl-4-CH$_3$ | 2-CH$_3$-4-Cl-6-CN | 4-OCH$_3$ |
| 3,5-2Cl-4-OCH$_2$CH=CCl$_2$ | 2-CH$_3$-4-Cl-6-CO$_2$CH$_3$ | 4-OCF$_3$ |
| 3,5-2Cl-4-OCH$_2$C≡CH | 2-CH$_3$-4-Cl-6-CONH$_2$ | 2-OCH$_2$CF$_3$-4-NO$_2$-6-Br |
| 3,5-2Cl-4OCONHCH$_3$ | 2-CH$_3$-4-Cl-6-CONHCH$_3$ | 2-SOCH$_3$-4-NO$_2$-6-Cl |
| 3,5-2Cl-4-OCON(CH$_3$)$_2$ | 2-CH$_3$-4-Cl-6-CONHCH$_3$ | 2-SO$_2$CH$_3$-4-NO$_2$-6-Cl |

TABLE 4-continued

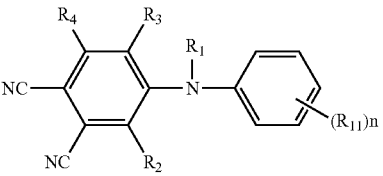

| (R$_{11}$)n | (R$_{11}$)n | (R$_{11}$)n |
|---|---|---|
| 3,5-2Cl-4OCON(n-C$_3$H$_7$)$_2$ | 2-Cl-4-Br | 2-COCH$_3$ |
| 3,5-2Cl-4-NHBoc | 2-CH$_3$-3-Cl-4,6-2NO$_2$ | 2-CO$_2$CH$_3$-4-F |
| 4-Cl | 2,3,5-3Cl-4,6-2CN | 2-Br-4-Cl |
| 2,4-2NO$_2$ | | |

TABLE 5

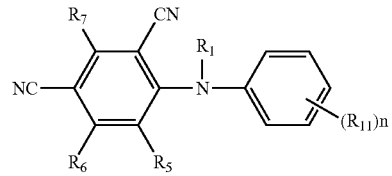

| (R$_{11}$)n | (R$_{11}$)n | (R$_{11}$)n | (R$_{11}$)n |
|---|---|---|---|
| — | 5-COCH$_3$ | 3-Br-5-CH$_3$ | 3-CONH$_2$-5-Cl |
| 3-F | 5-CO$_2$CH$_3$ | 3-Br-6-CH$_3$ | 3-CONH$_2$-6-CF$_3$ |
| 3-Cl | 3-CHO | 3-Br-5-CF$_3$ | 4-CONH$_2$-6-CH$_3$ |
| 3-Br | 4-CHO | 5-Br-6-C$_2$H$_5$ | 4-CONH$_2$-6-OCH$_3$ |
| 3-I | 5-CHO | 4-I-5-CH$_3$ | 3,5-2F-4-CF$_3$ |
| 4-Cl | 3-NH$_2$ | 4-I-5-CF$_3$ | 3,6-2F-4-CF$_3$ |
| 4-Br | 4-NH$_2$ | 5-I-6-C$_2$H$_5$ | 3-F-5-CN-6-Cl |
| 4-I | 5-NH$_2$ | 3-NO$_2$-4-Cl | 3-F-5-CO$_2$CH$_3$-6-Cl |
| 5-Cl | 6-NH$_2$ | 3-NO$_2$-4-CH$_3$ | 3-F-5-CONH$_2$-6-Cl |
| 5-Br | 3-CONH$_2$ | 3-NO$_2$-5-Cl | 3-F-5-CONHCH(CH$_3$)$_2$-6-Cl |
| 5-I | 4-CONH$_2$ | 3-NO$_2$-5-Br | 3,5-2Cl-4-CH$_3$ |
| 6-Cl | 5-CONH$_2$ | 3-NO$_2$-5-I | 3,5-2Cl-6-CH$_3$ |
| 6-Br | 3-F-5-Cl | 3-NO$_2$-4,6-2Cl | 3,5-2Cl-4,6-2CH$_3$ |
| 3-NO$_2$ | 3-F-5-CN | 3-NO$_2$-6-Cl | 3,5-2Cl-6-OCH$_2$CO$_2$Me |
| 4-NO$_2$ | 3-F-4-CF$_3$ | 3-NO$_2$-6-CH$_3$ | 3,6-2Cl-5-CF$_3$ |
| 5-NO$_2$ | 3-F-5-CF$_3$ | 3-NO$_2$-6-OCH$_3$ | 3,5,6-3Cl |
| 6-NO$_2$ | 3-F-4-CHO | 4-NO$_2$-6-CH$_3$ | 3-Br-5-CF$_3$-6-Cl |
| 3-CN | 4,6-2F | 5-NO$_2$-6-CH$_3$ | 3,5-2Br-4-CH$_3$ |

TABLE 5-continued

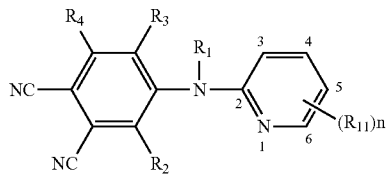
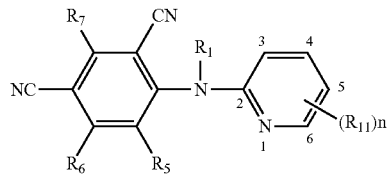
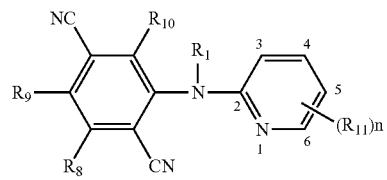

| $(R_{11})n$ | $(R_{11})n$ | $(R_{11})n$ | $(R_{11})n$ |
|---|---|---|---|
| 4-CN | 5-F-6-CH$_3$ | 5-NO$_2$-6-NHCOCH$_3$ | 3,5-2Br-6-CH$_3$ |
| 5-CN | 3,5-2Cl | 3-CN-6-CH$_3$ | 3-Br-5,6-2CH$_3$ |
| 6-CN | 4,6-2Cl | 3-CN-4-OCH$_3$ | 3-NO$_2$-4-CH$_3$-5-Br |
| 3-CH$_3$ | 3,5-2Br | 3-CH$_3$-5-CN | 3,5-2CN-6-Cl |
| 4-CH$_3$ | 3-Cl-5-Br | 4-CH$_3$-5-Br | 3-CN-5-F-6-Cl |
| 5-CH$_3$ | 3-Cl-5-NO$_2$ | 4-CH$_3$-5-NO$_2$ | 3-CN-4-CF$_3$-6-Cl |
| 4-C$_2$H$_5$ | 3-Cl-5-CN | 4-CH$_3$-5-NH$_2$ | 3,5-2CN-6-CH$_3$ |
| 3-CF$_3$ | 3-Cl-5-CF$_3$ | 4,6-2CH$_3$ | 3-CN-4-CH$_3$-6-Cl |
| 4-CF$_3$ | 3-Cl-5-CO$_2$CH$_3$ | 4-CH$_2$Cl-6-Cl | 4-CH$_3$-5-CN-6-Cl |
| 5-CCl$_3$ | 3-Cl-5-CONH$_2$ | 3-CF$_3$-5-Cl | 3-CF$_3$-5-Br-6-Cl |
| 5-CF$_3$ | 3-Cl-5-CON(CH$_3$)$_2$ | 3-CF$_3$-5-Br | 3-CO$_2$CH$_3$-5-F-6-Cl |
| 3-OCH$_3$ | 3-Cl-5-SO$_2$NH$_2$ | 3-CF$_3$-6-Cl | 3-CO$_2$C$_2$H$_5$-4-Cl-6-CH$_3$ |
| 4-OCH$_3$ | 4-Cl-5-NO$_2$ | 4-CF$_3$-5-CO$_2$CH$_3$ | 3-CONH$_2$-4-CF$_3$-6-Cl |
| 5-OCH$_3$ | 4-Cl-6-CH$_3$ | 4-CH$_2$CO$_2$CH$_3$-6-Cl | 3-CONH$_2$-5-F-6-Cl |
| 6-OCH$_3$ | 5-Cl-6-CH$_3$ | 3-CHO-4-I | 3-CONHCH(CH$_3$)$_2$-5-F-6-Cl |
| 6-OC(CH$_3$)$_3$ | 3-Br-5-F | 4-CHO-6-Cl | 3-CN-4,6-2CH$_3$-5-Br |
| 3-NHCOCH$_3$ | 3-Br-5-Cl | 4-CO$_2$CH$_3$-6-CH$_3$ | 3-CSNH$_2$-4-CF$_3$-6-Cl |
| 3-CO$_2$CH$_5$ | 3-Br-5-NO$_2$ | 4-CO$_2$CH$_3$-6-OCH$_3$ | 3-CSNH$_2$-5-F-6-Cl |
| 4-CO$_2$C$_2$H$_5$ | 3-Br-5-CN | 3-CONH$_2$-6-CH$_3$ | 3-CSNHCH(CH$_3$)$_2$-5-F-6-Cl |
| 3,4,5,6-4Cl | | | |

TABLE 6

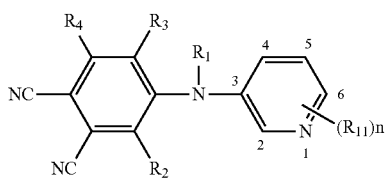
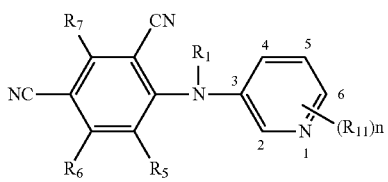
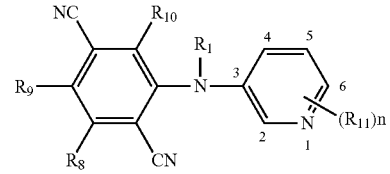

| $(R_{11})n$ | $(R_{11})n$ | $(R_{11})n$ | $(R_{11})n$ |
|---|---|---|---|
| — | 2-CH$_3$ | 2-Cl-5-CH$_3$ | 5-CO$_2$H-6-Cl |
| 2-F | 4-CH$_3$ | 2-Cl-5-CF$_3$ | 5-CO$_2$CH$_3$-6-Cl |

TABLE 6-continued

| $(R_{11})n$ | $(R_{11})n$ | $(R_{11})n$ | $(R_{11})n$ |
|---|---|---|---|
| 2-Br | 4-$CF_3$ | 2-Cl-4-CHO | 5-$CONH_2$-6-Cl |
| 2-Cl | 5-$CF_3$ | 2-Cl-5-$SO_2NH_2$ | 2,5,6-3F |
| 2-I | 6-$CF_3$ | 5-Cl-6-CN | 2,6-2F-5-Cl |
| 4-F | 2-$OCH_3$ | 2,6-2Br | 2,6-2F-4-$CF_3$ |
| 4-Cl | 6-$OCH_3$ | 2-Br-4-$CH_3$ | 2,5-2F-4-$CF_3$ |
| 4-I | 6-$OC_2H_5$ | 2-Br-6-$OCH_3$ | 2,5,6-3Cl |
| 5-F | 6-$NH_2$ | 5-Br-6-$OCH_3$ | 2,6-2Cl-4-$CF_3$ |
| 5-Cl | 6-CHO | 5-$NO_2$-6-Cl | 2,6-2Cl-5-CN |
| 5-Br | 4-$CO_2CH_3$ | 5-$NO_2$-6-Br | 2,6-2Br-4-$CH_3$ |
| 5-I | 5-$CO_2CH_3$ | 2,6-2$CH_3$ | 2,6-2Cl-5-$CO_2CH_3$ |
| 6-F | 6-$CO_2CH_3$ | 2-$CH_3$-6-F | 2,6-2Cl-5-$CONH_2$ |
| 6-Cl | 5-$CONH_2$ | 2-$CH_3$-6-Cl | 4-$CF_3$-5,6-2F |
| 6-Br | 6-$CONH_2$ | 2-$CH_3$-6-$NH_2$ | 2-$CO_2H$-4,5,6-3Cl |
| 6-I | 2-$OCH_2CO_2CH_3$ | 4-$CH_3$-6-Cl | 2,5,6-3F-4-Br |
| 2-$NO_2$ | 2-F-5-$CH_3$ | 4-$CH_3$-6-$OCH_3$ | 2,5,6-3F-4-CN |
| 4-$NO_2$ | 2-F-5-$CF_3$ | 5-$CH_3$-6-Br | 2,5,6-3F-4-$CO_2H$ |
| 5-$NO_2$ | 2,5-2Cl | 2-$OCH_3$-5-Br | 2,4,6-3Br-5-F |
| 6-$NO_2$ | 2,6-2Cl | 2-$OCH_3$-6-Br | 2,4-2$CH_3$-5-CN-6-Cl |
| 2-CN | 2-Cl-4-$CH_3$ | 2-$OCH_3$-5-$CF_3$ | 5-$CSNH_2$-6-Cl |
| 4-CN | 2-Cl-4-$CF_3$ | 2,6-2($OCH_3$)$_2$ | 5-$CSNHCH_3$-6-Cl |
| 5-CN | 2-Cl-5-$NO_2$ | 4-CHO-5-Cl | 5-$CSN(CH_3)_2$-6-Cl |
| 6-CN | | | |

TABLE 7

| $(R_{11})n$ | $(R_{11})n$ | $(R_{11})n$ | $(R_{11})n$ |
|---|---|---|---|
| — | 2-$CF_3$ | 3,5-2Cl | 2,6-2$NO_2$ |
| 2-F | 3-$CF_3$ | 3,5-2Br | 3,5-2$CH_3$ |
| 3-F | 5-$CF_3$ | 3,5-2I | 2,6-2$CH_3$ |
| 2-Cl | 2-$OCH_3$ | 2-F-5-$CH_3$ | 3-$CH_3$-2-Cl |
| 2-Br | 3-$OCH_3$ | 2-F-3-CHO | 3,6-2Cl-5-$CF_3$ |
| 2-I | 3-CHO | 2-Cl-3-$NO_2$ | 2-Cl-3-$CO_2C_2H_5$-6-$CH_3$ |
| 3-Cl | 2-$CO_2CH_3$ | 2-Cl-5-$CF_3$ | 2,6-2$CH_3$-3-$CO_2C_2H_5$ |
| 3-Br | 2-$CONH_2$ | 2-Cl-3-CHO | 2,3,5,6-4F |

TABLE 7-continued

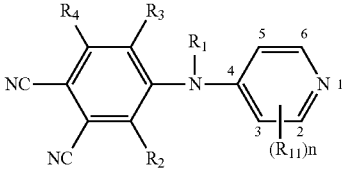

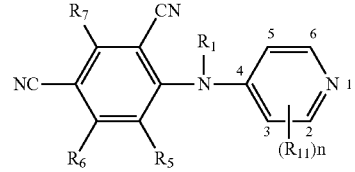

| (R₁₁)n | (R₁₁)n | (R₁₁)n | (R₁₁)n |
|---|---|---|---|
| 3-I | 3-CO₂CH₃ | 2-Cl-5-CO₂C₂H₅ | 3,5-2F-2,6-2Br |
| 3-NO₂ | 3-SO₂NH₂ | 3-Cl-5-NO₂ | 3,5-2F-2,6-2Br |
| 2-CH₃ | 2,6-2F | 3-Cl-5-CF₃ | 2-CSNH₂ |
| 3-CH₃ | 2,6-2Cl | 3-Br-5-CN | 2-CSNHCH₃ |

TABLE 8

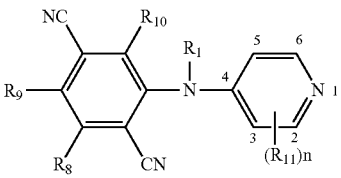

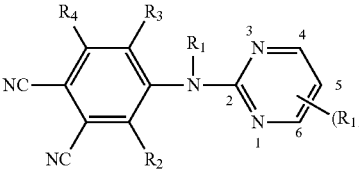

| (R₁₁)n | (R₁₁)n | (R₁₁)n | (R₁₁)n |
|---|---|---|---|
| — | 5-CO₂C₂H₅ | 4-Cl-5-NO₂ | 4-CF₃-5-CO₂C₂H₅ |
| 4-F | 5-CO₂C(CH₃) | 4-Cl-5-CN | 4-CF₃-5-CONH₂ |
| 4-Cl | 5-CHO | 4-Cl-5-CH₃ | 4-OCH₃-5-Br |
| 4-CN | 5-NH₂ | 4-Cl-6-CH₃ | 4,6-2OCH₃ |
| 4-NO₂ | 5-CONH₂ | 4-Cl-6-CH(CH₃)₂ | 4-CO₂CH₃-6-Cl |
| 4-CH₃ | 5-CONHCH₃ | 4-Cl-5-CF₃ | 4-CO₂C₂H₅-6-Cl |
| 4-CF₃ | 5-CONHC₂H₅ | 4-Cl-5-OCH₃ | 4-CO₂CH₃-6-CH₃ |
| 4-OCH₃ | 5-CONHCH(CH₃)₂ | 4-Cl-6-OCH₃ | 4-CO₂C₂H₅-6-CH₃ |
| 4-SCH₃ | 5-CSNH₂ | 4-Cl-5-CO₂CH₃ | 5-CO₂C₂H₅-6-CH₃ |
| 4-NH₂ | 5-CSNHCH₃ | 4-Cl-5-CONHCH₃ | 4-N(CH₃)₂-5-F |
| 5-F | 4-F-5-Cl | 4-CN-6-CH₃ | 4,6-2F-5-Cl |
| 5-Br | 4-Cl-5-F | 4,6-2CH₃ | 4,6-2F-5-Br |
| 5-I | 4,5-2Cl | 4-CH₃-5-CO₂C₂H₅ | 4,6-2Cl-5-Br |
| 5-CN | 4,6-2Cl | 4-CH₃-5-CO₂H | 4,5-2Cl-6-CH₃ |
| 5-C₂H₅ | 4-Cl-5-Br | 4-CH₃-5-CONH₂ | 4,6-2Cl-5-CHO |
| 5-CH₂CH₂CH₃ | 4-Cl-5-I | 4-C(CH₃)₃-6-CF₃ | 4-Cl-5-NO₂-6-CH₃ |
| 5-CO₂CH₃ | 4,6-2Br | 4-CF₃-5-CO₂CH₃ | 4-Cl-5-NO₂-6-CO₂C₂H₅ |

TABLE 9

| (R11)n | (R11)n | (R11)n | (R11)n |
|---|---|---|---|
| — | 2,5-2Cl | 2-CH3-6-Cl | 2-SCH3-5-CONH2 |
| 2-F | 2,6-2Cl | 5-CH3-6-Cl | 2-SO2CH3-6-Cl |
| 2-Cl | 2-Cl-5-Br | 2-CH3-5-CN | 2-SO2CH3-5-Br |
| 2-OC2H5 | 2-Cl-5-I | 2-CH3-5-C(CH3)3 | 2-SO2CH3-6-OCH3 |
| 2-SCH3 | 2-Cl-5-NO2 | 2-CF3-5-CO2C2H5 | 5-CHO-6-Cl |
| 2-SOCH3 | 2-Cl-5-CN | 2-OCH3-6-Cl | 5-CHO-6-NH2 |
| 2-SO2CH3 | 2-Cl-5-CH3 | 2-SCH3-6-Cl | 5-CO2H-6-Cl |
| 2-NHCH3 | 2-Cl-6-CH3 | 2-SCH3-5-Br | 2-NH2-6-CH(CH3)2 |
| 5-F | 2-Cl-5-CF3 | 2-SCH3-5-CN | 2,6-2F-5-Cl |
| 6-Cl | 2-Cl-5-OCH3 | 2-SCH3-6-CH3 | 2,6-2Cl-5-NO2 |
| 6-NHCH3 | 2-Cl-6-CO2CH3 | 2-SCH3-6-CF3 | 2,6-Br-5-NO2 |
| 6-CH3 | 2,6-2Br | 2-SCH3-5-OCH3 | 2-Cl-5-NO2-6-CO2C2H5 |
| 6-CF3 | 2-Br-5-CN | 2-SCH3-6-OCH3 | 2-Cl-5-NO2-6-CH3 |
| 5,6-2F | 2-NO2-6-NH2 | 2-SCH3-5-CO2C2H5 | 2-CF3-5,6-2CH3 |
| 2-F-5-Cl | 5-NO2-6-Cl | 2-SC2H5-5-CO2C2H5 | 2-SCH3-5-CN-6-Cl |
| 2-Cl-5-F | 5-CN-6-CH3 | 2-SCH3-5-CO2H | 2-SO2CH3-5-CN-6-Cl |

TABLE 10

| (R11)n | (R11)n | (R11)n | (R11)n |
|---|---|---|---|
| — | 4-Cl | 2,4-2Br | 2-SCH3-4-CO2CH3 |
| 2-F | 4-Br | 4,6-2Br | 2-SCH3-4-CO2H |
| 2-Cl | 2,4-2F | 2-OCH3-4-Cl | 2-SCH3-4-CONH2 |
| 2-Br | 4,6-2F | 2-OCH3-4-Br | 2-SCH3-4-CSNH2 |
| 2-I | 2,4,6-3F | 2,4-OCH3 | 2-SO2CH3-4-Cl |
| 2-CN | 2,4-2Cl | 4,6-OCH3 | 2-CH3-4,6-2Cl |
| 2-OCH3 | 4,6-2Cl | 2-OC2H5-4-Cl | 2-Cyclopropyl-4-Cl |
| 2-SCH3 | 2-Cl-4-OCH3 | 2-OC2H5-4-Br | 2-Cyclopropyl-4,6-2Cl |
| 2-NH2 | 2-Cl-4-N(Me)2 | 2-SCH3-4-Cl | 2-Cyclopropyl-4,6-2OCH3 |

TABLE 11

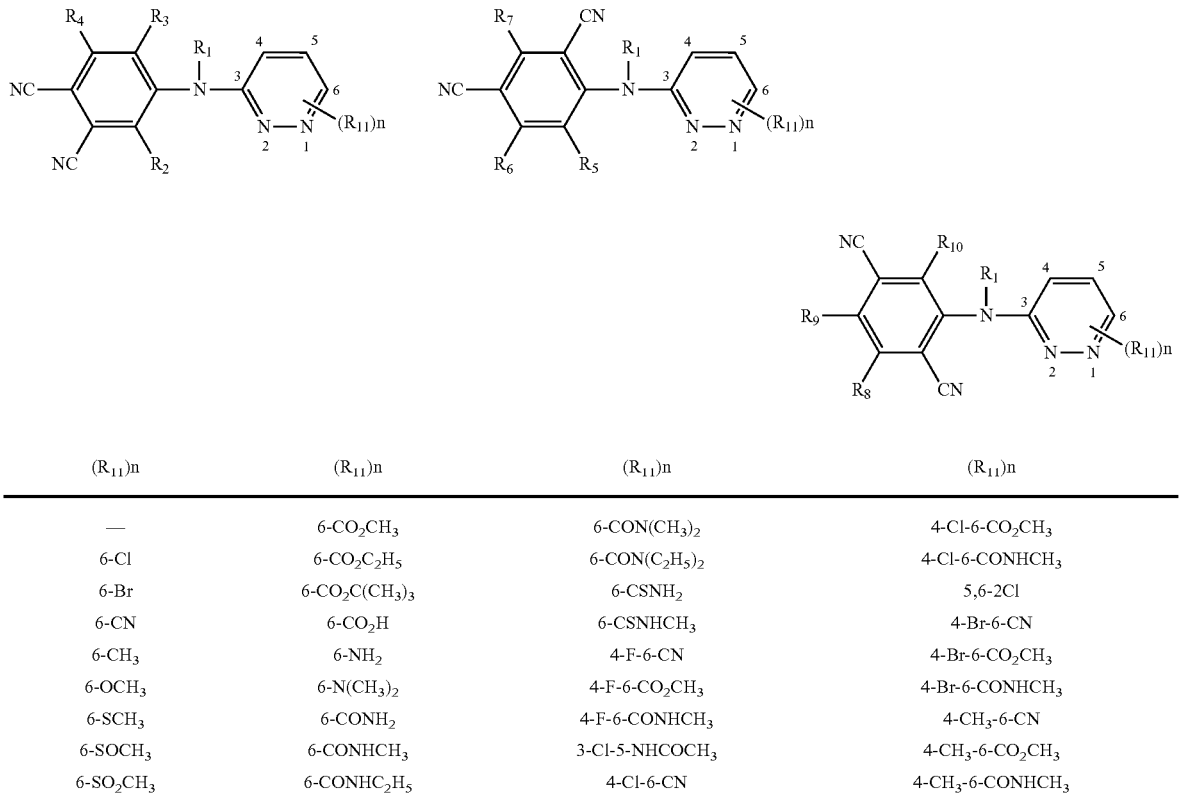

| $(R_{11})n$ | $(R_{11})n$ | $(R_{11})n$ | $(R_{11})n$ |
|---|---|---|---|
| — | 6-$CO_2CH_3$ | 6-$CON(CH_3)_2$ | 4-Cl-6-$CO_2CH_3$ |
| 6-Cl | 6-$CO_2C_2H_5$ | 6-$CON(C_2H_5)_2$ | 4-Cl-6-$CONHCH_3$ |
| 6-Br | 6-$CO_2C(CH_3)_3$ | 6-$CSNH_2$ | 5,6-2Cl |
| 6-CN | 6-$CO_2H$ | 6-$CSNHCH_3$ | 4-Br-6-CN |
| 6-$CH_3$ | 6-$NH_2$ | 4-F-6-CN | 4-Br-6-$CO_2CH_3$ |
| 6-$OCH_3$ | 6-$N(CH_3)_2$ | 4-F-6-$CO_2CH_3$ | 4-Br-6-$CONHCH_3$ |
| 6-$SCH_3$ | 6-$CONH_2$ | 4-F-6-$CONHCH_3$ | 4-$CH_3$-6-CN |
| 6-$SOCH_3$ | 6-$CONHCH_3$ | 3-Cl-5-$NHCOCH_3$ | 4-$CH_3$-6-$CO_2CH_3$ |
| 6-$SO_2CH_3$ | 6-$CONHC_2H_5$ | 4-Cl-6-CN | 4-$CH_3$-6-$CONHCH_3$ |

TABLE 12

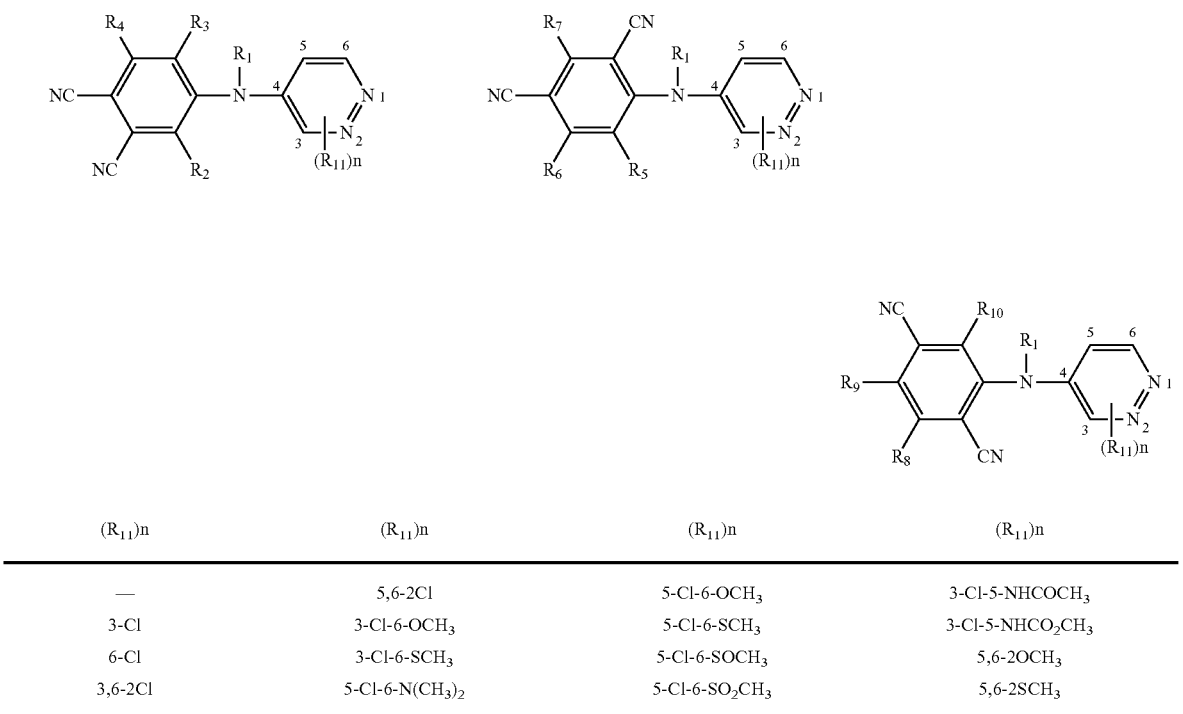

| $(R_{11})n$ | $(R_{11})n$ | $(R_{11})n$ | $(R_{11})n$ |
|---|---|---|---|
| — | 5,6-2Cl | 5-Cl-6-$OCH_3$ | 3-Cl-5-$NHCOCH_3$ |
| 3-Cl | 3-Cl-6-$OCH_3$ | 5-Cl-6-$SCH_3$ | 3-Cl-5-$NHCO_2CH_3$ |
| 6-Cl | 3-Cl-6-$SCH_3$ | 5-Cl-6-$SOCH_3$ | 5,6-2$OCH_3$ |
| 3,6-2Cl | 5-Cl-6-$N(CH_3)_2$ | 5-Cl-6-$SO_2CH_3$ | 5,6-2$SCH_3$ |

TABLE 13

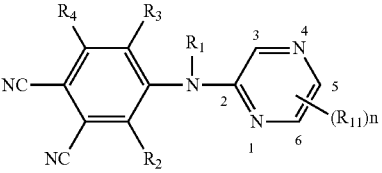

| $(R_{11})n$ | $(R_{11})n$ | $(R_{11})n$ | $(R_{11})n$ |
|---|---|---|---|
| — | 6-$CO_2CH_3$ | 6-$CONHCH_3$ | 4-$CH_3$-6-CN |
| 6-Cl | 6-$CO_2C_2H_5$ | 6-$CONHC_2H_5$ | 4-F-6-$CO_2CH_3$ |
| 6-Br | 6-$CO_2C(CH_3)_3$ | 6-$CON(CH_3)_2$ | 4-Cl-6-$CO_2CH_3$ |
| 6-CN | 6-$CO_2H$ | 6-$CSNH_2$ | 4-Br-6-$CO_2CH_3$ |
| 6-$CH_3$ | 6-$CO_2Na$ | 6-$CSNHCH_3$ | 4-$CH_3$-6-$CO_2CH_3$ |
| 6-$OCH_3$ | 6-$CO_2NH_4$ | 5,6-2Cl | 4-F-6-$CONHCH_3$ |
| 6-$SCH_3$ | 6-$NH_2$ | 4-F-6-CN | 4-Cl-6-$CONHCH_3$ |
| 6-$SOCH_3$ | 6-$N(CH_3)_2$ | 4-Cl-6-CN | 4-Br-6-$CONHCH_3$ |
| 6-$SO_2CH_3$ | 6-$CONH_2$ | 4-Br-6-CN | 4-$CH_3$-6-$CONHCH_3$ |

TABLE 14

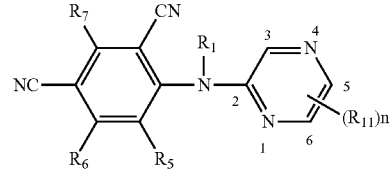

| $(R_{11})n$ | $(R_{11})n$ | $(R_{11})n$ | $(R_{11})n$ |
|---|---|---|---|
| 4-Cl | 4-$OCH_3$-6-$NHCH_3$ | 4-$N(CH_3)_2$ | 4-NH-i-Pr-6-$NHCOCH_3$ |
| 4-CN | 4,6-2$SCH_3$ | 4-$NH_2$-6-Cl | 4-NH-i-Pr-6-$NH_2$ |
| 4-$SCH_3$ | 4-$SCH_3$-6-Cl | 4-$NH_2$-6-$OCH_3$ | 4-NH-i-Pr-6-$NHCH_3$ |
| 4-$SOCH_3$ | 4-$SCH_3$-6-$NHCH_3$ | 4-$NH_2$-6-$SCH_3$ | 4-NH-t-Bu-6-Cl |
| 4-$SO_2CH_3$ | 4-$SOCH_3$-6-Cl | 4-$NH_2$-6-$SOCH_3$ | 4-NH-t-Bu-6-CN |
| 4,6-2Cl | 4-$SO_2CH_3$-6-Cl | 4-$NH_2$-6-$SO_2CH_3$ | 4-NH-t-Bu-6-$OCH_3$ |
| 4-CN-6-Cl | 4-$NHCOCH_3$-6-Cl | 4-NH-i-Pr-6-Cl | 4-NH-t-Bu-6-$SCH_3$ |
| 4,6-2$CH_3$ | 4-$NHCOCH_3$-6-$OCH_3$ | 4-NH-i-Pr-6-CN | 4-NH-t-Bu-6-$NH_2$ |
| 4,6-2$OCH_3$ | 4-$NHCOCH_3$-6-$SCH_3$ | 4-NH-i-Pr-6-$OCH_3$ | 4-NH-t-Bu-6-$NHCH_3$ |
| 4-$OCH_3$-6-Cl | 4-$NHCOCH_3$-6-$SO_2CH_3$ | 4-NH-i-Pr-6-$SCH_3$ | 4-NH-t-Bu-6-$NHCOCH_3$ |

TABLE 15

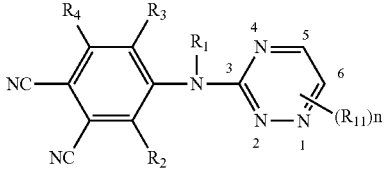

| (R₁₁)n | (R₁₁)n | (R₁₁)n | (R₁₁)n |
|---|---|---|---|
| 5-F-6-CN | 5-Br-6-CO₂CH₃ | 6-CO₂CH₃ | 6-CON(C₂H₅)₂ |
| 5-Cl-6-CN | 5-F-6-CONHCH₃ | 6-CO₂H | 6-CSNH₂ |
| 5-Br-6-CN | 5-Cl-6-CONHCH₃ | 6-CONH₂ | 6-CSNHCH₃ |
| 5-CH₃-6-CN | 5-Br-6-CONHCH₃ | 6-CONHCH₃ | 6-CSNHC₂H₅ |
| 5-F-6-CO₂CH₃ | 5-CH₃-6-CO₂CH₃ | 6-CONHC₂H₅ | 6-CSN(CH₃)₂ |
| 5-Cl-6-CO₂CH₃ | 6-CN | 6-CON(CH₃)₂ | 6-CSN(C₂H₅)₂ |

TABLE 16

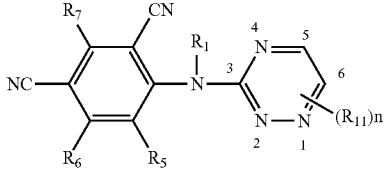

| (R₁₁)n | (R₁₁)n | (R₁₁)n | (R₁₁)n |
|---|---|---|---|
| 3-CN | 3-CONHCH₃ | 3-CSN(CH₃)₂ | 3-CO₂CH₃-6-Cl |
| 3-CO₂CH₃ | 3-CONHC₂H₅ | 3-CSN(C₂H₅)₂ | 3-CO₂CH₃-6-Br |
| 3-CO₂C₂H₅ | 3-CON(CH₃)₂ | 3-CN-6-F | 3-CO₂CH₃-6-CH₃ |
| 3-CO₂H | 3-CON(CH₂H₅)₂ | 3-CN-6-Cl | 3-CONHCH₃-6-F |
| 3-CO₂Na | 3-CSNH₂ | 3-CN-6-Br | 3-CONHCH₃-6-Cl |
| 3-CO₂NH₄ | 3-CSNHCH₃ | 3-CN-6-CH₃ | 3-CONHCH₃-6-Br |
| 3-CONH₂ | 3-CSNHC₂H₅ | 3-CO₂CH₃-6-F | 3-CONHCH₃-6-CH₃ |

TABLE 17

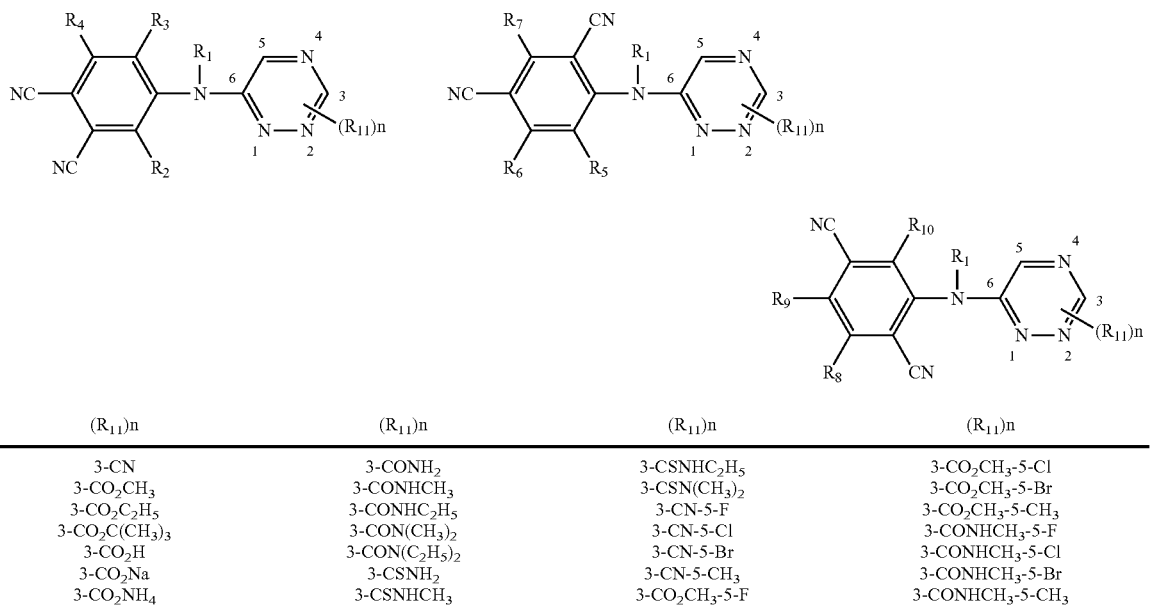

| $(R_{11})n$ | $(R_{11})n$ | $(R_{11})n$ | $(R_{11})n$ |
|---|---|---|---|
| 3-CN | 3-CONH$_2$ | 3-CSNHC$_2$H$_5$ | 3-CO$_2$CH$_3$-5-Cl |
| 3-CO$_2$CH$_3$ | 3-CONHCH$_3$ | 3-CSN(CH$_3$)$_2$ | 3-CO$_2$CH$_3$-5-Br |
| 3-CO$_2$C$_2$H$_5$ | 3-CONHC$_2$H$_5$ | 3-CN-5-F | 3-CO$_2$CH$_3$-5-CH$_3$ |
| 3-CO$_2$C(CH$_3$)$_3$ | 3-CON(CH$_3$)$_2$ | 3-CN-5-Cl | 3-CONHCH$_3$-5-F |
| 3-CO$_2$H | 3-CON(C$_2$H$_5$)$_2$ | 3-CN-5-Br | 3-CONHCH$_3$-5-Cl |
| 3-CO$_2$Na | 3-CSNH$_2$ | 3-CN-5-CH$_3$ | 3-CONHCH$_3$-5-Br |
| 3-CO$_2$NH$_4$ | 3-CSNHCH$_3$ | 3-CO$_2$CH$_3$-5-F | 3-CONHCH$_3$-5-CH$_3$ |

The present invention is also explained by the following compounds in Table 18, Table 19 and Table 20, but without being restricted thereby.

TABLE 18

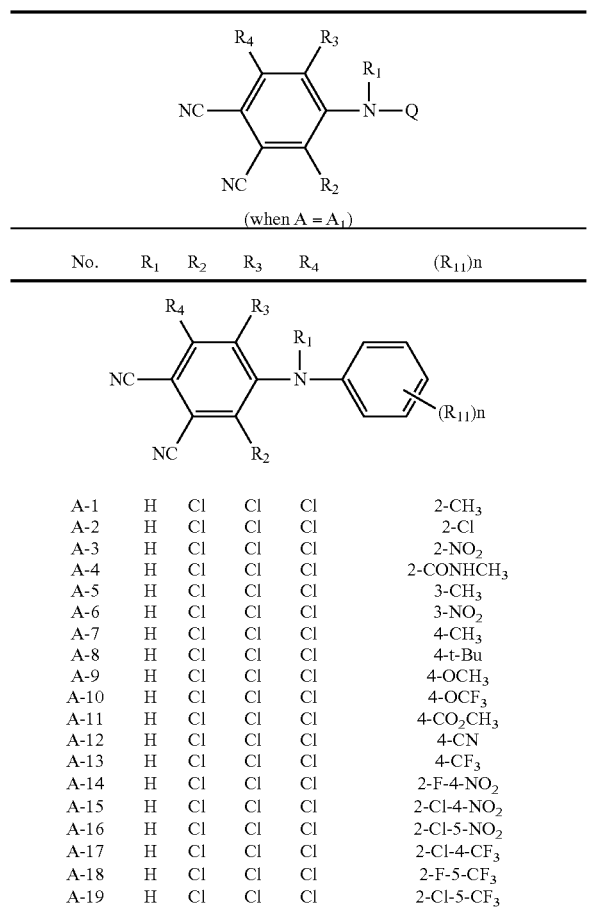

(when A = A$_1$)

| No. | R$_1$ | R$_2$ | R$_3$ | R$_4$ | $(R_{11})n$ |
|---|---|---|---|---|---|
| A-1 | H | Cl | Cl | Cl | 2-CH$_3$ |
| A-2 | H | Cl | Cl | Cl | 2-Cl |
| A-3 | H | Cl | Cl | Cl | 2-NO$_2$ |
| A-4 | H | Cl | Cl | Cl | 2-CONHCH$_3$ |
| A-5 | H | Cl | Cl | Cl | 3-CH$_3$ |
| A-6 | H | Cl | Cl | Cl | 3-NO$_2$ |
| A-7 | H | Cl | Cl | Cl | 4-CH$_3$ |
| A-8 | H | Cl | Cl | Cl | 4-t-Bu |
| A-9 | H | Cl | Cl | Cl | 4-OCH$_3$ |
| A-10 | H | Cl | Cl | Cl | 4-OCF$_3$ |
| A-11 | H | Cl | Cl | Cl | 4-CO$_2$CH$_3$ |
| A-12 | H | Cl | Cl | Cl | 4-CN |
| A-13 | H | Cl | Cl | Cl | 4-CF$_3$ |
| A-14 | H | Cl | Cl | Cl | 2-F-4-NO$_2$ |
| A-15 | H | Cl | Cl | Cl | 2-Cl-4-NO$_2$ |
| A-16 | H | Cl | Cl | Cl | 2-Cl-5-NO$_2$ |
| A-17 | H | Cl | Cl | Cl | 2-Cl-4-CF$_3$ |
| A-18 | H | Cl | Cl | Cl | 2-F-5-CF$_3$ |
| A-19 | H | Cl | Cl | Cl | 2-Cl-5-CF$_3$ |

TABLE 18-continued

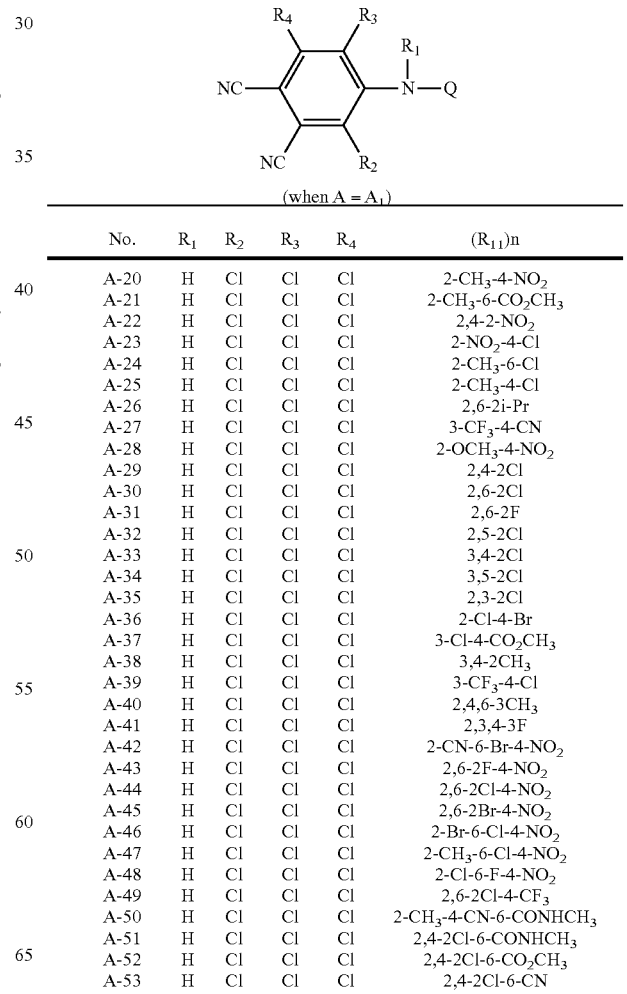

(when A = A$_1$)

| No. | R$_1$ | R$_2$ | R$_3$ | R$_4$ | $(R_{11})n$ |
|---|---|---|---|---|---|
| A-20 | H | Cl | Cl | Cl | 2-CH$_3$-4-NO$_2$ |
| A-21 | H | Cl | Cl | Cl | 2-CH$_3$-6-CO$_2$CH$_3$ |
| A-22 | H | Cl | Cl | Cl | 2,4-2-NO$_2$ |
| A-23 | H | Cl | Cl | Cl | 2-NO$_2$-4-Cl |
| A-24 | H | Cl | Cl | Cl | 2-CH$_3$-6-Cl |
| A-25 | H | Cl | Cl | Cl | 2-CH$_3$-4-Cl |
| A-26 | H | Cl | Cl | Cl | 2,6-2i-Pr |
| A-27 | H | Cl | Cl | Cl | 3-CF$_3$-4-CN |
| A-28 | H | Cl | Cl | Cl | 2-OCH$_3$-4-NO$_2$ |
| A-29 | H | Cl | Cl | Cl | 2,4-2Cl |
| A-30 | H | Cl | Cl | Cl | 2,6-2Cl |
| A-31 | H | Cl | Cl | Cl | 2,6-2F |
| A-32 | H | Cl | Cl | Cl | 2,5-2Cl |
| A-33 | H | Cl | Cl | Cl | 3,4-2Cl |
| A-34 | H | Cl | Cl | Cl | 3,5-2Cl |
| A-35 | H | Cl | Cl | Cl | 2,3-2Cl |
| A-36 | H | Cl | Cl | Cl | 2-Cl-4-Br |
| A-37 | H | Cl | Cl | Cl | 3-Cl-4-CO$_2$CH$_3$ |
| A-38 | H | Cl | Cl | Cl | 3,4-2CH$_3$ |
| A-39 | H | Cl | Cl | Cl | 3-CF$_3$-4-Cl |
| A-40 | H | Cl | Cl | Cl | 2,4,6-3CH$_3$ |
| A-41 | H | Cl | Cl | Cl | 2,3,4-3F |
| A-42 | H | Cl | Cl | Cl | 2-CN-6-Br-4-NO$_2$ |
| A-43 | H | Cl | Cl | Cl | 2,6-2F-4-NO$_2$ |
| A-44 | H | Cl | Cl | Cl | 2,6-2Cl-4-NO$_2$ |
| A-45 | H | Cl | Cl | Cl | 2,6-2Br-4-NO$_2$ |
| A-46 | H | Cl | Cl | Cl | 2-Br-6-Cl-4-NO$_2$ |
| A-47 | H | Cl | Cl | Cl | 2-CH$_3$-6-Cl-4-NO$_2$ |
| A-48 | H | Cl | Cl | Cl | 2-Cl-6-F-4-NO$_2$ |
| A-49 | H | Cl | Cl | Cl | 2,6-2Cl-4-CF$_3$ |
| A-50 | H | Cl | Cl | Cl | 2-CH$_3$-4-CN-6-CONHCH$_3$ |
| A-51 | H | Cl | Cl | Cl | 2,4-2Cl-6-CONHCH$_3$ |
| A-52 | H | Cl | Cl | Cl | 2,4-2Cl-6-CO$_2$CH$_3$ |
| A-53 | H | Cl | Cl | Cl | 2,4-2Cl-6-CN |

TABLE 18-continued

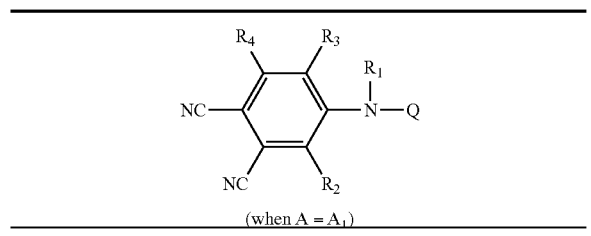

(when A = A₁)

| No. | $R_1$ | $R_2$ | $R_3$ | $R_4$ | $(R_{11})n$ |
|---|---|---|---|---|---|
| A-54 | H | Cl | Cl | Cl | 2,4,6-3Cl |
| A-55 | H | Cl | Cl | Cl | 2,3,4-3Cl |
| A-56 | H | Cl | Cl | Cl | 2,4,5-3Cl |
| A-57 | H | Cl | Cl | Cl | 2,6-2Cl-4-Br |
| A-58 | H | Cl | Cl | Cl | 2,6-2Cl-4-CN |
| A-59 | H | Cl | Cl | Cl | 3,5-2CN-6-Cl |
| A-60 | H | Cl | Cl | Cl | 2,6-2Br-4-OCF₃ |
| A-61 | H | Cl | Cl | Cl | 2-CH₃-3-Cl-4,6-2NO₂ |
| A-62 | H | Cl | Cl | Cl | 2,3,5-3Cl-4,6-2CN |
| A-63 | H | F | F | F | 2-F-4-NO₂ |
| A-64 | H | F | F | F | 2-Cl-4-NO₂ |
| A-65 | H | F | F | F | 2-Cl-5-NO₂ |
| A-66 | H | F | F | F | 2-Cl-4-CF₃ |
| A-67 | H | F | F | F | 2-F-5-CF₃ |
| A-68 | H | F | F | F | 2,4,6-3Cl |
| A-69 | H | F | F | F | 2-CN-6-Br-4-NO₂ |
| A-70 | H | F | F | F | 2,4-2Cl-6-CN |
| A-71 | H | F | F | F | 2,6-2F-4-NO₂ |
| A-72 | H | F | F | F | 2,6-2Cl-4-NO₂ |
| A-73 | H | F | F | F | 2,6-2Cl-4-CN |
| A-74 | H | F | F | F | 2,6-2Br-4-NO₂ |
| A-75 | H | F | F | F | 2-Br-6-Cl-4-NO₂ |
| A-76 | H | F | F | F | 2-CH₃-6-Cl-4-NO₂ |
| A-77 | H | F | F | F | 2-Cl-6-F-4-NO₂ |
| A-78 | H | F | F | F | 2,6-2Cl-4-CF₃ |

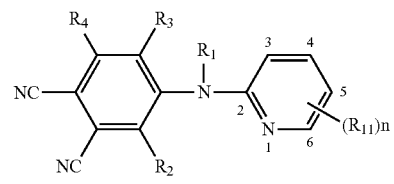

| A-79 | H | Cl | Cl | Cl | 5-Br |
| A-80 | H | Cl | Cl | Cl | 4-CH₃ |
| A-81 | H | Cl | Cl | Cl | 5-CH₃ |
| A-82 | H | Cl | Cl | Cl | 3-Cl-5-CF₃ |
| A-83 | H | Cl | Cl | Cl | 3,5,6-3Cl |

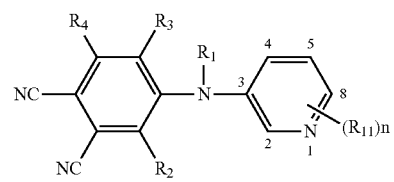

| A-84 | H | Cl | Cl | Cl | — |
| A-85 | H | Cl | Cl | Cl | 2,5-2Cl |

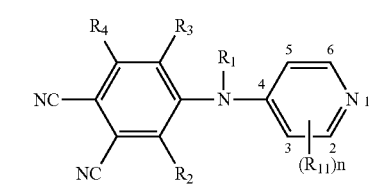

| A-86 | H | Cl | Cl | Cl | — |
| A-87 | H | Cl | Cl | Cl | 3,5-2Cl |
| A-88 | H | F | F | F | 3,5-2Cl |

TABLE 18-continued

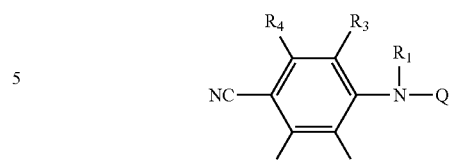

(when A = A₁)

| No. | $R_1$ | $R_2$ | $R_3$ | $R_4$ | $(R_{11})n$ |
|---|---|---|---|---|---|

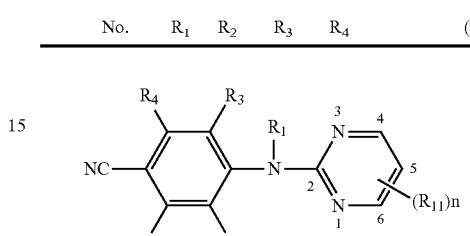

| A-89 | H | Cl | Cl | Cl | — |
| A-90 | H | Cl | Cl | Cl | 4,6-2OCH₃ |

TABLE 19

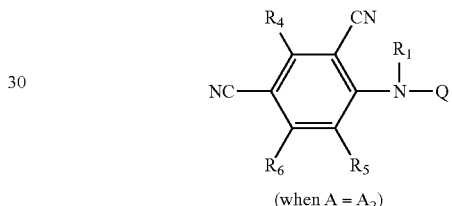

(when A = A₂)

| No. | $R_1$ | $R_5$ | $R_6$ | $R_7$ | $(R_{11})n$ |
|---|---|---|---|---|---|

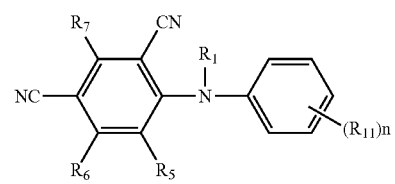

| B-1  | H | Cl | Cl | Cl | 2-CH₃ |
| B-2  | H | Cl | Cl | Cl | 2-Cl |
| B-3  | H | Cl | Cl | Cl | 2-CN |
| B-4  | H | Cl | Cl | Cl | 2-CONHCH₃ |
| B-5  | H | Cl | Cl | Cl | 3-CH₃ |
| B-6  | H | Cl | Cl | Cl | 3-Cl |
| B-7  | H | Cl | Cl | Cl | 3-CF₃ |
| B-8  | H | Cl | Cl | Cl | 3-NO₂ |
| B-9  | H | Cl | Cl | Cl | 4-t-Bu |
| B-10 | H | Cl | Cl | Cl | 4-CN |
| B-11 | H | Cl | Cl | Cl | 4-CF₃ |
| B-12 | H | Cl | Cl | Cl | 4-OCF₃ |
| B-13 | H | Cl | Cl | Cl | 4-CO₂CH₃ |
| B-14 | H | Cl | Cl | Cl | 2,4-2F |
| B-15 | H | Cl | Cl | Cl | 2,6-2F |
| B-16 | H | Cl | Cl | Cl | 2,3-2Cl |
| B-17 | H | Cl | Cl | Cl | 2,6-2Cl |
| B-18 | H | Cl | Cl | Cl | 2,4-2Cl |
| B-19 | H | Cl | Cl | Cl | 3,5-2Cl |
| B-20 | H | Cl | Cl | Cl | 2,5-2Cl |
| B-21 | H | Cl | Cl | Cl | 3,4-2Cl |
| B-22 | H | Cl | Cl | Cl | 2-CH₃-4-Cl |
| B-23 | H | Cl | Cl | Cl | 2-CH₃-6-Cl |
| B-24 | H | Cl | Cl | Cl | 2-CH₃-4-CO₂CH₃ |
| B-25 | H | Cl | Cl | Cl | 2-CH₃-6-CO₂CH₃ |
| B-26 | H | Cl | Cl | Cl | 2,5-2CH₃ |
| B-27 | H | Cl | Cl | Cl | 2,6-2i-Pr |

TABLE 19-continued (when A = A₂)

| No. | R₁ | R₅ | R₆ | R₇ | (R₁₁)n |
|---|---|---|---|---|---|
| B-28 | H | Cl | Cl | Cl | 2-Cl-4-CF₃ |
| B-29 | H | Cl | Cl | Cl | 2-Cl-5-CF₃ |
| B-30 | H | Cl | Cl | Cl | 2-F-5-CF₃ |
| B-31 | H | Cl | Cl | Cl | 2-Cl-5-CF₃ |
| B-32 | H | Cl | Cl | Cl | 2-Cl-4-Br |
| B-33 | H | Cl | Cl | Cl | 3-Cl-4-CO₂CH₃ |
| B-34 | H | Cl | Cl | Cl | 2-F-4-NO₂ |
| B-35 | H | Cl | Cl | Cl | 2-Cl-4-NO₂ |
| B-36 | H | Cl | Cl | Cl | 2-Cl-5-NO₂ |
| B-37 | H | Cl | Cl | Cl | 2,4-2NO₂ |
| B-38 | H | Cl | Cl | Cl | 2-CN-4-NO₂ |
| B-39 | H | Cl | Cl | Cl | 2-NO₂-4-Cl |
| B-40 | H | Cl | Cl | Cl | 3-CF₃-4-CN |
| B-41 | H | Cl | Cl | Cl | 2,3,4-3F |
| B-42 | H | Cl | Cl | Cl | 2,4,6-3Cl |
| B-43 | H | Cl | Cl | Cl | 2,3,4-3Cl |
| B-44 | H | Cl | Cl | Cl | 2,4,6-3CH₃ |
| B-45 | H | Cl | Cl | Cl | 2,4,5-3Cl |
| B-46 | H | Cl | Cl | Cl | 3,4,5-3Cl |
| B-47 | H | Cl | Cl | Cl | 2,6-2Cl-4-Br |
| B-48 | H | Cl | Cl | Cl | 3-CH₃-2,4-2Cl |
| B-49 | H | Cl | Cl | Cl | 2,6-2F-4-NO₂ |
| B-50 | H | Cl | Cl | Cl | 2,4-2Cl-6-CN |
| B-51 | H | Cl | Cl | Cl | 2,6-2Cl-4-CN |
| B-52 | H | Cl | Cl | Cl | 2,5-2Cl-4-CF₃ |
| B-53 | H | Cl | Cl | Cl | 2-Cl-6-F-4-NO₂ |
| B-54 | H | Cl | Cl | Cl | 2,6-2Cl-4-NO₂ |
| B-55 | H | Cl | Cl | Cl | 2-Br-6-Cl-4-NO₂ |
| B-56 | H | Cl | Cl | Cl | 2-Br-6-CN-4-NO₂ |
| B-57 | H | Cl | Cl | Cl | 2,6-2Br-4-NO₂ |
| B-58 | H | Cl | Cl | Cl | 2-CH₃-6-Cl-4-NO₂ |
| B-59 | H | Cl | Cl | Cl | 2-CH₃-4-Cl-6-NO₂ |
| B-60 | H | Cl | Cl | Cl | 2,6-2 C₂H₅-4-Cl |
| B-61 | H | Cl | Cl | Cl | 2,6-2Br-4-OCF₃ |
| B-62 | H | Cl | Cl | Cl | 2,6-2Cl-4-CO₂CH₃ |
| B-62a | H | Cl | Cl | Cl | 2-CH₃-4-CN-6-CONHCH₃ |
| B-62b | H | Cl | Cl | Cl | 2-CH₃-4-Cl-6-CONHCH₃ |
| B-63 | H | Cl | Cl | Cl | 2,6-2Cl-4-CONHPh |
| B-64 | H | Cl | Cl | Cl | 2,6-2Cl-4-CONH(4-Cl—Ph) |
| B-65 | H | Cl | Cl | Cl | 2,6-2Cl-4-CO₂Na |
| B-66 | H | Cl | Cl | Cl | 2,6-2Cl-4-COOH |
| B-67 | H | Cl | Cl | Cl | 2,6-2NO₂-3-Cl-4-CF₃ |
| B-68 | H | Cl | Cl | Cl | 2-CH₃-3-Cl-4,6-2NO₂ |
| B-69 | H | Cl | Cl | Cl | 2,3,5-3Cl-4,6-2CN |
| B-70 | H | Cl | N(C₂H₅)₂ | Cl | 2-NO₂ |
| B-71 | H | Cl | NHCH₃ | NHCH₃ | 2-F |
| B-72 | H | Cl | OCH₃ | OCH₃ | 2-Br |
| B-73 | H | Cl | N(CH₃)₂ | Cl | 2,6-2Cl-4-NO₂ |
| B-74 | H | Cl | OCH₃ | Cl | 2,6-2Cl-4-NO₂ |
| B-75 | H | Cl | OCH₃ | OCH₃ | 2,6-2Cl-4-NO₂ |
| B-76 | H | F | F | F | 2-CH₃ |
| B-77 | H | F | F | F | 2-NO₂ |
| B-78 | H | F | F | F | 3-CH₃ |
| B-79 | H | F | F | F | 3-Cl |
| B-80 | H | F | F | F | 3-NO₂ |
| B-81 | H | F | F | F | 4-OCF₃ |
| B-82 | H | F | F | F | 4-CN |
| B_83 | H | F | F | F | 2,3-2Cl |
| B-84 | H | F | F | F | 2,5-2Cl |
| B-85 | H | F | F | F | 3,5-2Cl |
| B-86 | H | F | F | F | 2,6-2Cl |
| B-87 | H | F | F | F | 2,4-2NO₂ |
| B-88 | H | F | F | F | 2-Cl-4-Br |
| B-89 | H | F | F | F | 2-CH₃-4-Cl |
| B-90 | H | F | F | F | 2-CH₃-6-Cl |
| B-91 | H | F | F | F | 2-Me-4-NO₂ |
| B-92 | H | F | F | F | 2-Cl-4-CF₃ |
| B-93 | H | F | F | F | 2-F-5-CF₃ |
| B-94 | H | F | F | F | 2-Cl-5-CF₃ |
| B-95 | H | F | F | F | 2-Cl-4-NO₂ |
| B-96 | H | F | F | F | 2-NO₂-4-Cl |
| B-97 | H | F | F | F | 3-CF₃-4-CN |
| B-98 | H | F | F | F | 3-CF₃-4-Cl |
| B-99 | H | F | F | F | 3-Cl-4-CO₂CH₃ |
| B-100 | H | F | F | F | 2,4,6-3CH₃ |
| B-101 | H | F | F | F | 2,3,4-3F |
| B-102 | H | F | F | F | 2,3,4-3Cl |
| B-103 | H | F | F | F | 2,4,6-3Cl |
| B-104 | H | F | F | F | 2,4,5-3Cl |
| B-105 | H | F | F | F | 3,4,5-3Cl |
| B-106 | H | F | F | F | 2,6-2Cl-4-Br |
| B-107 | H | F | F | F | 2,4-2Cl-6-CN |
| B-108 | H | F | F | F | 2,6-2Cl-4-CN |
| B-109 | H | F | F | F | 2,6-2Cl-4-NO₂ |
| B-110 | H | F | F | F | 2,6-2F-4-NO₂ |
| B-111 | H | F | F | F | 2,6-2Cl-4-CF₃ |
| B-112 | H | F | F | F | 2-Cl-6-F-4-NO₂ |
| B-113 | H | F | F | F | 2-Br-6-Cl-4-NO₂ |
| B-114 | H | F | F | F | 2-CH₃-6-Cl-4-NO₂ |
| B-115 | H | F | F | F | 2,6-2Br-4-NO₂ |
| B-116 | H | F | F | F | 2-Br-6-CN-4-NO₂ |
| B-117 | H | F | F | F | 2,6-2Br-4-OCF₃ |
| B-118 | H | F | F | F | 2-CH₃-3-Cl-4,6-2NO₂ |
| B-119 | H | F | F | F | 2,3,5-3Cl-4,6-2CN |

| No. | R₁ | R₅ | R₆ | R₇ | (R₁₁)n |
|---|---|---|---|---|---|
| B-120 | H | Cl | Cl | Cl | — |
| B-121 | H | Cl | Cl | Cl | 3-Br |
| B-122 | H | Cl | Cl | Cl | 5-Br |
| B-123 | H | Cl | Cl | Cl | 3-Br-4-CH₃ |
| B-124 | H | Cl | Cl | Cl | 3-Br-5-CH₃ |
| B-125 | H | Cl | Cl | Cl | 3-Cl-5-CF₃ |
| B-126 | H | F | F | F | 3-Cl-5-CF₃ |
| B-127 | H | Cl | Cl | Cl | 3,5-2CN-6-Cl |
| B-128 | H | Cl | Cl | Cl | 3,5,6-3Cl |
| B-128b | H | Cl | Cl | Cl | 3,4,5,6-4Cl |
| B-129 | H | F | F | F | 3,5,6-3Cl |
| B-130 | H | Cl | Cl | Cl | — |
| B-131 | H | Cl | Cl | Cl | 2-Cl |
| B-132 | H | Cl | Cl | Cl | 6-Br |
| B-133 | H | Cl | Cl | Cl | 2,5-2Cl |
| B-134 | H | F | F | F | 2,5-2Cl |
| B-135 | H | Cl | Cl | Cl | 2-Cl-4-CH₃ |

TABLE 19-continued

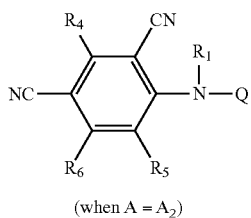

(when A = A₂)

| No. | R₁ | R₅ | R₆ | R₇ | (R₁₁)n |
|---|---|---|---|---|---|

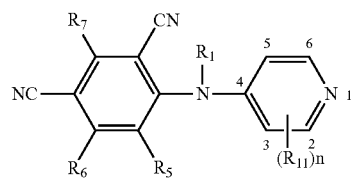

| B-136 | H | Cl | Cl | Cl | — |
| B-137 | H | Cl | Cl | Cl | 2-Cl |
| B-138 | H | Cl | Cl | Cl | 3-Br |
| B-139 | H | Cl | Cl | Cl | 3,5-2Cl |
| B-140 | H | F | F | F | 3,5-2Cl |
| B-140b | H | Cl | Cl | Cl | 2,3,5,6-4Cl |

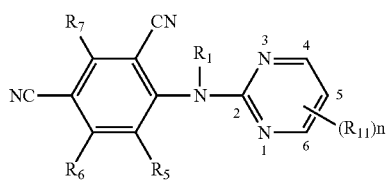

| B-141 | H | Cl | Cl | Cl | — |
| B-142 | H | Cl | Cl | Cl | 4,6-2CH₃ |
| B-143 | H | Cl | Cl | Cl | 4,6-2OCH₃ |
| B-144 | H | Cl | Cl | Cl | 4-CF₃-5-CO₂C₂H₅ |

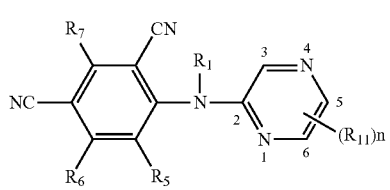

| B-145 | H | Cl | Cl | Cl | — |
| B-146 | H | Cl | Cl | Cl | 6-Cl |
| B-147 | H | F | F | F | 6-Cl |

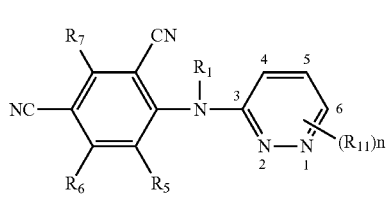

| B-148 | H | Cl | Cl | Cl | — |
| B-149 | H | Cl | Cl | Cl | 6-Cl |
| B-150 | H | F | F | F | 6-Cl |

TABLE 20

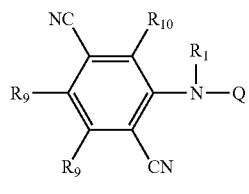

(when A = A₃)

| No. | R₁ | R₈ | R₉ | R₁₀ | (R₁₁)n |
|---|---|---|---|---|---|

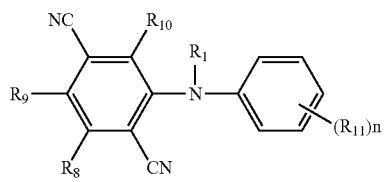

| C-1 | H | Cl | Cl | Cl | 2-CH₃ |
| C-2 | H | Cl | Cl | Cl | 2-Cl |
| C-3 | H | Cl | Cl | Cl | 2-NO₂ |
| C-4 | H | Cl | Cl | Cl | 2-CONHCH₃ |
| C-5 | H | Cl | Cl | Cl | 3-Cl |
| C-6 | H | Cl | Cl | Cl | 3-CH₃ |
| C-7 | H | Cl | Cl | Cl | 3-NO₂ |
| C-8 | H | Cl | Cl | Cl | 4-CO₂CH₃ |
| C-9 | H | Cl | Cl | Cl | 4-t-Bu |
| C-10 | H | Cl | Cl | Cl | 4-CH₃ |
| C-11 | H | Cl | Cl | Cl | 4-CF₃ |
| C-12 | H | Cl | Cl | Cl | 4-CN |
| C-13 | H | Cl | Cl | Cl | 4-OCF₃ |
| C-14 | H | Cl | Cl | Cl | 4-OCH₃ |
| C-15 | H | Cl | Cl | Cl | 2,4-2Cl |
| C-16 | H | Cl | Cl | Cl | 2,6-2Cl |
| C-17 | H | Cl | Cl | Cl | 2,6-2F |
| C-18 | H | Cl | Cl | Cl | 2,5-2Cl |
| C-19 | H | Cl | Cl | Cl | 3,4-2Cl |
| C-20 | H | Cl | Cl | Cl | 3,5-2Cl |
| C-21 | H | Cl | Cl | Cl | 2,3-2Cl |
| C-22 | H | Cl | Cl | Cl | 2-Cl-4-Br |
| C-23 | H | Cl | Cl | Cl | 2,4-2NO₂ |
| C-24 | H | Cl | Cl | Cl | 2,6-2i-Pr |
| C-25 | H | Cl | Cl | Cl | 2-CH₃-4-Cl |
| C-26 | H | Cl | Cl | Cl | 2-CH₃-6-Cl |
| C-27 | H | Cl | Cl | Cl | 2-F-4-NO₂ |
| C-28 | H | Cl | Cl | Cl | 2-Cl-4-NO₂ |
| C-29 | H | Cl | Cl | Cl | 2-Cl-5-NO₂ |
| C-30 | H | Cl | Cl | Cl | 2-Cl-4-CF₃ |
| C-31 | H | Cl | Cl | Cl | 2-F-5-CF₃ |
| C-32 | H | Cl | Cl | Cl | 2-Cl-5-CF₃ |
| C-33 | H | Cl | Cl | Cl | 2-NO₂-4-Cl |
| C-34 | H | Cl | Cl | Cl | 2-CH₃-6-CO₂CH₃ |
| C-35 | H | Cl | Cl | Cl | 2-OCH₃-4-NO₂ |
| C-36 | H | Cl | Cl | Cl | 3-Cl-4-CO₂CH₃ |
| C-37 | H | Cl | Cl | Cl | 3,4-2CH₃ |
| C-38 | H | Cl | Cl | Cl | 3-CF₃-4-CN |
| C-39 | H | Cl | Cl | Cl | 3-CF₃-4-Cl |
| C-40 | H | Cl | Cl | Cl | 2,6-2Cl-4-NO₂ |
| C-41 | H | Cl | Cl | Cl | 2,6-2Br-4-NO₂ |
| C-42 | H | Cl | Cl | Cl | 2,6-2Cl-4-Br |
| C-43 | H | Cl | Cl | Cl | 2,6-2Cl-4-CN |
| C-44 | H | Cl | Cl | Cl | 2,4-2Cl-6-CN |
| C-45 | H | Cl | Cl | Cl | 2,6-2F-4-NO₂ |
| C-46 | H | Cl | Cl | Cl | 2-Cl-6-F-4-NO₂ |
| C-47 | H | Cl | Cl | Cl | 2,6-2Br-4-OCF₃ |
| C-48 | H | Cl | Cl | Cl | 2-CN-6-Br-4-NO₂ |
| C-49 | H | Cl | Cl | Cl | 2-Br-6-Cl-4-NO₂ |
| C-50 | H | Cl | Cl | Cl | 2,6-2Cl-4-CF₃ |
| C-51 | H | Cl | Cl | Cl | 2,3,4-3F |
| C-52 | H | Cl | Cl | Cl | 2,4,5-3Cl |
| C-53 | H | Cl | Cl | Cl | 2,4,6-3Cl |
| C-54 | H | Cl | Cl | Cl | 2,3,4-3Cl |
| C-55 | H | Cl | Cl | Cl | 2,4,6-3CH₃ |
| C-56 | H | Cl | Cl | Cl | 2-CH₃-4-Cl-6-CONHCH₃ |
| C-57 | H | Cl | Cl | Cl | 2-CH₃-6-Cl-4-NO₂ |

TABLE 20-continued

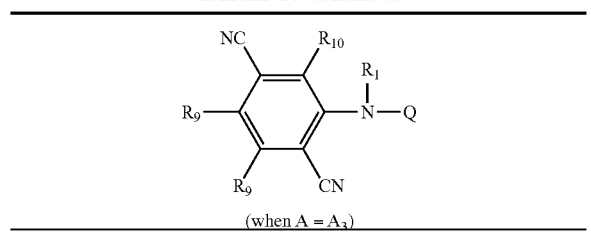

(when A = A₃)

| No. | $R_1$ | $R_8$ | $R_9$ | $R_{10}$ | $(R_{11})n$ |
|---|---|---|---|---|---|
| C-58 | H | Cl | Cl | Cl | 2,4-2Cl-6-CONHCH₃ |
| C-59 | H | Cl | Cl | Cl | 2,4-2Cl-6-CO₂CH₃ |
| C-60 | H | Cl | Cl | Cl | 2-CH₃-3-Cl-4,6-2NO₂ |
| C-61 | H | Cl | Cl | Cl | 2,3,5-3Cl-4,6-2CN |
| C-62 | H | OCH₃ | Cl | Cl | 2-Cl-4-CF₃ |
| C-63 | H | F | F | F | 2-CH₃ |
| C-64 | H | F | F | F | 2-NO₂ |
| C-65 | H | F | F | F | 3-CH₃ |
| C-66 | H | F | F | F | 3-Cl |
| C-67 | H | F | F | F | 3-NO₂ |
| C-68 | H | F | F | F | 4-OCH₃ |
| C-69 | H | F | F | F | 4-t-Bu |
| C-70 | H | F | F | F | 4-NO₂ |
| C-71 | H | F | F | F | 2,4-2Cl |
| C-72 | H | F | F | F | 2,6-2Cl |
| C-73 | H | F | F | F | 2,6-2F |
| C-74 | H | F | F | F | 2,5-2Cl |
| C-75 | H | F | F | F | 3,4-2Cl |
| C-76 | H | F | F | F | 3,5-2Cl |
| C-77 | H | F | F | F | 2,3-2Cl |
| C-78 | H | F | F | F | 2-Cl-4-Br |
| C-79 | H | F | F | F | 2-F-4-NO₂ |
| C-80 | H | F | F | F | 2-Cl-4-NO₂ |
| C-81 | H | F | F | F | 2-Cl-5-NO₂ |
| C-82 | H | F | F | F | 2-Cl-4-CF₃ |
| C-83 | H | F | F | F | 2-Cl-5-CF₃ |
| C-84 | H | F | F | F | 2-F-5-CF₃ |
| C-85 | H | F | F | F | 2-CH₃-4-Cl |
| C-86 | H | F | F | F | 2-CH₃-4-NO₂ |
| C-87 | H | F | F | F | 2-CH₃-6-Cl |
| C-88 | H | F | F | F | 2-OCH₃-4-NO₂ |
| C-89 | H | F | F | F | 2-NO₂-4-Cl |
| C-90 | H | F | F | F | 3-Cl-4-CO₂CH₃ |
| C-91 | H | F | F | F | 3-CF₃-4-Cl |
| C-92 | H | F | F | F | 2,6-2F-4-NO₂ |
| C-93 | H | F | F | F | 2,6-2Cl-4-NO₂ |
| C-94 | H | F | F | F | 2,6-2Cl-4-CN |
| C-95 | H | F | F | F | 2,4-2Cl-6-CN |
| C-96 | H | F | F | F | 2,6-2Br-4-NO₂ |
| C-97 | H | F | F | F | 2-CN-6-Br-4-NO₂ |
| C-98 | H | F | F | F | 2,6-2Cl-4-CF₃ |
| C-99 | H | F | F | F | 2-Br-6-Cl-4-NO₂ |
| C-100 | H | F | F | F | 2-Cl-6-F-4-NO₂ |
| C-101 | H | F | F | F | 2-CH₃-6-Cl-4-NO₂ |
| C-102 | H | F | F | F | 2,6-2Br-4-OCF₃ |
| C-103 | H | F | F | F | 2,4,6-3Cl |
| C-104 | H | F | F | F | 2,3,4-3Cl |
| C-105 | H | F | F | F | 2,4,5-3Cl |
| C-106 | H | F | F | F | 2,6-2Cl-4-Br |
| C-107 | H | F | F | F | 2,4,6-3CH₃ |

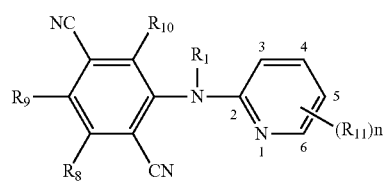

| No. | $R_1$ | $R_8$ | $R_9$ | $R_{10}$ | $(R_{11})n$ |
|---|---|---|---|---|---|
| C-108 | H | F | F | F | 5-Br |
| C-109 | H | Cl | Cl | Cl | 5-Br |
| C-110 | H | Cl | Cl | Cl | 4-CH₃ |
| C-111 | H | Cl | Cl | Cl | 5-CH₃ |
| C-112 | H | Cl | Cl | Cl | 3-Cl-5-CF₃ |
| C-113 | H | Cl | Cl | Cl | 3,5,6-3Cl |
| C-114 | H | Cl | Cl | Cl | 3,5-2CN-6-Cl |

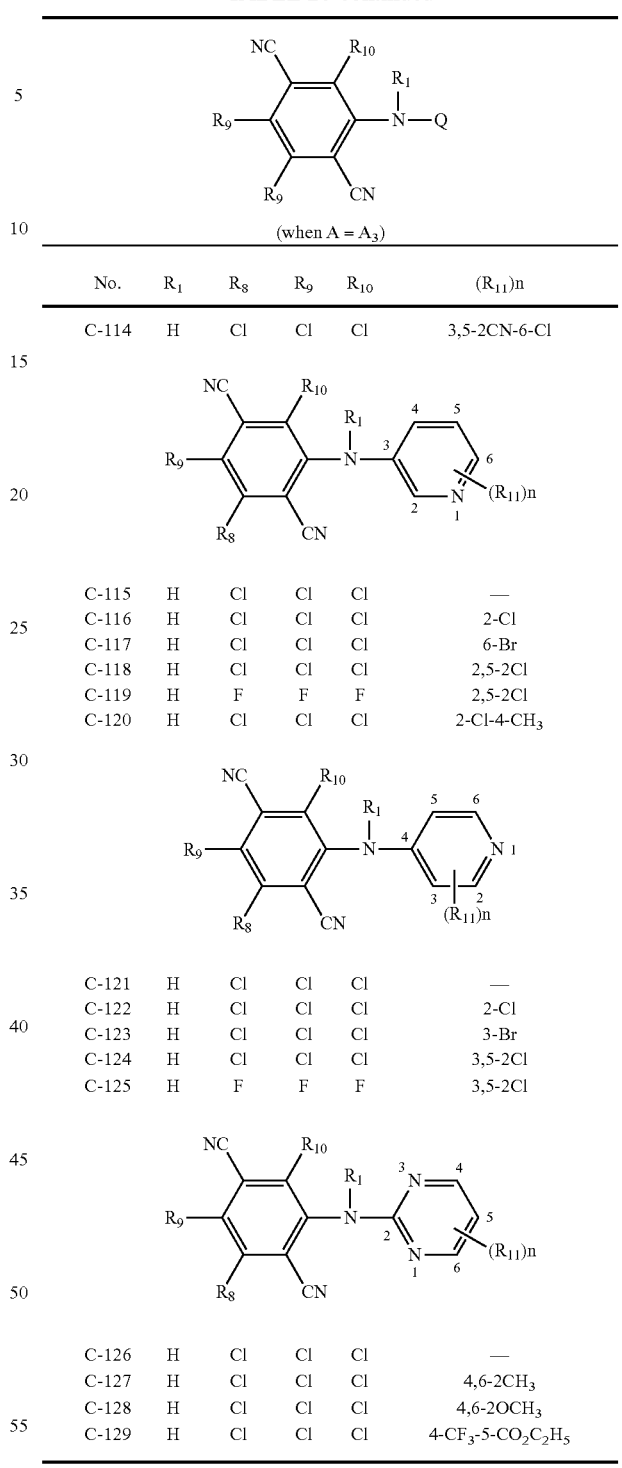

| No. | $R_1$ | $R_8$ | $R_9$ | $R_{10}$ | $(R_{11})n$ |
|---|---|---|---|---|---|
| C-115 | H | Cl | Cl | Cl | — |
| C-116 | H | Cl | Cl | Cl | 2-Cl |
| C-117 | H | Cl | Cl | Cl | 6-Br |
| C-118 | H | Cl | Cl | Cl | 2,5-2Cl |
| C-119 | H | F | F | F | 2,5-2Cl |
| C-120 | H | Cl | Cl | Cl | 2-Cl-4-CH₃ |
| C-121 | H | Cl | Cl | Cl | — |
| C-122 | H | Cl | Cl | Cl | 2-Cl |
| C-123 | H | Cl | Cl | Cl | 3-Br |
| C-124 | H | Cl | Cl | Cl | 3,5-2Cl |
| C-125 | H | F | F | F | 3,5-2Cl |
| C-126 | H | Cl | Cl | Cl | — |
| C-127 | H | Cl | Cl | Cl | 4,6-2CH₃ |
| C-128 | H | Cl | Cl | Cl | 4,6-2OCH₃ |
| C-129 | H | Cl | Cl | Cl | 4-CF₃-5-CO₂C₂H₅ |

The compounds having general formula (I) of the invention can be prepared according to the following schemes, the definitions of substituents are as defined above:

The compounds I-a ($R_1$=H) represented by general formula I were prepared by reaction of intermediate A-X containing halo or amino with intermediate Y-Q containing amino or halo under basic conditions; followed by reacting with Z—$R_1$ ($R_1 \neq$H) to obtain compounds I-b ($R_1 \neq$H) having general formula I.

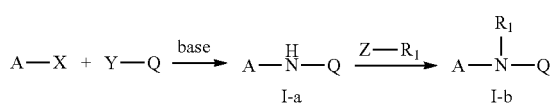

Wherein when X is halo, Y is $NH_2$, when X is $NH_2$, Y is halo; Z is selected from alkali or H.

The preferred compounds having general formula I-1, I-2, I-3 of the present invention, considering easily available raw materials and simple synthesis method, can be prepared according to the following schemes, the definitions of substituents are as defined above:

When A=$A_1$, the compounds of general formula I-1 ($R_1$=H; $R_2$, $R_3$, $R_4$ are Cl) can be obtained by reaction of intermediates II and III under basic condition.

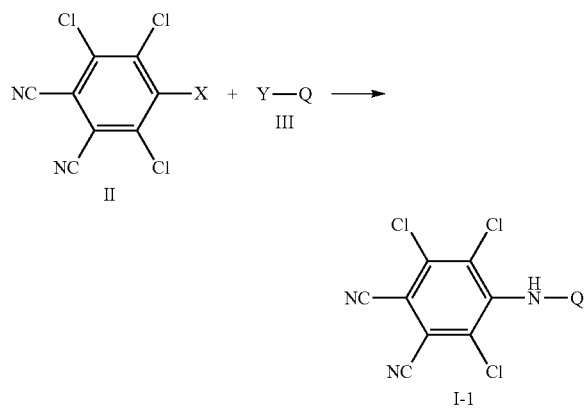

Wherein when X is Cl, Y is $NH_2$, when X is $NH_2$, Y is halo.

When A=$A_2$, the compounds of general formula I-2 ($R_1$=H) can be obtained by reaction of intermediates IV and III under basic condition.

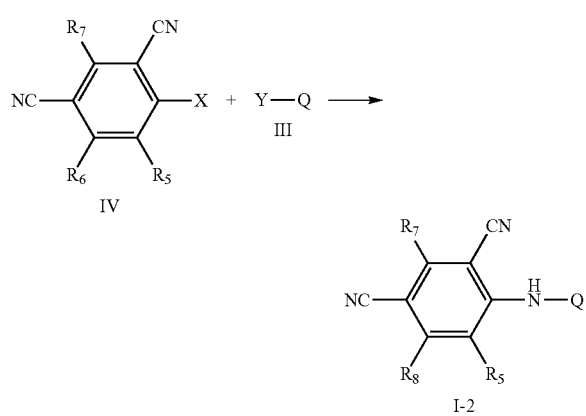

Wherein when $R_5$, $R_6$ and $R_7$ are F, then X is F, Y is $NH_2$; when $R_5$, $R_6$ and $R_7$ are Cl, then X is Cl, Y is $NH_2$; when X is $NH_2$, then Y is halo.

When A=$A_3$, the compounds of general formula I-3 ($R_1$=H) can be obtained by reaction of intermediates V and III under basic condition.

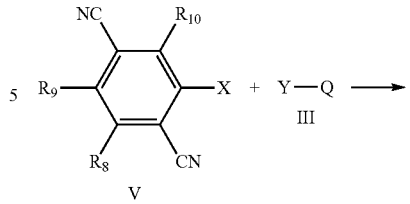

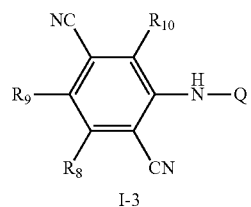

Wherein when $R_8$, $R_9$ and $R_{10}$ are F, then X is F, Y is $NH_2$; when $R_8$, $R_9$ and $R_{10}$ are Cl, then X is Cl, Y is $NH_2$; when X is $NH_2$, then Y is halo.

The proper base mentioned may be selected from potassium hydroxide, sodium hydroxide, sodium carbonate, potassium carbonate, sodium bicarbonate, triethylamine, pyridine, sodium methoxide, sodium ethoxide, sodium hydride, potassium tert-butoxide or sodium tert-butoxide and so on.

The reaction was carried out in proper solvent and the proper solvent mentioned may be selected from tetrahydrofuran, 1,4-dioxane, acetonitrile, toluene, xylene, benzene, DMF, N-methyl pyrrolidone, DMSO, acetone or butanone and so on.

The proper temperature mentioned is from room temperature to boiling point of the solvent, normal temperature is from 20 to 100° C.

The reaction time is in the range of 30 minutes to 20 hours, generally being 1-10 hours.

Intermediates II, when X is Cl, are commercially available; when X is $NH_2$, can be prepared according to the method described in Pesticide Science (1988), 24(2), 116-117.

Intermediates IV, when X is F or Cl, are commercially available; when X is $NH_2$, can be prepared according to the method described in Pesticide Science (1988), 24(2), 116-117.

Intermediates V, when X is F or Cl, are commercially available; when X is $NH_2$, can be prepared according to the method described in Pesticide Science (1988), 24(2), 116-117.

Intermediates III, are mostly commercially available, while other intermediates unavailable in the market can be synthesized starting from the raw materials with commercial availability via substituent change according to common methods; and also can be prepared according to the known methods, such as Indian Journal of Chemistry, Section B: Organic Chemistry Including Medicinal Chemistry, 45B(4), 972-975; 2006, Tetrahedron Letters, 44(21), 4085-4088; 2003 or Polish PL174903.

In general formula I-1, I-2, I-3, when Q is phenyl, the compounds in which at least one of $R_4$, $R_6$ or $R_8$ is H, can add one or two $NO_2$ groups to these compounds of general formula I.

The halogenation of substituted diphenylamine compounds of general formula I, in which $R_4$, $R_6$ or $R_8$ is not halogen atom, can add one or two halogen atoms to these compounds of general formula I.

The compounds of general formula I, in which $R_2$ is alkylamino, alkoxy or alkylthio and so on, can be prepared from the reaction of compounds of general formula I whose $R_2$ is halogen atom with amine, alcohol or mercaptan (or their salts).

In general formula I-1, I-2, I-3, when Q is phenyl, the compounds with one or two $NO_2$ groups at any three substituted positions (two-ortho and one para-positions) can be obtained from nitration of compounds containing at least one hydrogen atom on these three substituted positions. The preparation method was described in U.S. Pat. No. 4,041,172; the preparation of compounds containing from one to three halogen atoms with general formula I-1, I-2 and I-3 can be completed via the halogenations of compounds containing at least one hydrogen atom on these three substituted positions (two-ortho and one para-positions) by adding one or two halogen atoms.

The salts of compounds having general formula I can be prepared by the reaction of the compounds of general formula I with corresponding acid or alkali according to routine methods. The proper acid may be selected from hydrochloric acid, sulfuric acid, phosphoric acid, formic acid, acetic acid, trifluoroacetic acid, methylsulfonic acid, p-toluenesulfonic acid, malic acid, citric acid, etc; the preferred acid may be hydrochloric acid, sulfuric acid, phosphoric acid, trifluoroacetic acid, methylsulfonic acid, p-toluenesulfonic acid, acetic acid. The proper base may be selected from sodium hydride, potassium hydroxide, sodium hydroxide.

Although the compounds having general formula I of the present invention and some compounds reported in the prior art are all diphenylamine compounds, there are significant differences between their structural characteristics. And because of the structural differences, the compounds of the present invention show unexpected fungicidal activity. When Q is phenyl, in which there are two or three substitutents on o- or p-positions, these compounds have much better fungicidal activity; particularly, when the substituent on p-position is electron with-drawing group, the compounds show outstanding fungicidal activity. Meanwhile, the raw materials to prepare these compounds are easily available and the methods are simple and convenient, therefore the compounds of the present invention have lower costs and broader application prospect compared with known fungicides.

The compounds of general formula I show excellent activity against many plant pathogens/diseases in agricultural and other fields. Therefore the technical scheme of the present invention also includes the uses of the compounds having general formula I or their salts to prepare fungicides in agricultural and other fields.

The present invention is explained by the following examples of plant disease, but without being restricted thereby.

The compounds of general formula I can be used to control these plant diseases: Oomycete diseases, such as downy mildew (cucumber downy mildew, rape downy mildew, soybean downy mildew, downy mildew of beet, downy mildew of sugarcane, tobacco downy mildew, pea downy mildew, vegetable sponge downy mildew, chinese wax gourd downy mildew, muskmelon downy mildew, chinese cabbage downy mildew, spinach downy mildew, radish downy mildew, grape downy mildew, onion downy mildew), white rust (rape white rust, chinese cabbage white rust), damping-off disease (rape damping-off, tobacco damping-off, tomato damping-off, pepper damping-off, eggplant damping-off, cucumber damping-off, cotton damping-off), pythium rot (pepper soft stale disease, vegetable sponge cottony leak, chinese wax gourd cottony leak), blight (broad bean phytophthora blight, cucumber phytophthora blight, pumpkin phytophthora rot, chinese wax gourd phytophthora blight, watermelon phytophthora blight, muskmelon phytophthora blight, pepper phytophthora blight, chinese chives phytophthora blight, carlic phytophthora blight, cotton phytophthora blight), late blight (potato late blight, tomato late blight) and so on; diseases caused by Deuteromycotina, such as wilt disease (sweet potato fusarium wilt, cotton fusarium wilt disease, sesame wilt disease, fusarium wilt disease of costarbean, tomato fusarium wilt, bean fusarium wilt, cucumber fusarium wilt, vegetable sponge fusarium wilt, pumpkin fusarium wilt, chinese wax gourd fusarium wilt, watermelon fusarium wilt, muskmelon fusarium wilt, pepper fusarium wilt, broad bean fusarium wilt, fusarium wilt disease of rape, fusarium wilt disease of soybean), root rot (pepper root rot, eggplant root rot, bean fusarium root-rot, cucumber fusarium root rot, balsam pear fusarium root rot, cotton black root rot, broad bean thielaviopsis root rot), drooping disease (cotton soreshin, sesame soreshin, pepper rhizoctonia rot, cucumber rhizoctonia rot, chinese cabbage rhizoctonia rot), anthracnose (sorghum anthracnose, cotton anthracnose, kenaf anthracnose, jute anthracnose, flax anthracnose, tobacco anthracnose, mulberry anthracnose, pepper anthracnose, eggplant anthracnose, bean anthracnose, cucumber anthracnose, balsam pear anthracnose, summer squash anthracnose, chinese wax gourd anthracnose, watermelon anthracnose, muskmelon anthracnose, litchi anthracnose), verticillium wilt (cotton verticillium wilt, verticillium wilt of sunflower, tomato verticillium wilt, pepper verticillium wilt, eggplant verticillium wilt), scab (summer squash scab, chinese wax gourd scab, muskmelon scab), gray mold (cotton boll gray mold, kenaf gray mold, tomato gray mold, pepper gray mold, bean gray mold, celery gray mold, spinach gray mold, kiwi fruit gray mold rot), brown spot (cotton brown spot, jute brown spot, beet sercospora leaf spot, peanut brown spot, pepper brown leaf spot, chinese wax gourd corynespora leaf spot, soybean brown spot, sunflower brown spot, pea ascochyta blight, broad bean brown spot), black spot (flax black spot, rape alternaria leaf spot, sesame black spot, sunflower alternaria leaf spot, costarbean alternaria leaf spot, tomato nail head spot, pepper black fruit spot, eggplant black spot, bean leaf spot, cucumber alternaria blight, celery alternaria black leaf spot, carrot alternaria black rot, carrot leaf blight, apple alternaria rot, peanut brown spot), spot blight (tomato septoria leaf spot, pepper septoria leaf spot, celery late blight), early blight (tomato early blight, pepper early blight, eggplant early blight, potato early blight, celery early blight), ring spot (soybean zonate spot, sesame ring spot, bean zonate spot), leaf blight (sesame leaf blight, sunflower leaf blight, watermelon alternaria blight, muskmelon alternaria spot), basal stem rot (tomato basal stem rot, bean rhizoctonia rot), and others (corn northern leaf spot, kenaf damping-off, rice blast, millet black sheath, sugarcane eye spot, cotton aspergillus boll rot, peanut crown rot, soybean stem blight, soybean black spot, muskmelon alternaria leaf blight, peanut web blotch, tea red leaf spot, pepper phyllosticta blight, chinese wax gourd phyllosticta leaf spot, celery black rot, spinach heart rot, kenaf leaf mold, kenaf brown leaf spot, Jute stem blight, soybean cercospora spot, sesame leaf spot, costarbean gray leaf spot, tea brown leaf spot, eggplant cercospora leaf spot, bean cercospora leaf spot, balsam pear cercospora leaf spot, watermelon cercospora leaf spot, jute dry rot, sunflower root and stem rot, bean charcoal rot, soybean target spot, eggplant corynespora leaf spot, cucumber corynespora target leaf spot, tomato leaf mold, eggplant fulvia leaf mold, broad bean chocolate spot) and so on; diseases caused by Basidiomycete, such as rust (wheat stripe rust, wheat stem rust, wheat leaf rust, peanut rust, sunflower rust, sugarcane rust, chinese chives rust, onion rust, millet rust, soybean rust), smut (corn head smut, corn smut, sorghum silk smut, sorghum loose kernel smut, sorghum hard smut, sorghum smut, millet kernel smut, sugarcane smut, bean rust), and others (for example, wheat sheath blight and rice sheath blight) and so on; diseases caused by Ascomycete, such as powdery mildew (wheat powdery mildew, rape powdery mildew, powdery mildew of sesame, powdery mildew of sunflower, beet powdery mildew, eggplant powdery mildew, pea powdery mildew, vegetable sponge powdery mildew, pumpkin powdery mildew, summer squash powdery mildew, chinese wax gourd, muskmelon powdery mildew, grape powdery mildew, broad bean powdery mildew), sclerotinia rot (flax sclertiniose, rape sclertiniose, soybean sclertiniose, peanut sclertiniose, tobacco sclerotinia rot, pepper sclerotinia rot, eggplant sclerotinia rot, bean sclerotinia rot, pea sclerotinia rot, cucumber sclerotinia rot, balsam pear sclerotinia rot, chinese wax gourd sclerotinia rot, watermelon sclerotinia disease, celery stem rot), scab (apple scab, pear scab) and so on. Especially, the compounds of the present invention exhibit very good control against corn southern rust, rice blast, cucumber gray mold and cucumber downy mildew at very low doses.

Thanks to their positive characteristics, the compounds mentioned above can be advantageously used in protecting crops of farming and gardening, domestic and breeding animals, as well as environments frequented by human beings, from pathogens.

In order to obtain desired effect, the dosage of the compound to be applied can vary with various factors, for example, the used compound, the protected crop, the type of harmful organism, the degree of infestation, the climatic conditions, the application method and the adopted formulation.

The dosage of compounds in the range of 10 g to 5 kg per hectare can provide a sufficient control.

Another object of the present invention also relates to a method for controlling phytopathogenic fungi in crops of farming and gardening and/or on domestic and breeding animals and/or environments frequented by human beings, by application of the compounds having general formula I. In particular, the dosage of compounds to be applied varies from 10 g to 5 kg per hectare.

For practical application in agriculture, it is usually beneficial to use compositions containing one or more compounds of general formula I.

Therefore, a further technical scheme of the present invention relates to fungicidal compositions containing compounds having general formula I as active ingredient and acceptable carrier in agriculture, the weight percentage of the active ingredient in the compositions is 0.5-90%.

Compositions can be used in the form of dry powders, wettable powders, aqueous emulsion, emulsifiable concentrates, microemulsions, pastes, granulates, solutions, suspensions, etc. The selection of the type of compositions depends on the specific application.

The compositions are prepared in the known method, for example by diluting or dissolving the active substance with a solvent medium and/or a solid diluent, optionally in the presence of surface-active agents. Solid diluents or carriers which can be used are, for example: silica, kaolin, bentonite, talc, diatomite, dolomite, calcium carbonate, magnesia, chalk, clays, synthetic silicates, attapulgite, sepiolite. Liquid diluents which can be used are, for example, besides water, aromatic organic solvents (xylols or mixtures of alkylbenzols, chlorobenzene, etc.), paraffins (petroleum fractions), alcohols (methanol, propanol, butanol, octanol, glycerin, etc.), esters (ethyl acetate, isobutyl acetate, etc.), ketones (cyclohexanone, acetone, acetophenone, isophorone, ethylamylketone, etc.), amides (N, N-dimethylformamide, N-methylpyrrolidone, etc.). Surface-active agents which can be used are salts of sodium, calcium, triethylamine or triethanolamine of alkylsulfonates, alkylarylsulfonates, polyethoxylated alkylphenols, polyethoxylated esters of sorbitol, ligninsulfonates, etc. The compositions can also contain special additives for particular purposes, for example adhesion agents such as Arabic gum, polyvinyl alcohol, polyvinyl-pyrrolidone, etc.

The concentration of active ingredient in the above compositions can vary within a wide range depending on the active compound, the applications for which they are destined, the environmental conditions and the type of adopted formulation. In general the concentration of active ingredient ranges from 1% to 90%, preferably from 5% to 50%.

If required, other active ingredients being compatible with the compounds having general formula I can be added to the compositions, such as, other acaricides/insecticides, fungicides, plant growth regulators, antibiotics, herbicides, fertilizers.

The preparation methods of several common formulation examples in the present invention are as follows:

The preparation of suspension concentrate: the common active component in formula is 5%-35%. With water as the medium, the compound in the invention, dispersing agent, suspending agent and antifreeze are added to sanding machine for grinding to make suspension concentrate.

The preparation of water emulsion: the compound in the invention, solvent and emulsifier are mixed together to make a homogeneous oil phase. The water is mixed with antifreeze to make a homogeneous aqueous phase. In the high-speed stirring, the aqueous phase is added to the oil phase or oil phase is added to the aqueous phase, forming the water emulsion with good dispersity. The active component of water emulsions is generally 5%-15% in this invention. For the production of concentrated emulsions, the compounds of this invention are dissolved in one or more of the mixed solvent, and then emulsifier was added to enhance dispersion effects in the water.

The preparation of wettable powder: according to formulation requirements, the compound in the invention, surfactants and solid diluents are mixed well, after smashing through ultrafine pulverizer, that is the wettable powder products (for example, 10%-40%). To prepare the spraying wettable powder, the compounds of this invention can form a mixture with solid powder, such as clay, inorganic silicates, carbonates, as well as wetting agents, adhesives and/or dispersant agent.

The preparation of water dispersible granules: the compound in the invention and powdered solid diluents, wetting agents and adhesives are mixed to smash, kneading together with water, added to the granulation machine with 10 to 100 mesh for granulation, then by drying and sieving (at the scope screen). Also, the compound of the invention, dispersants, disintegrants, wetting agents and solid diluent are added to sanding machine, grinding in water to produce suspension and then spray-drying granulation, usually the content of the prepared granular products is 20%-30%.

DETAILED DESCRIPTION OF THE INVENTION

The present invention is illustrated by the following examples, but without being restricted thereby. (All raw materials are commercially available unless otherwise specified.)

PREPARATION EXAMPLES

Example 1

The Preparation of Compound A-44

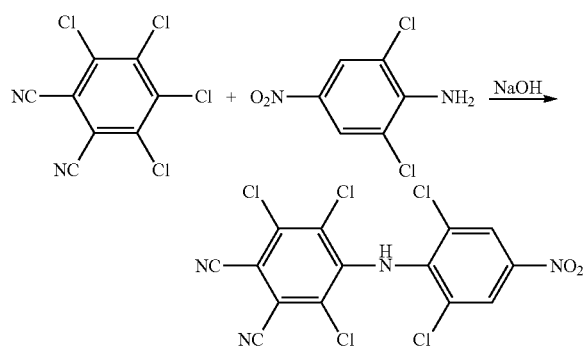

0.60 g (0.015 mol) of sodium hydroxide was added to a solution of 1.64 g (0.0075 mol) of 2,6-dichloro-4-nitroaniline in 40 mL of DMF, followed by addition of 2 g (0.0075 mol) of 3,4,5,6-tetrachlorophthalonitrile under stirring, the mixture was stirred for 5 h after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:4, as an eluent) to give 2.8 g of compound A-44 as yellow solid, m.p. 188-190° C.

$^1$H-NMR (300 MHz, internal standard TMS, solvent CDCl$_3$), δ(ppm): 6.76 (s, 1H, NH), 8.31 (s, 2H, Ph-3,5-2H).

Example 2

The Preparation of Compound A-87

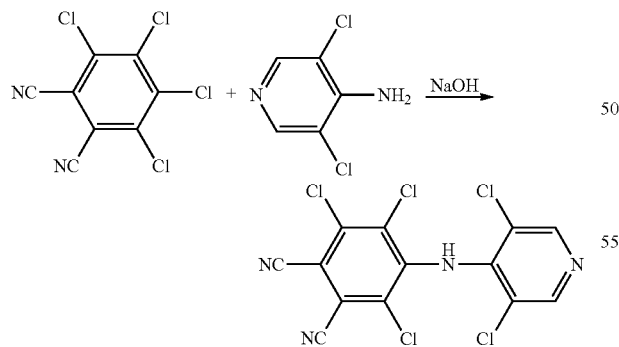

0.60 g (0.015 mol) of sodium hydroxide was added to a solution of 1.22 g (0.0075 mol) of 3,5-dichloropyridin-4-amine in 40 mL of DMF, followed by addition of 2 g (0.0075 mol) of 3,4,5,6-tetrachlorophthalonitrile under stirring, the mixture was stirred for 5 h after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:4, as an eluent) to give 2.6 g of compound A-87 as yellow solid, m.p. 214-216° C.

$^1$H-NMR (300 MHz, internal standard TMS, solvent DMSO), 8.26 (s, 2H, Py-2,6-2H), 11.0 (br, 1H, NH).

Example 3

The Preparation of Compound B-15

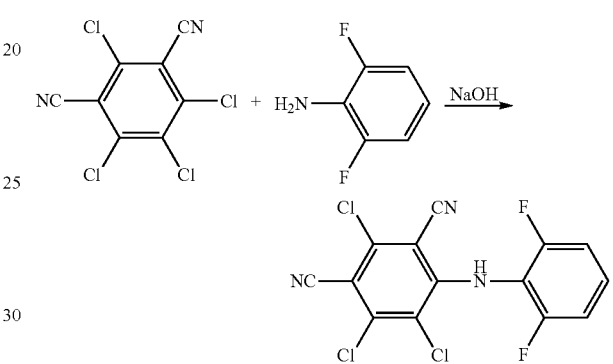

0.64 g (0.016 mol) of sodium hydroxide was added to a solution of 1.03 g (0.008 mol) of 2,6-difluoroaniline in 40 mL of DMF, followed by addition of 2.13 g (0.008 mol) of 2,4,5,6-tetrachloroisophthalonitrile under stirring, the mixture was stirred for 5 h after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:4, as an eluent) to give 1.65 g of compound B-15 as yellowish solid, m.p. 264-266° C.

$^1$H-NMR (300 MHz, internal standard TMS, solvent CDCl$_3$) δ(ppm): 6.70 (s, 1H, NH), 7.07 (t, 2H, Ph-3,5-2H, J=8.1 Hz), 7.37 (m, 1H, Ph-4-1H).

Example 4

The Preparation of Compound B-42

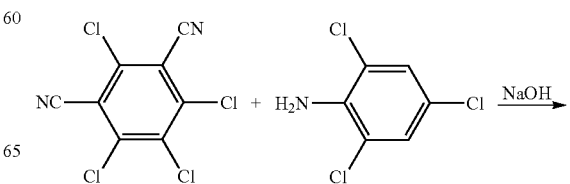

-continued

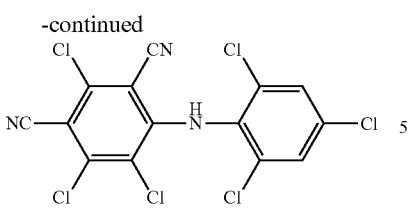

0.64 g (0.016 mol) of sodium hydroxide was added to a solution of 1.57 g (0.008 mol) of 2,4,6-trichloroaniline in 40 mL of DMF, followed by addition of 2.13 g (0.008 mol) of 2,4,5,6-tetrachloroisophthalonitrile under stirring, the mixture was stirred for 5 h after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:4, as an eluent) to give 1.71 g of compound B-42 as yellowish solid, m.p. 241-243° C.

$^1$H-NMR (300 MHz, internal standard TMS, solvent CDCl$_3$) δ(ppm): 6.86 (s, 1H, NH), 7.48 (s, 2H, Ph-3,5-2H).

Example 5

The Preparation of Compound B-49

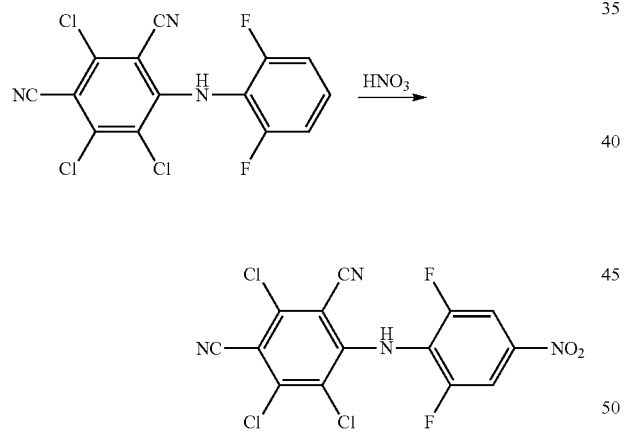

A mixture of compound B-15 in 20 mL of conc. sulfuric acid was cooled in ice bath, followed by addition of a mixed evenly fuming nitric acid (0.004 mol) and concentrated sulfuric acid (0.006 mol) under below 20° C. The mixture was stirred for 5 min after addition. After the reaction was over by Thin-Layer Chromatography monitoring, the reaction mixture was poured into water, stirred and cooled to room temperature, and then extracted with ethyl acetate, the organic phase was washed with saturated brine, dried over anhydrous magnesium sulfate, filtered and then concentrated under reduced pressure. The residue was purified through silica column (ethyl acetate/petroleum ether (boiling point range 60-90° C.)=1:4, as an eluent) to give 0.40 g of compound B-49 as white solid, m.p. 204-206° C.

$^1$H-NMR (300 MHz, internal standard TMS, solvent CDCl$_3$) δ(ppm): 6.70 (s, 1H, NH), 7.97-8.01 (dd, 2H, Ph-3,5-2H, $^3$J=10.8 Hz, $^4$J=3.0 Hz).

Example 6

The Preparation of Compound B-54

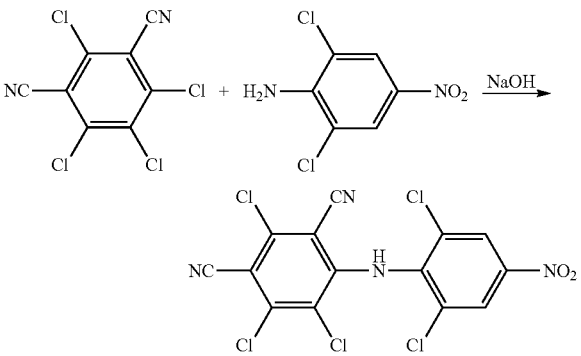

0.10 g (0.0026 mol) of sodium hydroxide was added to a solution of 0.35 g (0.0013 mol) of 2,6-dichloro-4-nitroaniline in 40 mL of DMF, followed by addition of 0.27 g (0.0013 mol) of 2,4,5,6-tetrachloroisophthalonitrile under stirring, the mixture was stirred for 5 h after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:4, as an eluent) to give 0.48 g of compound B-54 as yellowish solid, m.p. 250-252° C.

$^1$H-NMR (300 MHz, internal standard TMS, solvent CDCl$_3$) δ(ppm): 6.93 (s, 1H, NH), 8.34 (s, 2H, Ph-3,5-2H).

Example 7

The Preparation of Compound B-62

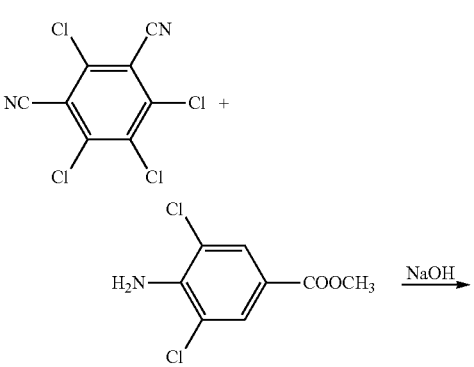

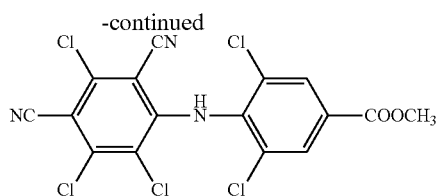

3.12 g (0.078 mol) of sodium hydroxide was added to a solution of 10.33 g (0.039 mol) of methyl 4-amino-3,5-dichlorobenzoate in 40 mL of DMF, followed by addition of 10.37 g (0.039 mol) of 2,4,5,6-tetrachloroisophthalonitrile under stirring, the mixture was stirred for 5 h after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:4, as an eluent) to give 13.65 g of compound B-62 as yellowish solid, m.p. 229-231° C.

$^1$H-NMR (300 MHz, internal standard TMS, solvent CDCl$_3$) δ(ppm): 3.96 (s, 3H, CH$_3$), 6.92 (s, 1H, NH), 8.11 (s, 2H, Ph-2,6-2H).

Example 8

The Preparation of Compound B-64

(1) The Preparation of Compound B-66

2.45 g (0.061 mol) of sodium hydroxide was added to a solution of 13.31 g (0.031 mol) of compound B-62 in 120 mL of THF and water (V$_{THF}$:V$_{water}$=1;1), the mixture was stirred for 5 h in oil bath at 50° C. After the reaction was over by Thin-Layer Chromatography monitoring, the reaction mixture was poured into water and extracted with ethyl acetate, the organic phase was removed and pH value of inorganic phase was adjusted to 5-6, yellowish solid precipated and filtered, that is compound B-66, which was dried for use.

(2) The Preparation of Intermediate Acyl Chloride

2 Drops of DMF was added to a solution of 5.54 g (12.72 mmol) of compound B-66 in 100 mL of petroleum, followed by addition of 2.27 g (19.08 mmol) of SOCl$_2$, the reaction mixture was stirred for 2 h in oil bath at 85° C. After the reaction was over by Thin-Layer Chromatography monitoring, the reaction mixture was concentrated under reduced pressure to give the intermediate acyl chloride.

(3) The Preparation of Compound B-64

0.40 g (0.91 mmol) of the intermediate acyl chloride was added to a solution of 0.12 g (0.909 mmol) of 4-chloroaniline and 0.23 g (2.27 mmol) of triethylamine in 50 mL of THF, the reaction mixture was stirred for 5 h in oil bath at 45° C. After the reaction was over by Thin-Layer Chromatography monitoring, the reaction mixture was poured into water and extracted with ethyl acetate, the organic phase was washed with saturated brine, dried over anhydrous magnesium sulfate, filtered and then concentrated under reduced pressure. The residue was purified through silica column (ethyl acetate/petroleum ether (boiling point range 60-90° C.)=1:3, as an eluent) to give 0.23 g of compound B-64 as white solid, m.p. 275-276° C.

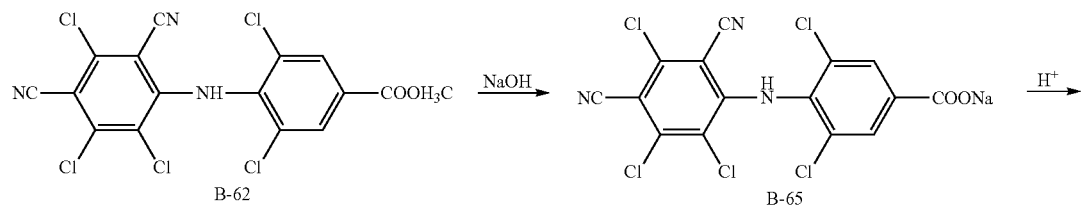

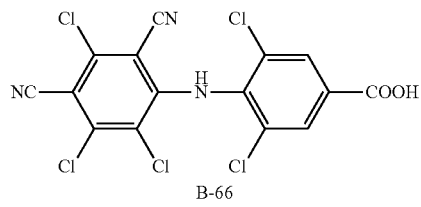

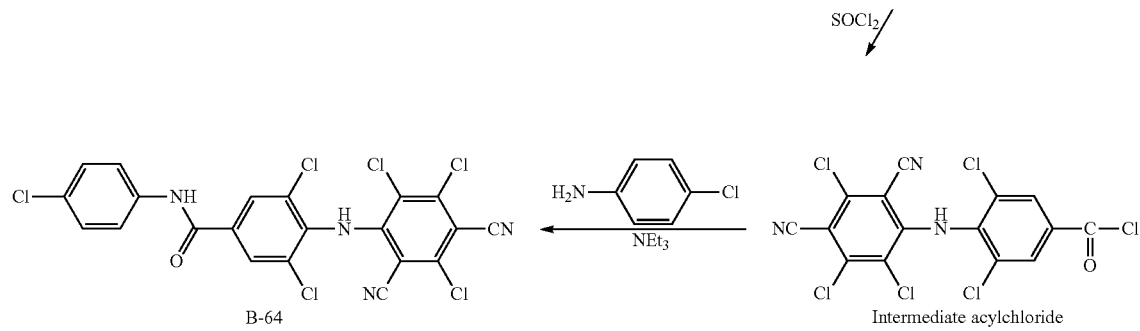

$^1$H-NMR (300 MHz, internal standard TMS, solvent CDCl$_3$) δ(ppm): 7.31-7.35 (m, 2H, 4-Cl-Ph-2,6-2H), 7.81 (d, 2H, 4-Cl-Ph-3,5-2H, J=9.0 Hz), 8.13 (dd, 2H, Ph-2,6-2H, $^3$J=15.7 Hz, $^4$J=1.2 Hz), 10.50 (d, 1H, CONH, J=12.9 Hz).

Example 9

The Preparation of Compound B-75

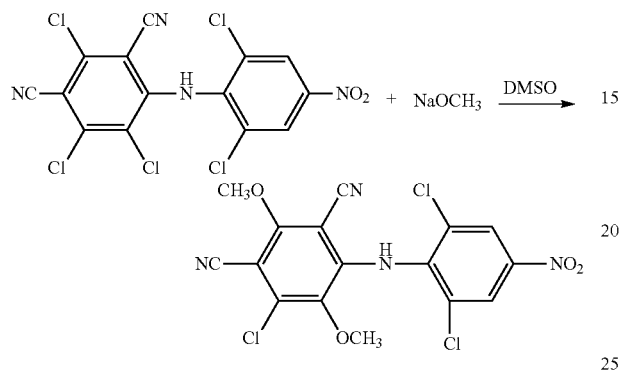

0.14 g (0.0025 mol) of NaOCH$_3$ was added to a solution of 0.55 g (0.0013 mol) of compound B-54 in 50 mL of THF, the reaction mixture was stirred for 8 h in oil bath at 95° C. After the reaction was over by Thin-Layer Chromatography monitoring, the reaction mixture was poured into water and extracted with ethyl acetate, the organic phase was washed with saturated brine, dried over anhydrous magnesium sulfate, filtered and then concentrated under reduced pressure. The residue was purified through silica column (ethyl acetate/petroleum ether (boiling point range 60-90° C.)=1:4, as an eluent) to give 0.16 g of compound B-75 as yellowish solid, m.p. 151-153° C.

$^1$H-NMR (300 MHz, internal standard TMS, solvent CDCl$_3$) δ(ppm): 4.23 (t, 6H, OCH$_3$, J=6.6 Hz), 6.78 (br, 1H, NH), 8.31 (d, 2H, Ph-3,5-2H, J=3.9 Hz).

Example 10

The Preparation of Compound B-115

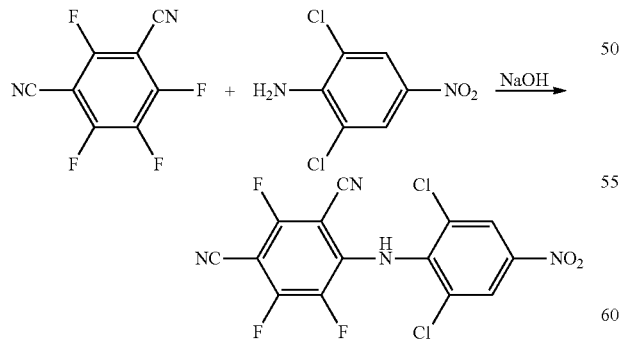

3.12 g (0.078 mol) of sodium hydroxide was added to a solution of 8.07 g (0.039 mol) of 2,6-dichloro-4-nitroaniline in 60 mL of DMF, followed by addition of 7.80 g (0.039 mol) of 2,4,5,6-tetrafluoroisophthalonitrile under stirring, the mixture was stirred for 5 h after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:5, as an eluent) to give 8.08 g of compound B-115 as yellowish solid, m.p. 164-166° C.

$^1$H-NMR (300 MHz, internal standard TMS, solvent CDCl$_3$) δ(ppm): 6.88 (br, 1H, NH), 8.53 (s, 2H, Ph-3,5-2H).

Example 11

The Preparation of Compound B-125

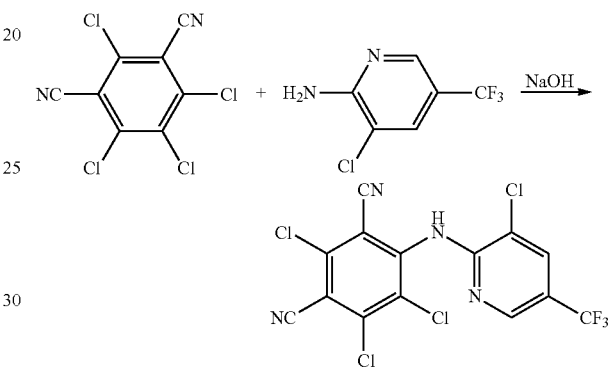

0.30 g (0.0076 mol) of sodium hydroxide was added to a solution of 0.71 g (0.0036 mol) of 3-chloro-5-(trifluoromethyl)pyridin-2-amine in 40 mL of DMF, followed by addition of 1.01 g (0.0038 mol) of 2,4,5,6-tetrachloroisophthalonitrile under stirring, the mixture was stirred for 5 h after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:4, as an eluent) to give 1.15 g of compound B-125 as yellowish solid, m.p. 196-198° C.

$^1$H-NMR (300 MHz, internal standard TMS, solvent CDCl$_3$) δ(ppm): 7.86 (d, 1H, pyridine-4-H, J=1.8 Hz), 9.36 (s, 1H, pyridine-6-H), 10.42 (s, 1H, NH).

Example 12

The Preparation of Compound B-133

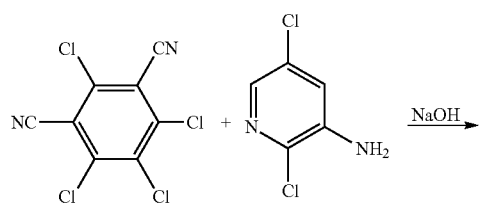

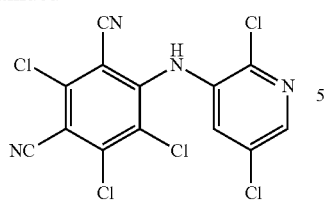

0.60 g (0.0152 mol) of sodium hydroxide was added to a solution of 1.17 g (0.0072 mol) of 2,5-dichloropyridin-3-amine in 40 mL of DMF, followed by addition of 2.02 g (0.0076 mol) of 2,4,5,6-tetrachloroisophthalonitrile under stirring, the mixture was stirred for 5 h after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:4, as an eluent) to give 1.32 g of compound B-133 as white solid, m.p. 236-238° C.

$^1$H-NMR (300 MHz, internal standard TMS, solvent CDCl$_3$) δ(ppm): 6.97 (s, 1H, NH), 7.44 (d, 1H, pyridine-4-H, J=2.1 Hz), 8.30 (d, 1H, pyridine-6-H, J=2.1 Hz).

Example 13

The Preparation of Compound B-139

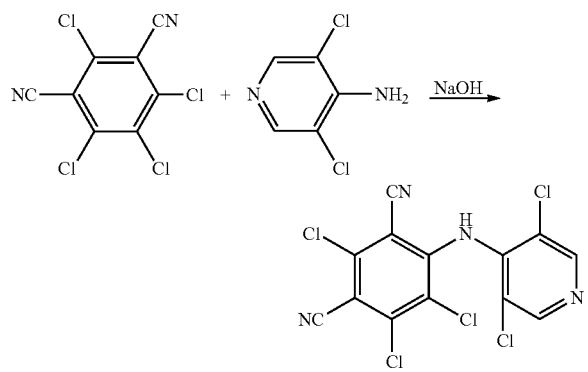

0.60 g (0.0152 mol) of sodium hydroxide was added to a solution of 1.17 g (0.0072 mol) of 3,5-dichloropyridin-4-amine in 40 mL of DMF, followed by addition of 2.02 g (0.0076 mol) of 2,4,5,6-tetrachloroisophthalonitrile under stirring, the mixture was stirred for 5 h after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:4, as an eluent) to give 1.49 g of compound B-139 as white solid, m.p. 236-238° C.

$^1$H-NMR (300 MHz, internal standard TMS, solvent CDCl$_3$) δ(ppm): 8.32 (s, 2H, pyridine-2,6-2H), 7.25 (br, 1H, NH).

Example 14

The Preparation of Compound B-143

0.51 g (0.0128 mol) of sodium hydroxide was added to a solution of 1.00 g (0.0064 mol) of 4,6-dimethoxypyrimidin-2-amine in 40 mL of DMF, followed by addition of 1.79 g (0.0067 mol) of 2,4,5,6-tetrachloroisophthalonitrile under stirring, the mixture was stirred for 5 h after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:4, as an eluent) to give 1.23 g of compound B-143 as white solid, m.p. 197-199° C.

$^1$H-NMR (300 MHz, internal standard TMS, solvent CDCl$_3$) δ(ppm): 3.90 (s, 6H, OCH$_3$), 5.77 (s, 1H, pyrimidine-5-H), 7.36 (s, 1H, NH).

Example 15

The Preparation of Compound B-146

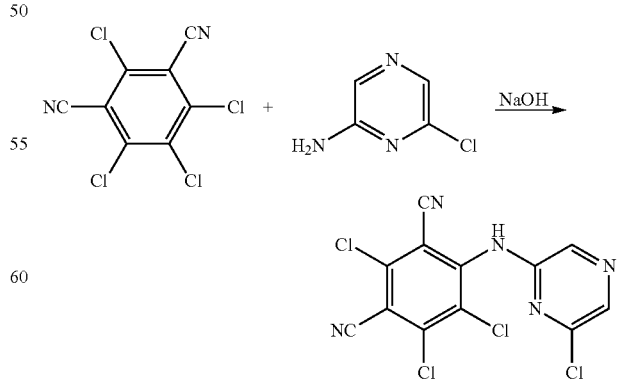

0.60 g (0.0152 mol) of sodium hydroxide was added to a solution of 0.93 g (0.0072 mol) of 6-chloropyrazin-2-amine in 40 mL of DMF, followed by addition of 2.02 g (0.0076 mol) of 2,4,5,6-tetrachloroisophthalonitrile under stirring, the mixture was stirred for 5 h after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:4, as an eluent) to give 0.98 g of compound B-146 as yellow solid, m.p. 254-256° C.

$^1$H-NMR (300 MHz, internal standard TMS, solvent CDCl$_3$) δ(ppm): 6.88 (s, 1H, Py-4-1H), 7.20 (br, 1H, NH), 7.88 (s, 1H, Py-4-1H).

Example 16

The Preparation of Compound B-149

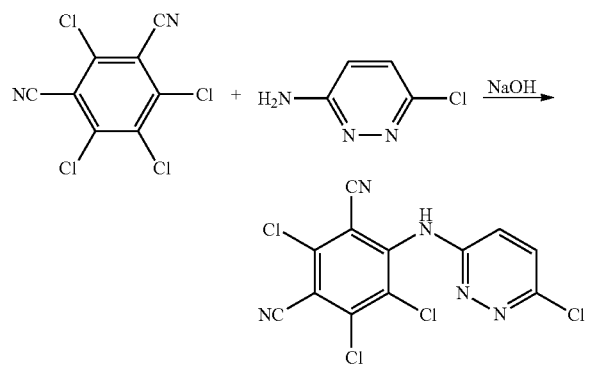

0.67 g (0.0168 mol) of sodium hydroxide was added to a solution of 1.03 g (0.008 mol) of 6-chloropyridazin-3-amine in 40 mL of DMF, followed by addition of 2.23 g (0.0084 mol) of 2,4,5,6-tetrachloroisophthalonitrile under stirring, the mixture was stirred for 5 hours after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:4, as an eluent) to give 1.03 g of compound B-149 as yellow solid, m.p. 202-204° C.

$^1$H-NMR (300 MHz, internal standard TMS, solvent CDCl$_3$) δ(ppm): 6.86 (s, 1H, Py-4-1H), 7.17 (br, 1H, NH), 7.86 (s, 1H, Py-4-1H).

Example 17

The Preparation of Compound C-38

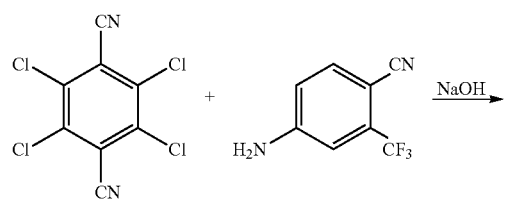

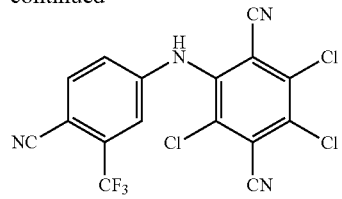

0.30 g (0.0075 mol) of sodium hydroxide was added to a solution of 0.7 g (0.0037 mol) of 4-amino-2-(trifluoromethyl)benzonitrile in 40 mL of DMF, followed by addition of 1 g (0.0037 mol) of 2,3,5,6-tetrachloroterephthalonitrile under stirring, the mixture was stirred for 5 h after addition at room temperature. After the reaction was over by Thin-Layer Chromatography monitoring, the reaction mixture was poured into water, solid precipitated and filtered under reduced pressure to give 1.3 g of compound C-38 as yellow solid, m.p. 176-178° C.

$^1$H-NMR (300 MHz, internal standard TMS, solvent CDCl$_3$) δ(ppm): 6.86 (dd, 1H, Ph-6-1H), 7.16 (d, 1H, Ph-2-1H), 7.73 (d, 1H, Ph-5-1H).

Example 18

The Preparation of Compound C-40

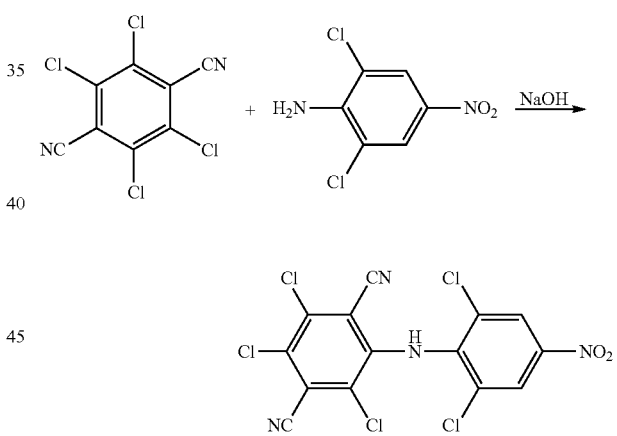

0.60 g (0.015 mol) of sodium hydroxide was added to a solution of 1.64 g (0.0075 mol) of 2,6-dichloro-4-nitroaniline in 40 mL of DMF, followed by addition of 2 g (0.0075 mol) of 2,3,5,6-tetrachloroterephthalonitrile under stirring, the mixture was stirred for 5 h after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:4, as an eluent) to give 3.1 g of compound C-40 as yellow solid, m.p. 156-158° C.

$^1$H-NMR (300 MHz, internal standard TMS, solvent CDCl$_3$) δ(ppm): 6.63 (s, 1H, NH), 8.31 (s, 2H, Ph-3,5-2H).

Example 19

The Preparation of Compound C-99

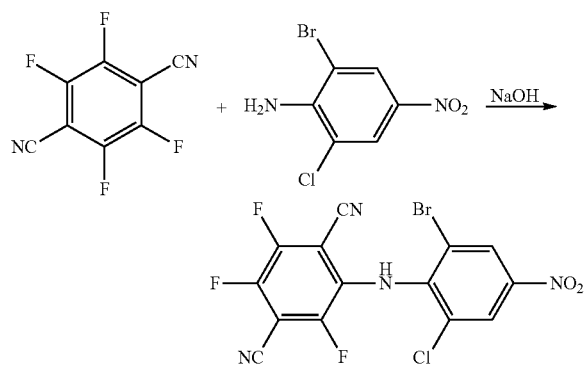

0.60 g (0.015 mol) of sodium hydroxide was added to a solution of 1.88 g (0.0075 mol) of 2-bromo-6-chloro-4-nitroaniline in 40 mL of DMF, followed by addition of 1.50 g (0.0075 mol) of 2,3,5,6-tetrafluoroterephthalonitrile under stirring, the mixture was stirred for 5 h after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:4, as an eluent) to give 2.60 g of compound C-99 as yellow solid.

$^1$H-NMR (300 MHz, internal standard TMS, solvent CDCl$_3$) δ(ppm): 6.38 (br, 1H, NH), 8.24 (d, J=2.7 Hz, 1H, Ph-5-H), 8.47 (d, J=2.7 Hz, 1H, Ph-3-H).

Example 20

The Preparation of Compound C-109

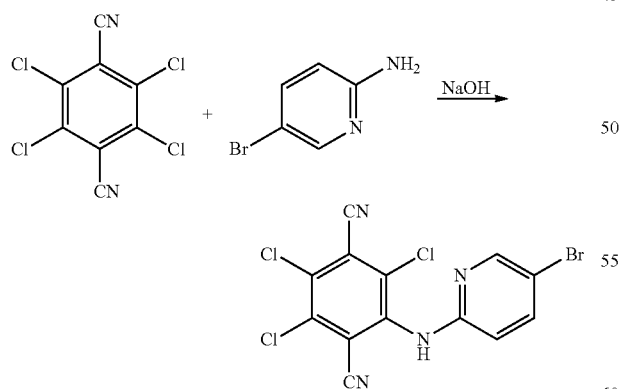

0.60 g (0.015 mol) of sodium hydroxide was added to a solution of 1.3 g (0.0075 mol) of 5-bromopyridin-2-amine in 40 mL of DMF, followed by addition of 2 g (0.0075 mol) of 2,3,5,6-tetrachloroterephthalonitrile under stirring, the mixture was stirred for 5 hours after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:3, as an eluent) to give 2.5 g of compound C-109 as yellow solid, m.p. 154-156° C.

$^1$H-NMR (300 MHz, internal standard TMS, solvent CDCl$_3$) δ(ppm): 9.78 (s, 1H, NH), 6.62 (d, 1H, Py-3-1H), 7.73 (dd, 1H, Py-4-1H), 8.27 (d, 1H, Py-6-1H).

Example 21

The Preparation of Compound C-118

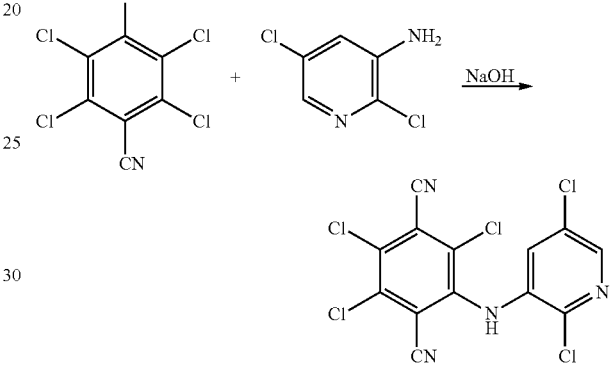

0.60 g (0.015 mol) of sodium hydroxide was added to a solution of 1.22 g (0.0075 mol) of 2,5-dichloropyridin-3-amine in 40 mL of DMF, followed by addition of 2 g (0.0075 mol) of 2,3,5,6-tetrachloroterephthalonitrile under stirring, the mixture was stirred for 5 h after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:3, as an eluent) to give 2.21 g of compound C-118 as yellow solid, m.p. 202-204° C.

$^1$H-NMR (300 MHz, internal standard TMS, solvent CDCl$_3$) δ(ppm): 7.36 (d, J=2.4 Hz, 1H, Py-4-1H), 7.97 (d, J=2.4 Hz, 1H, Py-5-1H), 8.89 (br, 1H, NH).

Example 22

The Preparation of Compound C-124

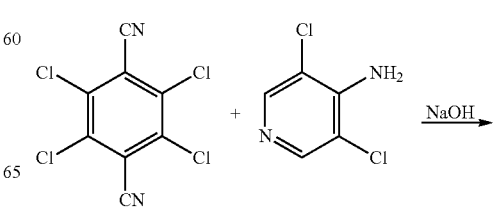

-continued

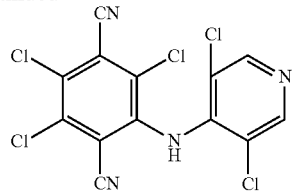

0.60 g (0.015 mol) of sodium hydroxide was added to a solution of 1.22 g (0.0075 mol) of 3,5-dichloropyridin-4-amine in 40 mL of DMF, followed by addition of 2 g (0.0075 mol) of 2,3,5,6-tetrachloroterephthalonitrile under stirring, the mixture was stirred for 5 h after addition at room temperature. After the reaction was over by Thin-Layer Chromatography monitoring, the reaction mixture was poured into water and extracted with ethyl acetate, the organic phase was washed with water and saturated brine, dried over anhydrous magnesium sulfate, filtered and then concentrated under reduced pressure. The residue was purified through silica column (ethyl acetate/petroleum ether (boiling point range 60-90° C.)=1:3, as an eluent) to give 2.16 g of compound C-124 as yellow solid, m.p. 202-204° C.

$^1$H-NMR (300 MHz, internal standard TMS, solvent CDCl$_3$) δ(ppm): 7.28 (br, 1H, NH), 8.30 (s, 2H, Py-2,6-2H).

Other compounds of the present invention were prepared according to the above examples.

Physical properties and $^1$HNMR spectrum ($^1$HNMR, 300 MHz, internal standard: TMS, ppm) of some compounds of this invention are as follows:

Compound A-1: m.p. 170-172° C. δ(CDCl$_3$): 2.32 (s, 3H, Ph-2-CH$_3$), 6.43 (br, 1H, NH), 6.73-6.75 (m, 1H, Ph-6-1H), 7.15-7.17 (m, 1H, Ph-5-1H), 7.19-7.22 (m, 2H, Ph-3,4-2H).

Compound A-2: m.p. 166-168° C. δ(CDCl$_3$): 6.65 (s, 1H, NH), 6.71 (d, 1H, Ph-6-1H), 7.10-7.15 (m, 1H, Ph-4-1H), 7.20-7.25 (m, 1H, Ph-5-1H), 7.46 (d, 1H, Ph-3-1H).

Compound A-3: m.p. 240-242° C. δ(CDCl$_3$): 6.71 (d, J=8.4 Hz, 1H, Ph-6-1H), 7.12 (t, 1H, Ph-5-1H), 7.54 (t, 1H, Ph-4-1H), 8.29 (d, J=8.1 Hz, 1H, Ph-3-1H), 9.43 (br, 1H, NH).

Compound A-4: m.p. 168-170° C. δ(CDCl$_3$): 2.87 (s, 3H, NCH$_3$), 6.48 (d, J=8.4 Hz, 1H, Ph-6-1H), 7.05 (t, 1H, Ph-4-1H), 7.37 (t, 1H, Ph-5-1H), 7.57 (d, J=7.5 Hz, 1H, Ph-3-1H), 10.36 (br, 1H, NH).

Compound A-5: m.p. 138-140° C. δ(CDCl$_3$): 2.34 (s, 3H, Ph-3-CH$_3$), 6.55 (br, 1H, NH), 6.66-6.70 (m, 2H, Ph-2,6-2H), 6.94-6.96 (m, 1H, Ph-4-1H), 7.17-7.22 (m, 1H, Ph-3-1H).

Compound A-6: m.p. 230-232° C. δ(DMSO): 7.18 (d, J=8.1 Hz, 1H, Ph-6-1H), 7.49 (t, 1H, Ph-5-1H), 7.70-7.78 (m, 2H, Ph-2,4-2H), 9.49 (br, 1H, NH).

Compound A-7: m.p. 158-160° C. δ(CDCl$_3$): 2.32 (s, 3H, Ph-4-CH$_3$), 6.41 (br, 1H, NH), 6.82 (d, J=8.4 Hz, 2H, Ph-3,5-2H), 7.32 (d, J=8.4 Hz, 2H, Ph-2,6-2H).

Compound A-8: m.p. 148-150° C. δ(DMSO): 1.32 (9H, t-Bu), 6.66 (br, 1H, NH), 6.85 (d, J=8.4 Hz, 2H, Ph-3,5-2H), 7.35 (d, J=8.4 Hz, 2H, Ph-2,6-2H).

Compound A-9: m.p. 168-170° C. δ(CDCl$_3$): 3.82 (s, 3H, OCH$_3$), 6.40 (br, 1H, NH), 6.87 (d, J=8.4 Hz, 2H, Ph-3,5-2H), 6.92 (d, J=8.4 Hz, 2H, Ph-2,6-2H).

Compound A-10: m.p. 176-178° C. δ(CDCl$_3$): 6.67 (s, 1H, NH), 6.93 (d, 2H, Ph-2,6-2H), 7.21 (d, 2H, Ph-3,5-2H).

Compound A-11: m.p. 198-200° C. δ(DMSO): 3.81 (3H, OCH$_3$), 6.84 (d, J=8.4 Hz, 2H, Ph-2,6-2H), 7.81 (d, J=8.4 Hz, 2H, Ph-3,5-2H), 9.40 (br, 1H, NH).

Compound A-12: m.p. 248-250° C. δ(CDCl$_3$): 6.64 (s, 1H, NH), 6.86 (d, 2H, Ph-2,6-2H), 7.63 (d, 2H, Ph-3,5-2H).

Compound A-13: m.p. 232-233° C. δ(CDCl$_3$): 6.56 (br, 1H, NH), 6.86 (d, J=8.4 Hz, 2H, Ph-2,6-2H), 7.56 (d, J=8.4 Hz, 2H, Ph-3,5-2H).

Compound A-14: m.p. 210-212° C. δ(CDCl$_3$): 6.58 (br, 1H, NH), 6.65 (t, 1H, Ph-6-1H), 8.05-8.16 (m, 2H, Ph-3,5-2H).

Compound A-15: m.p. 68-70° C. δ(CDCl$_3$): 6.52 (d, 1H, Ph-6-1H), 6.88 (br, 1H, NH), 8.07 (d, 1H, Ph-5-1H), 8.40 (s, 1H, Ph-3-1H).

Compound A-16: m.p. 210-212° C. δ(CDCl$_3$): 6.67 (br, 1H, NH), 7.37 (d, 1H, Ph-6-1H), 7.65 (d, 1H, Ph-3-1H), 7.94 (s, 1H, Ph-4-1H).

Compound A-17: m.p. 156-158° C. δ(CDCl$_3$): 6.61 (d, 1H, Ph-6-1H, J=8.4), 6.72 (br, 1H, NH), 7.46 (d, 1H, Ph-5-1H), 7.73 (s, 1H, Ph-3-1H).

Compound A-19: m.p. 156-158° C. δ(CDCl$_3$): 6.69 (s, 1H, NH), 6.82 (d, 1H, Ph-6-H), 7.37 (dd, 1H, Ph-5-H), 7.60 (d, 1H, Ph-3-H).

Compound A-20: m.p. 196-197° C. δ(CDCl$_3$): 2.46 (s, 3H, CH$_3$), 6.30 (br, 1H, NH), 6.83 (d, J=8.4 Hz, 1H, Ph-6-1H), 8.08 (d, J=8.4 Hz, 1H, Ph-5-H), 8.19 (s, 1H, Ph-3-1H).

Compound A-21: m.p. 124-126° C. δ(CDCl$_3$): 1.89 (s, 3H, CH$_3$), 3.90 (s, 3H, OCH$_3$), 7.29 (t, 1H, Ph-4-1H), 7.36 (d, 1H, Ph-5-1H), 7.87 (d, 1H, Ph-3-1H), 8.89 (s, 1H, NH).

Compound A-23: m.p. 172-174° C. δ(CDCl$_3$): 6.47 (d, 1H, Ph-6-1H, J=9.0), 7.48 (dd, 1H, Ph-5-1H), 8.40 (d, 1H, Ph-3-1H), 9.36 (s, 1H, NH).

Compound A-24: m.p. 170-172° C. δ(CDCl$_3$): 2.32 (s, 3H, Ph-3-CH$_3$), 6.47 (br, 1H, NH), 7.27-7.38 (m, 3H, Ph-3,4,5-3H).

Compound A-25: m.p. 187-188° C. δ(CDCl$_3$): 2.29 (s, 3H, CH$_3$), 6.34 (br, 1H, NH), 6.67 (d, J=8.4 Hz, 1H, Ph-6-1H), 7.11 (dd, J=8.4 Hz, J=2.7 Hz, 1H, Ph-5-1H), 7.27 (d, J=2.7 Hz, 1H, Ph-3-1H).

Compound A-26: m.p. 250-252° C. δ(CDCl$_3$): 1.27 (d, J=6.9 Hz, 12H, CH$_3$), 2.99 (m, 2H, CH), 5.85 (br, 1H, NH), 6.97 (d, J=7.2 Hz, 1H, Ph-4-1H), 7.09 (d, J=7.2 Hz, 2H, Ph-3.5-2H).

Compound A-27: m.p. 152-154° C. δ(CDCl$_3$): 6.89 (dd, 1H, Ph-6-1H), 7.22 (d, 1H, Ph-2-1H, J=1.8), 7.74 (d, 1H, Ph-5-1H, J=8.1).

Compound A-28: m.p. 224-226° C. δ(CDCl$_3$): 4.07 (s, 3H, O—CH$_3$), 6.66 (d, 1H, Ph-6-1H), 6.91 (br, 1H, NH), 7.82-7.89 (m, 2H, Ph-3,5-2H).

Compound A-29: m.p. 182-184° C. δ(CDCl$_3$): 6.57 (br, 1H, NH), 6.63 (d, J=8.7 Hz, 1H, Ph-6-1H), 7.20 (dd, J=8.7 Hz, J=2.4 Hz, 1H, Ph-5-H), 7.48 (d, J=2.4 Hz, 1H, Ph-3-H).

Compound A-30: m.p. 176-178° C. δ(CDCl$_3$): 6.59 (br, 1H, NH), 7.24 (d, J=8.4 Hz, 1H, Ph-4-1H), 7.44 (d, J=8.4 Hz, 2H, Ph-3.5-2H).

Compound A-31: m.p. 193-195° C. δ(CDCl$_3$): 6.35 (br, 1H, NH), 7.01 (m, 2H, Ph-3,5-2H), 7.22 (m, 1H, Ph-4-1H).

Compound A-32: m.p. 198-200° C. δ(CDCl$_3$): 6.56 (br, 1H, NH), 6.60 (d, J=1.8 Hz, 1H, Ph-6-1H), 7.07 (dd, J=8.4 Hz, J=1.8 Hz, 1H, Ph-4-1H), 7.38 (d, J=8.4 Hz, H, Ph-3-1H).

Compound A-33: m.p. 211-213° C. δ(CDCl$_3$): 6.55 (br, 1H, NH), 6.73 (dd, J=8.7 Hz, J=2.4 Hz, 1H, Ph-4-1H), 6.99 (d, J=2.4 Hz, 1H, Ph-6-1H), 7.40 (d, J=8.7 Hz, 1H, Ph-3-1H).

Compound A-34: m.p. 232-234° C. δ(DMSO): 6.80 (d, J=1.5 Hz, 2H, Ph-2,6-2H), 6.97 (s, 1H, Ph-4-1H), 9.25 (br, 1H, NH).

Compound A-35: m.p. 147-149° C. δ(CDCl$_3$): 6.65 (br, 1H, NH), 6.53 (d, J=8.1 Hz, 1H, Ph-6-1H), 7.11 (t, 1H, Ph-5-1H), 7.27 (d, J=8.4 Hz, 1H, Ph-4-1H).

Compound A-36: m.p. 195-197° C. δ(DMCO): 6.92 (d, J=8.7 Hz, 1H, Ph-6-1H), 7.44 (d, J=8.7 Hz, 1H, Ph-5-1H), 7.69 (s, 1H, Ph-3-1H)), 7.93 (br, 1H, NH).

Compound A-37: m.p. 198-200° C. δ(DMCO): 3.90 (s, 3H, OCH₃), 6.95 (dd, J=8.4 Hz, J=2.1 Hz, 1H, Ph-6-1H), 7.03 (d, J=2.1 Hz, 1H, Ph-2-1H), 7.85 (d, J=8.4 Hz, 1H, Ph-5-1H), 8.75 (br, 1H, NH).

Compound A-38: m.p. 178-180° C. δ(CDCl₃): 2.24 (s, 6H, Ph-3,4-2CH₃), 6.40 (br, 1H, NH), 6.69 (d, J=8.1 Hz, 1H, Ph-6-1H), 6.87 (s, 1H, Ph-2-1H), 7.08 (d, J=8.1 Hz, 1H, Ph-5-1H).

Compound A-39: m.p. 224-226° C. δ(DMCO): 7.20 (dd, J=8.7 Hz, J=2.1 Hz, 1H, Ph-6-H), 7.45 (d, J=8.7 Hz, 1H, Ph-5-H), 7.57 (d, J=2.1 Hz, 1H, Ph-2-H), 8.62 (br, 1H, NH).

Compound A-40: m.p. 113-115° C. δ(CDCl₃): 2.20 (s, 6H, Ph-2,6-2CH₃), 2.31 (s, 3H, Ph-4-CH₃) 6.39 (br, 1H, NH), 6.76 (s, 2H, Ph-3,5-2H).

Compound A-41: m.p. 200-202° C. δ(DMSO): 6.82-6.90 (m, 1H, Ph-6-1H), 7.12-7.22 (m, 1H, Ph-S-1H), 9.08 (s, 1H, NH).

Compound A-42: yellow oil. δ(DMCO): 8.65 (s, 1H, Ph-5-H), 8.75 (s, 1H, Ph-3-H), 8.90 (br, 1H, NH).

Compound A-43: m.p. 196-198° C. δ(CDCl₃): 6.43 (br, 1H, NH), 7.96 (d, J=8.1 Hz, 2H, Ph-3,5-2H).

Compound A-45: m.p. 146-148° C. δ(CDCl₃): 6.63 (s, 1H, NH), 8.48 (s, 2H, Ph-3,5-2H).

Compound A-46: m.p. 186-188° C. δ(CDCl₃): 6.62 (br, 1H, NH), 8.31 (d, J=2.4 Hz, 1H, Ph-5-H), 8.45 (d, J=2.4 Hz, 1H, Ph-3-H).

Compound A-49: m.p. 202-204° C. δ(CDCl₃): 6.49 (br, 1H, NH), 7.69 (s, 2H, Ph-3,5-2H).

Compound A-50: m.p. 270-272° C. δ(DMSO): 2.07 (s, 3H, Ph-2-CH₃), 3.84 (s, 3H, NHCH₃), 7.80 (br, 1H, NH), 8.64 (s, 1H, Ph-3-1H), 9.60 (s, 1H, Ph-5-1H).

Compound A-51: yellow oil. δ(CDCl₃): 2.90 (s, 3H, NCH₃), 7.80 (d, J=2.7 Hz, 1H, Ph-3-1H), 7.87 (d, J=2.7 Hz, 1H, Ph-5-1H), 10.96 (br, 1H, NH).

Compound A-52: yellow oil. δ(CDCl₃): 3.96 (s, 3H, OCH₃), 7.53 (d, J=2.4 Hz, 1H, Ph-3-1H), 7.95 (d, J=2.4 Hz, 1H, Ph-5-1H), 9.22 (br, 1H, NH).

Compound A-54: m.p. 204-206° C. δ(CDCl₃): 6.59 (s, 1H, NH), 7.33 (s, 2H, Ph-3,5-2H).

Compound A-55: m.p. 206-208° C. δ(CDCl₃): 6.20 (br, 1H, NH), 6.68 (d, J=8.4 Hz, 1H, Ph-6-1H), 7.30 (d, J=8.4 Hz, 1H, Ph-5-1H).

Compound A-56: m.p. 198-200° C. δ(CDCl₃): 651 (br, 1H, NH), 6.70 (s, 1H, Ph-6-1H), 7.96 (s, 1H, Ph-5-1H).

Compound A-57: m.p. 208-210° C. δ(CDCl₃): 6.50 (br, 1H, NH), 7.55 (s, 2H, Ph-3,5-2H).

Compound A-59: m.p. 246-248° C. δ(DMCO): 6.92 (s, 1H, NH), 7.84 (s, 1H, Py-3-1H).

Compound A-60: m.p. 192-194° C. δ(CDCl₃): 6.54 (br, 1H, NH), 7.52 (s, 2H, Ph-3,5-2H).

Compound A-61: m.p. 228-230° C. δ(DMCO): 2.40 (s, 3H, Ph-2-CH₃), 8.64 (s, 1H, Ph-5-1H), 8.93 (br, 1H, NH).

Compound A-79: m.p. 164-166° C. δ(DMSO): 6.73 (s, 1H, NH), 6.96 (d, H, Py-3-1H), 7.84 (dd, 1H, Py-4-1H), 8.27 (d, 1H, Py-6-1H).

Compound A-80: m.p. 124-126° C. δ(CDCl₃): 2.40 (s, 3H, CH₃), 3.66 (br, 1H, NH), 6.54 (s, 1H, Py-3-1H), 6.90 (d, 1H, Py-5-1H), 8.03 (d, 1H, Py-6-1H).

Compound A-81: m.p. 182-184° C. δ(CDCl₃): 2.36 (s, 3H, Py-5-CH₃), 6.63 (d, J=8.1 Hz, 1H, Py-3-H), 6.90 (br, 1H, NH), 7.44 (d, J=8.1 Hz, 1H, Py-4-H), 8.05 (s, 1H, Py-6-H).

Compound A-85: m.p. 108-110° C. δ(DMSO): 8.01 (d, J=2.1 Hz, 1H, Py-4-1H), 8.38 (d, J=2.1 Hz, 1H, Py-5-1H), 10.18 (br, 1H, NH).

Compound A-90: m.p. 196-198° C. δ(CDCl₃): 3.80 (s, 6H, 2OCH₃), 5.64 (s, 1H, Py-5-1H), 6.94 (br, 1H, NH).

Compound B-1: m.p. 212-214° C. δ(CDCl₃): 2.29 (s, 3H, CH₃), 7.00 (s, 1H, NH), 7.15 (d, H, Ph-6-H, J=7.5 Hz), 7.28-7.34 (m, 3H, Ph-3,4,5-3H).

Compound B-2: m.p. 208-210° C. δ(CDCl₃): 7.03 (s, 1H, NH), 7.27-7.38 (m, 3H, Ph-3,5,6-3H), 7.49-7.55 (m, 1H, Ph-4-H).

Compound B-3: m.p. 258-260° C. δ(CDCl₃): 7.12 (s, 1H, NH), 7.24 (d, 1H, Ph-6-H, J=7.5 Hz), 7.47 (t, 1H, Ph-4-H, J=7.2 Hz), 7.68 (t, 1H, Ph-5-H, J=7.5 Hz), 7.78 (d, 1H, Ph-3-H, J=7.8 Hz).

Compound B-4: m.p. 180-182° C. δ(CDCl₃): 2.89 (s, 3H, NCH₃), 6.49 (d, J=8.7 Hz, 1H, Ph-6-1H), 7.04 (t, 1H, Ph-4-1H), 7.35 (t, 1H, Ph-5-1H), 7.56 (d, J=7.8 Hz, 1H, Ph-3-1H), 10.36 (br, 1H, NH).

Compound B-5: m.p. 248-250° C. δ(CDCl₃): 2.40 (s, 3H, Ph-3-CH₃), 7.02 (br, 1H, NH), 7.12-7.36 (m, 4H, Ph-2,3,4,6-4H).

Compound B-6: m.p. 228-230° C. δ(CDCl₃): 7.04 (br, 1H, NH), 7.09 (d, J=7.5 Hz, 1H, Ph-6-1H), 7.20 (s, 1H, Ph-2-1H), 7.33-7.39 (m, 2H, Ph-4,5-2H).

Compound B-7: m.p. 236-238° C. δ(CDCl₃): 7.12 (s, 1H, NH), 7.28-7.40 (m, 1H, Ph-6-H), 7.41-7.52 (m, 2H, Ph-2,4-2H), 7.54-7.62 (m, 1H, Ph-5-H).

Compound B-8: m.p. 250-252° C. δ(DMSO): 7.54-7.64 (m, 2H, Ph-5,6-2H), 7.94-8.00 (m, 2H, Ph-2,4-2H), 9.86 (br, 1H, NH).

Compound B-9: m.p. 144-146° C. δ(DMSO): 1.30 (9H, t-Bu), 6.28 (br, 1H, NH), 6.64 (d, J=8.4 Hz, 2H, Ph-3,5-2H), 7.18 (d, J=8.4 Hz, 2H, Ph-2,6-2H).

Compound B-10: m.p. 259-261° C. δ(CDCl₃): 7.00 (s, 1H, NH), 7.17 (d, 2H, Ph-2,6-2H, J=8.7 Hz), 7.42 (d, 2H, Ph-3,5-2H, J=9.0 Hz).

Compound B-11: m.p. 186-187° C. δ(CDCl₃): 6.06 (br, 1H, NH), 6.51 (d, J=5.7 Hz, 2H, Ph-2,6-2H), 7.52 (d, J=5.7 Hz, 2H, Ph-3,5-2H).

Compound B-12: m.p. 204-206° C. δ(CDCl₃): 7.09 (s, 1H, NH), 7.22-7.32 (m, 4H, Ph-2,3,5,6-4H).

Compound B-13: m.p. 246-248° C. δ(CDCl₃): 2.29 (s, 3H, COOCH₃), 7.08 (s, 1H, NH), 7.17 (d, 2H, Ph-3,5-2H, J=8.7 Hz), 8.10 (d, 2H, Ph-2,6-2H, J=8.7 Hz).

Compound B-14: m.p. 206-208° C. δ(CDCl₃): 6.88 (s, 1H, NH), 6.99 (t, 2H, Ph-5,6-2H, J=8.1 Hz), 7.32 (d, 1H, Ph-3-H, J=2.4 Hz).

Compound B-16: m.p. 218-220° C. δ(CDCl₃): 7.03 (s, 1H, NH), 7.13 (dd, 1H, Ph-6-H, ³J=8.1 Hz, ³J=0.9 Hz), 7.28 (t, 1H, Ph-5-H, J=8.1 Hz), 7.47 (dd, 1H, Ph-4-H, ³J=8.1 Hz, ⁴J=0.9 Hz).

Compound B-17: m.p. 235-237° C. δ(CDCl₃): 6.61 (s, 1H, NH), 7.36 (t, 1H, Ph-4-H, J=7.2 Hz), 7.45 (d, 2H, Ph-3,5-2H, J=7.2 Hz).

Compound B-18: m.p. 209-212° C. δ(CDCl₃): 6.95 (s, 1H, NH), 7.20 (d, 1H, Ph-6-H, J=8.1 Hz), 7.36 (dd, 1H, Ph-5-H, ³J=8.7 Hz, ⁴J=2.7 Hz), 7.54 (d, 1H, Ph-3-H, J=2.4 Hz).

Compound B-19: m.p. 238-242° C. δ(CDCl₃): 6.95 (s, 1H, NH), 7.05 (d, 2H, Ph-2,6-2H, J=1.8 Hz), 7.32 (d, 1H, Ph-4-H, J=1.5 Hz).

Compound B-20: m.p. 203-205° C. δ(CDCl₃): 6.96 (br, 1H, NH), 7.21 (s, 1H, Ph-6-1H), 7.30 (d, J=8.4 Hz, 1H, Ph-4-1H), 7.45 (d, J=8.4 Hz, 1H, Ph-3-1H).

Compound B-21: m.p. 230-232° C. δ(DMSO): 7.13 (dd, J=8.4 Hz, J=2.1 Hz, 1H, Ph-4-1H), 7.39 (d, J=2.1 Hz, 1H, Ph-6-1H), 7.51 (d, J=8.4 Hz, 1H, Ph-3-1H), 9.62 (br, 1H, NH).

Compound B-22: m.p. 200-202° C. δ(CDCl₃): 2.27 (s, 3H, Ph-2-CH₃), 6.86 (s, 1H, NH), 7.07 (d, 1H, Ph-6-H, J=8.4 Hz), 7.23 (dd, 1H, Ph-5-H, ³J=8.4 Hz, ⁴J=2.1 Hz), 7.33 (s, 1H, Ph-3-H).

Compound B-23: m.p. 240-242° C. δ(CDCl$_3$): 2.32 (s, 3H, Ph-CH$_3$), 6.93 (s, 1H, NH), 7.22-7.35 (m, 3H, Ph-3,4,5-H).

Compound B-24: m.p. 204-205° C. δ(CDCl$_3$): 2.36 (s, 3H, COOCH$_3$), 3.92 (s, 3H, Ph-3-CH$_3$), 6.85 (s, 1H, NH), 7.12 (d, 1H, Ph-5-1H, J=8.4 Hz), 7.92 (d, 1H, Ph-6-1H, J=8.4 Hz), 8.02 (s, 1H, Ph-2-1H).

Compound B-25: m.p. 216-218° C. δ(CDCl$_3$): 2.16 (s, 3H, Ph-2-CH$_3$), 3.89 (s, 3H, OCH$_3$), 7.39 (t, 4H, Ph-4-4H), 7.51 (d, J=7.8, 2H, Ph-2,6-2H), 7.93 (d, J=7.8, 2H, Ph-2,6-2H), 8.54 (br, 1H, NH).

Compound B-26: m.p. 198-200° C. δ(CDCl$_3$): 2.23 (s, 3H, CH$_3$), 2.34 (s, 3H, CH$_3$), 6.95 (s, 1H, NH), 6.95 (s, 1H, Ph-6-H), 7.13-7.22 (m, 2H, Ph-3,4-2H).

Compound B-27: m.p. 86-88° C. δ(CDCl$_3$): 1.27 (d, J=6.9 Hz, 12H, CH3), 3.00 (m, 2H, CH), 5.85 (br, 1H, NH), 6.98 (d, J=7.2 Hz, 1H, Ph-4-1H), 7.10 (d, J=7.2 Hz, 2H, Ph-3.5-2H).

Compound B-28: m.p. 166-168° C. δ(CDCl$_3$): 7.00 (s, 1H, NH), 7.20 (d, 1H, Ph-6-H, J=8.4 Hz), 7.57 (dd, 1H, Ph-5-H, $^3$J=8.4 Hz, $^4$J=1.5 Hz), 7.78 (s, 1H, Ph-3-H).

Compound B-29: m.p. 197-199° C. δ(CDCl$_3$): 7.02 (s, 1H, NH), 7.45 (s, 1H, Ph-6-H), 7.55 (d, 1H, Ph-4-H, J=8.4 Hz), 7.65 (d, 1H, Ph-3-H, J=8.4 Hz).

Compound B-30: m.p. 209-212° C. 6.93 (s, 1H, NH), 7.34 (t, 1H, Ph-3-H, J=9.0 Hz), 7.52 (d, 1H, Ph-4-H, J=7.2 Hz), 7.58-7.65 (m, 1H, Ph-3-H).

Compound B-31: m.p. 205-207° C. δ(CDCl$_3$): 7.03 (br, 1H, NH), 7.45 (s, 1H, Ph-6-1H), 7.57 (d, J=8.4 Hz, 1H, Ph-4-1H), 7.66 (d, J=8.4 Hz, 1H, Ph-3-1H).

Compound B-32: m.p. 180-182° C. δ(CDCl$_3$): 6.94 (br, 1H, NH), 7.11 (d, J=8.4 Hz, 1H, Ph-6-1H), 7.47 (d, J=8.4 Hz, 1H, Ph-5-1H), 7.68 (s, 1H, Ph-3-1H).

Compound B-33: m.p. 244-246° C. δ(DMCO): 3.82 (s, 3H, OCH$_3$), 6.95 (dd, J=8.4 Hz, J=2.1 Hz, 1H, Ph-6-1H), 7.03 (d, J=2.1 Hz, 1H, Ph-2-1H), 7.37 (d, J=8.4 Hz, 1H, Ph-5-1H), 8.75 (br, 1H, NH).

Compound B-35: m.p. 220-222° C. 7.04 (d, 1H, Ph-6-H, J=8.7 Hz), 7.07 (s, 1H, NH), 8.20 (dd, 1H, Ph-5-H, $^3$J=9.0 Hz, $^4$J=2.7 Hz), 8.42 (d, 1H, Ph-3-H, J=2.7 Hz).

Compound B-37: m.p. 206-208° C. δ(CDCl$_3$): 10.03 (br, 1H, NH), 6.89 (d, J=9.0 Hz, 1H, Ph-6-1H), 8.41 (dd, J=9.0 Hz, J=2.7 Hz, 1H, Ph-5-1H), 9.21 (d, J=2.7 Hz, 1H, Ph-3-1H).

Compound B-38: m.p. 236-238° C. δ(DMSO): 7.02 (dd, 1H, Ph-6-H, $^3$J=9.6 Hz, $^4$J=2.7 Hz), 8.32 (dd, 1H, Ph-5-H, $^3$J=9.3 Hz, $^4$J=2.7 Hz), 8.63 (d, 1H, Ph-3-H, J=2.7 Hz).

Compound B-39: m.p. 232-234° C. δ(CDCl$_3$): 6.94 (d, 1H, Ph-6-H, J=9.3 Hz), 7.58 (dd, 1H, Ph-5-H, $^3$J=9.0 Hz, $^4$J=2.7 Hz), 8.26 (d, 1H, Ph-3-H, J=2.7 Hz), 9.36 (s, 1H, NH).

Compound B-40: m.p. 242-243° C. δ(CDCl$_3$): 7.07 (s, 1H, NH), 7.25 (d, 1H, Ph-6-H, J=2.1 Hz), 7.42 (d, 1H, Ph-2-H, J=2.4 Hz), 7.83 (d, 1H, Ph-5-H, J=8.4 Hz).

Compound B-41: m.p. 182-184° C. δ(CDCl$_3$): 6.87 (s, 1H, NH), 7.05-7.09 (m, 2H, Ph-5,6-2H).

Compound B-43: m.p. 198-200° C. δ(CDCl$_3$): 6.98 (br, 1H, NH), 7.08 (d, J=9.0 Hz, 1H, Ph-6-H), 7.46 (d, J=9.0 Hz, 1H, Ph-5-1H).

Compound B-44: m.p. 199-201° C. δ(CDCl$_3$): 2.17 (s, 6H, Ph-2,6-2CH$_3$), 2.34 (s, 3H, Ph-4-CH$_3$) 6.81 (br, 1H, NH), 6.97 (s, 2H, Ph-3,5-2H).

Compound B-45: m.p. 253-255° C. δ(CDCl$_3$): 6.88 (br, 1H, NH), 7.33 (s, 1H, Ph-6-1H), 7.96 (s, 1H, Ph-5-1H).

Compound B-46: m.p. 264-266° C. δ(DMCO): 7.53 (s, 2H, Ph-2,6-2H), 8.98 (br, 1H, NH).

Compound B-47: m.p. 238-240° C. δ(CDCl$_3$): 6.84 (br, 1H, NH), 7.63 (s, 2H, Ph-3,5-2H).

Compound B-48: m.p. 196-198° C. δ(CDCl$_3$): 2.55 (s, 3H, CH$_3$), 6.99 (s, 1H, NH), 7.04 (d, 1H, Ph-6-H, J=8.4 Hz), 7.36 (d, 1H, Ph-5-H, J=8.4 Hz).

Compound B-50: m.p. 194-196° C. δ(CDCl$_3$): 6.96 (s, 1H, NH), 7.67 (d, 1H, Ph-5-H, J=2.1 Hz), 7.77 (d, 1H, Ph-3-H, J=2.4 Hz).

Compound B-51: m.p. 259-261° C. δ(CDCl$_3$): 6.91 (s, 1H, NH), 7.74 (s, 2H, Ph-3,5-2H).

Compound B-52: m.p. 201-203° C. δ(CDCl$_3$): 6.91 (s, 1H, NH), 7.72 (s, 2H, Ph-3,5-2H).

Compound B-53: m.p. 197-199° C. 6.86 (s, 1H, NH), 8.05 (dd, 1H, Ph-5-H, $^3$J=9.9 Hz, $^4$J=2.7 Hz), 8.28 (d, 1H, Ph-3-H, J=2.4 Hz).

Compound B-55: m.p. 248-250° C. δ(CDCl$_3$): 6.95 (s, 1H, NH), 8.37 (d, 1H, Ph-3-H, J=2.7 Hz), 8.49 (d, 1H, Ph-5-H, J=2.4 Hz).

Compound B-57: m.p. 247-249° C. δ(CDCl$_3$): 6.96 (s, 1H, NH), 8.51 (s, 2H, Ph-3,5-2H).

Compound B-58: m.p. 232-234° C. δ(CDCl$_3$): 2.43 (s, 3H, Ph-CH$_3$), 6.86 (s, 1H, NH), 8.14 (s, 1H, Ph-5-1H), 8.26 (s, 1H, Ph-3-1H).

Compound B-59: m.p. 228-230° C.

Compound B-60: m.p. 176-178° C. δ(CDCl$_3$): 1.15-1.27 (m, 6H, CH$_3$), 2.49 (q, 4H, CH$_2$, J=7.5 Hz), 6.98 (s, 1H, NH), 7.14 (d, 1H, Ph-5-H, J=8.4 Hz), 7.47 (d, 1H, Ph-3-H, J=8.4 Hz).

Compound B-61: m.p. 171-173° C. δ(CDCl$_3$): 6.97 (br, 1H, NH), 7.56 (s, 2H, Ph-3,5-2H).

Compound B-62a: m.p. 260-262° C. δ(CDCl$_3$): 2.06 (s, 3H), 2.98 (d, 3H), 6.38 (m, 1H), 7.70 (s, 2H), 9.39 (s, 1H).

Compound B-62b: m.p. 240-242° C. δ(CDCl$_3$): 2.08 (s, 3H), 2.93 (d, 3H), 6.22 (m, 1H), 7.35 (t, 2H), 8.60 (s, 1H).

Compound B-63: m.p. 267-269° C. δ(CDCl$_3$): 7.28-7.30 (m, 1H, NHPh-4-H), 7.40 (t, 2H, NHPh-3,5-2H, J=6.9 Hz), δ=7.62 (d, 2H, NHPh-2,6-2H, J=7.8 Hz), δ=7.89-7.95 (m, 2H, NHCOPh-2,6-2H).

Compound B-67: m.p. 108-110° C. δ(CDCl$_3$): 8.88 (br, 1H, NH), 8.71 (s, 2H, Ph-5-1H).

Compound B-68: m.p. 156-158° C. δ(CDCl$_3$): 2.51 (s, 3H, Ph-2-CH$_3$), 8.67 (s, 1H, Ph-5-1H), 8.86 (br, 1H, NH).

Compound B-69: m.p. 260-262° C.

Compound B-70: yellow oil. δ(CDCl$_3$): 1.13-1.21 (m, 6H, CH$_3$), 3.46 (q, 4H, CH$_2$, J=7.2 Hz), 6.90 (s, 1H, NH), 7.13 (t, 2H, Ph-2,6-2H, J=7.5 Hz), 7.31 (d, 1H, Ph-4-H, J=7.5 Hz), 7.42 (t, 2H, Ph-3,5-2H, J=7.2 Hz).

Compound B-71: m.p. 176-178° C. δ(CDCl$_3$): 3.26 (d, 3H, NCH$_3$, J=8.7 Hz), 3.37 (d, 3H, NCH$_3$ J=8.1 Hz), 5.04 (br, H, Ph-NH—C), 5.26 (br, 1H, Ph-NH—C), 6.35 (s, 1H, Ph-NH-Ph), 7.04 (d, 2H, Ph-2,6-2H, J=8.1 Hz), 7.14 (t, 1H, Ph-4-H, J=7.2 Hz), 7.35 (t, 2H, Ph-3,5-2H, J=7.5 Hz).

Compound B-72: m.p. 142-144° C. δ(CDCl$_3$): 4.14 (s, 3H, OCH$_3$), 4.17 (t, 3H, OCH, J=4.2 Hz), 6.91 (s, 1H, Ph-NH-Ph), 7.18 (d, 2H, Ph-2,6-21, J=7.8 Hz), 7.32 (t, 1H, Ph-4-H, J=7.2 Hz), 7.42 (t, 2H, Ph-3,5-2H, J=7.5 Hz).

Compound B-73: m.p. 127-129° C. δ(CDCl$_3$): 3.22 (s, 6H, CH$_3$), 6.85 (s, 1H, NH), 8.32 (s, 2H, Ph-3,5-2H).

Compound B-74: m.p. 198-200° C. δ(CDCl$_3$): 4.25 (s, 3H, CH$_3$), 6.87 (s, 1H, NH), 8.32 (s, 2H, Ph-3,5-2H).

Compound B-76: m.p. 118-120° C. δ(CDCl$_3$): 2.31 (s, 3H, Ph-2-CH$_3$), 6.65 (br, 1H, NH), 7.10-7.33 (m, 4H, Ph-2,3,4,5-4H).

Compound B-77: m.p. 247-249° C. δ(CDCl$_3$): 6.32 (s, 1H, NH), 7.35 (t, 1H, Ph-4-H, J=7.2 Hz), 7.44 (d, 2H, Ph-3,5-2H, J=7.2 Hz).

Compound B-78: m.p. 152-154° C. δ(CDCl$_3$): 2.39 (s, 3H, Ph-3-CH), 6.85 (br, 1H, NH), 7.00-7.02 (m, 2H, Ph-2,6-2H), 7.17-7.19 (m, 1H, Ph-4-1H), 7.29-7.23 (m, 1H, Ph-3-H).

Compound B-79: m.p. 142-144° C. δ(CDCl$_3$): 6.86 (br, 1H, NH), 7.09 (d, J=7.2 Hz, 1H, Ph-6-1H), 7.20 (s, 1H, Ph-2-1H), 7.31-7.40 (m, 2H, Ph-4,5-2H).

Compound B-80: m.p. 166-168° C. δ(DMSO): 7.63-7.68 (m, 2H, Ph-5,6-2H), 7.98-8.04 (m, 2H, Ph-2,4-2H), 10.34 (br, 1H, NH).

Compound B-81: m.p. 123-124° C. δ(CDCl$_3$): 6.38 (br, 1H, NH), 7.26 (d, J=2.4 Hz, 2H, Ph-2,6-2H), 7.27 (d, J=2.4 Hz, 2H, Ph-3,5-2H).

Compound B-82: yellow oil. δ(DMSO): 6.06 (br, 1H, NH), 6.59 (d, J=9 Hz, 2H, Ph-2,6-2H), 7.75 (d, J=9 Hz, 2H, Ph-3,5-2H).

Compound B-83: m.p. 176-177° C. δ(CDCl$_3$): 6.80 (br, 1H, NH), 7.17 (d, J=6.9 Hz, 1H, Ph-6-1H), 7.28 (dd, J-6.9, J=5.4 Hz, 1H, Ph-5-1H), 7.48 (d, J=5.4 Hz, 1H, Ph-4-1H).

Compound B-84: brown oil. δ(CDCl$_3$): 6.83 (br, 1H, NH), 7.17 (s, 1H, Ph-6-1H), 7.24 (d, J=8.4 Hz, 1H, Ph-4-1H), 7.43 (d, J=8.4 Hz, 1H, Ph-3-1H).

Compound B-85: m.p. 178-180° C. δ(CDCl$_3$): 6.54 (br, 1H, NH), 6.73 (t, 2H, Ph-2,6-2H), 7.07 (d, J=1.5 Hz, 1H, Ph-4-1H).

Compound B-86: m.p. 247-249° C. δ(CDCl$_3$): 6.32 (s, 1H, NH), 7.35 (t, 1H, Ph-4-H, J=7.2 Hz), 7.44 (d, 2H, Ph-3,5-2H, J=7.2 Hz).

Compound B-88: yellow oil. δ(CDCl$_3$): 6.38 (br, 1H, NH), 6.64 (d, J=8.4 Hz, 1H, Ph-6-1H), 7.45 (d, J=8.4 Hz, 1H, Ph-5-1H), 7.66 (s, 1H, Ph-3-1H).

Compound B-89: yellow oil. δ(CDCl$_3$): 2.96 (s, 3H, Ph-2-CH$_3$) 6.36 (br, 1H, NH), 6.58 (d, J=8.1 Hz, 1H, Ph-6-1H), 6.97-7.10 (m, 2H, Ph-3,5-2H).

Compound B-90: yellow oil. δ(CDCl$_3$): 2.19 (s, 3H, Ph-3-CH$_3$), 6.03 (br, 1H, NH), 7.92-7.23 (m, 3H, Ph-3,4,5-3H).

Compound B-91: m.p. 171-172° C. δ(CDCl$_3$): 2.46 (s, 3H, CH3), 6.56 (br, 1H, NH), 7.20 (d, J=8.4 Hz, 1H, Ph-6-1H), 8.15 (d, J=8.4 Hz, 1H, Ph-5-1H), 8.22 (s, 1H, Ph-3-1H).

Compound B-92: m.p. 122-124° C. δ(CDCl$_3$): 6.82 (br, 1H, NH), 7.24 (d, J=9.0 Hz, 1H, Ph-6-1H, J=8.4 Hz), 7.59 (d, J=9.0 Hz, 1H, Ph-5-1H), 7.78 (s, 1H, Ph-3-1H).

Compound B-94: yellow oil. δ(CDCl$_3$): 6.98 (br, 1H, NH), 7.48 (s, 1H, Ph-6-1H), 7.56 (d, J=8.4 Hz, 1H, Ph-4-1H), 7.65 (d, J=8.4 Hz, 1H, Ph-3-1H).

Compound B-95: yellow oil. δ(CDCl$_3$): 7.03 (br, 1H, NH), 7.14-7.18 (m, 1H, Ph-6-1H), 8.18-8.21 (m, 1H, Ph-5-1H), 8.41 (d, J=2.7 Hz, 1H, Ph-3-1H).

Compound B-96: m.p. 134-136° C. δ(CDCl$_3$): 6.76 (d, J=8.4 Hz, 1H, Ph-6-1H), 7.12 (t, 1H, Ph-5-1H), 7.58 (t, 1H, Ph-4-1H), 8.29 (d, J=8.1 Hz, 1H, Ph-3-1H), 9.43 (br, 1H, NH).

Compound B-97: m.p. 82-84° C. δ(CDCl$_3$): 6.92 (d, J=9.0 Hz, 1H, Ph-6-H), 7.55 (dd, $^3$J=9.0 Hz, $^4$J=2.7 Hz, 1H, Ph-5-H), 8.28 (d, J=2.7 Hz, 1H, Ph-3-H), 9.40 (s, 1H, NH).

Compound B-98: yellow oil. δ(CDCl$_3$): 6.70 (br, 1H, NH), 7.83 (d, J=8.4 Hz, H, Ph-6-1H), 7.51 (s, 1H, Ph-2-1H). 7.58 (d, J=8.4 Hz, 1H, Ph-5-1H).

Compound B-99: yellow oil. δ(CDCl$_3$): 3.73 (s, 3H, OCH$_3$), 6.26 (br, 1H, NH), 6.48 (dd, J=8.4 Hz, J=2.1 Hz, 1H, Ph-6-1H), 6.60 (d, J=2.1 Hz, 1H, Ph-2-1H), 7.61 (d, J=8.4 Hz, 1H, Ph-5-1H).

Compound B-100: m.p. 147-149° C. δ(CDCl$_3$): 2.17 (s, 6H, Ph-2,6-2CH$_3$), 2.33 (s, 3H, Ph-4-CH$_3$), 6.56 (br, 1H, NH), 6.96 (s, 2H, Ph-3,5-2H).

Compound B-101: m.p. 268-270° C. δ(DMSO): 9.23 (br, 1H, NH), 7.14 (d, J=5.4 Hz, 1H, Ph-6-1H), 7.22 (m, 1H, Ph-5-1H).

Compound B-102: m.p. 156-158° C. δ(CDCl$_3$): 6.72 (br, 1H, NH), 7.15 (d, J=8.7 Hz, 1H, Ph-6-1H), 7.48 (d, J=8.7 Hz, 1H, Ph-5-1H).

Compound B-103: yellow oil. δ(CDCl$_3$): 6.53 (br, 1H, NH), 7.46 (s, 2H, Ph-3,5-2H).

Compound B-104: m.p. 138-140° C. δ(CDCl$_3$): 6.70 (br, 1H, NH), 6.86 (s, 1H, Ph-3,5-1H), 7.63 (d, 1H, Ph-3,5-1H).

Compound B-105: m.p. 75-77° C. δ(CDCl$_3$): 6.70 (m, 2H, Ph-2,6-2H), 710 (br, 1H, NH).

Compound B-106: m.p. 178-180° C. δ(CDCl$_3$): 6.60 (br, 1H, NH), 7.62 (s, 2H, Ph-3,5-2H).

Compound B-109: m.p. 164-166° C. δ(CDCl$_3$): 6.79 (br, 1H, NH), 8.34 (s, 2H, Ph-3,5-2H).

Compound B-111: m.p. 128-130° C. δ(CDCl$_3$): 6.31 (br, 1H, NH), 7.66 (s, 2H, Ph-3,5-2H).

Compound B-112: m.p. 98-100° C. δ(CDCl$_3$): 6.60 (br, 1H, NH), 7.92 (d, J-10.8 Hz, 2H, Ph-3,5-2H).

Compound B-116: yellow oil. δ(CDCl$_3$): 6.86 (br, 1H, NH), 8.48 (d, J=2.7 Hz, 1H, Ph-5-1H), 8.70 (d, J=2.7 Hz, 1H, Ph-3-1H).

Compound B-117: m.p. 122-124° C. δ(CDCl$_3$): 6.63 (br, 1H, NH), 7.57 (s, 2H, Ph-3,5-2H).

Compound B-120: m.p. 266-268° C. δ(CDCl$_3$): 6.92-6.97 (m, 1H, pyridine-5-H), 7.47 (d, 1H, pyridine-3-H, J=7.8 Hz), 7.67-7.72 (m, 1H, pyridine-4-H), 9.10 (d, 1H, pyridine-6-H, J=7.5 Hz), 10.16 (s, 1H, NH).

Compound B-121: m.p. 1.16-118° C. δ(CDCl$_3$): 6.79 (t, 1H, Py-5-H), 8.04 (dd, J=7.2 Hz, J=1.2 Hz, 1H, Py-4-1H), 9.09 (dd, J=7.2 Hz, J=1.2 Hz, 1H, Py-6-H), 10.22 (br, 1H, NH)

Compound B-122: m.p. 168-170° C. δ(DMSO): 6.42 (d, 1H, pyridine-3-H, J=8.1 Hz), 7.72 (d, 1H, pyridine-6-H, J=2.4 Hz), 7.53 (dd, 1H, pyridine-4-H, $^3$J=8.1 Hz, $^4$J=2.4 Hz), 9.22 (s, 1H, NH).

Compound B-123: m.p. 122-124° C. δ(CDCl$_3$): 2.37 (s, 3H, Py-4-CH$_3$), 7.95 (s, 1H, Py-4-H), 8.89 (s, 1H, Py-6-H), 10.14 (br, 1H, NH)

Compound B-124: m.p. 122-124° C., δ(DMSO): 2.37 (s, 3H, CH$_3$), 7.95 (d, 1H, pyridine-4-H, J=1.8 Hz), 8.89 (d, 1H, pyridine-6-H, J=1.8 Hz), 10.14 (br, 1H, NH).

Compound B-127: m.p. 280° C. did not melt. δ(DMCO): 6.95 (s, 1H, NH), 7.88 (s, 1H, Py-3-1H).

Compound B-128: m.p. 136-138° C. δ(CDCl$_3$): 7.32 (br, 1H, NH), 7.84 (s, 1H, Py-4-1H).

Compound B-128b: m.p. 168-170° C.

Compound B-130: m.p. 176-178° C., δ(DMSO): 7.35-7.39 (m, 1H, pyridine-4-H), 7.57-7.60 (m, 1H, pyridine-5-H), 8.37 (d, 1H, pyridine-6-H, J-4.2 Hz), 8.45 (d, 1H, pyridine-2-H, J=2.4 Hz), 9.61 (br, 1H, NH).

Compound B-131: m.p. 243-245° C. δ(CDCl$_3$): 7.03 (s, 1H, NH), 7.34-7.38 (m, 1H, pyridine-5-H), 7.54 (d, 1H, pyridine-4-H, J=8.1 Hz), 8.38 (d, 1H, pyridine-6-H, J=3.3 Hz).

Compound B-132: m.p. 194-196° C., δ(DMSO): 7.39 (dd, 1H, pyridine-4-1H, $^3$J=8.7 Hz, $^4$J=2.4 Hz), 7.47 (d, 1H, pyridine-5-H, J=8.7 Hz), 8.10 (d, 1H, pyridine-2-H, J=2.4 Hz), 9.62 (br, 1H, NH).

Compound B-135: m.p. 234-236° C., δ(DMSO): 2.33 (s, 3H, CH$_3$), 7.40 (d, 1H, pyridine-5-H, J=5.1 Hz), 8.29 (d, 1H, pyridine-6-H, J=5.1 Hz), 9.50 (s, 1H, NH).

Compound B-137: m.p. 246-248° C., δ(DMSO): 6.90-6.93 (m, 2H, pyridine-3,5-2H), 8.12 (d, 1H, pyridine-6-H, J=5.7 Hz), 10.03 (s, 1H, NH).

Compound B-138: m.p. 220-222° C. δ(DMSO): 6.12 (d, 1H, pyridine-5-H, J=6.6 Hz), 7.72 (d, 1H, pyridine-6-H, J=6.6 Hz), 8.24 (s, 1H, pyridine-2-H), 12.18 (s, 1H, NH).

Compound B-140b: m.p. 262-264° C.

Compound B-141: m.p. 212-214° C., δ(DMSO): 6.93 (t, 1H, pyrimidine-5-H, J-4.8 Hz), 8.45 (d, 2H, pyrimidine-4,6-2H, J=5.1 Hz), 10.76 (br, 1H, NH).

Compound B-142: m.p. 205-207° C., δ(CDCl$_3$): 2.42 (d, 6H, CH$_3$, J=3.9 Hz), 6.76 (s, 1H, pyrimidine-5-H), 7.49 (s, 1H, NH).

Compound B-144: m.p. 146-148° C., δ(CDCl₃): 1.54-1.59 (m, 3H, CH₃), 4.39-4.44 (m, 2H, CH₂), 9.08 (s, 1H, pyrimidine-6-H).

Compound C-1: m.p. 176-178° C. δ(CDCl₃): 2.33 (s, 3H, Ph-2-CH₃), 6.43 (br, 1H, NH), 6.68-6.70 (m, 1H, Ph-6-1H), 7.10-7.13 (m, 1H, Ph-5-1H), 7.23-7.25 (m, 2H, Ph-3,4-2H).

Compound C-2: m.p. 180-182° C. δ(CDCl₃): 6.55 (s, 1H, NH), 6.62 (d, 1H, Ph-6-1H), 7.00-7.05 (m, 1H, Ph-4-1H), 7.18-7.23 (m, 1H, Ph-5-1H), 7.50 (dd, 1H, Ph-3-1H).

Compound C-3: m.p. 212-214° C. δ(CDCl₃): 7.01 (d, J=8.4 Hz, 1H, Ph-6-1H), 7.27 (t, 1H, Ph-5-1H), 7.64 (t, 1H, Ph-4-1H), 8.27 (d, J=7.8 Hz, 1H, Ph-3-1H), 9.43 (br, 1H, NH).

Compound C-4: m.p. 134-136° C. δ(CDCl₃): 2.88 (s, 3H, NCH₃), 6.47 (d, J=8.4 Hz, 1H, Ph-6-1H), 6.99 (t, 1H, Ph-4-1H), 7.36 (t, 1H, Ph-5-1H), 7.55 (d, J=7.8 Hz, 1H, Ph-3-1H), 10.16 (br, 1H, NH).

Compound C-5: m.p. 126-128° C. δ(CDCl₃): 6.48 (br, 1H, NH), 6.73 (d, J=7.5 Hz, 1H, Ph-6-1H), 6.85 (s, 1H, Ph-2-1H), 7.09-7.23 (m, 2H, Ph-4,5-2H).

Compound C-6: m.p. 140-142° C. δ(CDCl₃): 2.35 (s, 3H, Ph-3-CH₃), 6.73 (br, 1H, NH), 6.70-6.73 (m, 2H, Ph-2,6-2H), 7.01-7.04 (m, 1H, Ph-4-1H), 7.23-7.25 (m, 1H, Ph-3-1H).

Compound C-7: m.p. 198-200° C. δ(CDCl₃): 6.63 (br, 1H, NH), 7.12 (d, J=8.1 Hz, 1H, Ph-6-1H), 7.45 (t, 1H, Ph-5-1H), 7.75-7.82 (m, 2H, Ph-2,4-2H).

Compound C-8: m.p. 176-178° C. δ(DMSO): 3.81 (3H, OCH₃), 6.83 (d, J=8.4 Hz, 2H, Ph-2,6-2H), 7.83 (d, J=8.4 Hz, 2H, Ph-3,5-2H), 9.32 (br, 1H, NH).

Compound C-9: m.p. 138-140° C. δ(DMSO): 1.32 (9H, t-Bu), 6.58 (br, 1H, NH), 6.82 (d, J=8.4 Hz, 2H, Ph-3,5-2H), 7.32 (d, J=8.4 Hz, 2H, Ph-2,6-2H).

Compound C-10: m.p. 158-160° C. δ(CDCl₃): 2.33 (s, 3H, Ph-4-CH₃), 6.28 (br, 1H, NH), 6.70 (d, J=8.4 Hz, 2H, Ph-3,5-2H), 7.12 (d, J=8.4 Hz, 2H, Ph-2,6-2H).

Compound C-11: m.p. 113-114° C. δ(CDCl₃): 6.56 (br, 1H, NH), 6.87 (d, J-8.4 Hz, 2H, Ph-2,6-2H), 7.57 (d, J=8.4 Hz, 2H, Ph-3,5-2H).

Compound C-12: m.p. 228-230° C. δ(CDCl₃): 6.56 (s, 1H, NH), 6.82 (d, 2H, Ph-2,6-2H), 7.60 (d, 2H, Ph-3,5-2H).

Compound C-13: m.p. 146-148° C. δ(CDCl₃): 6.53 (s, 1H, NH), 6.88 (d, 2H, Ph-2,6-2H), 7.18 (d, 2H, Ph-3,5-2H).

Compound C-14: m.p. 180-182° C. δ(CDCl₃): 3.81 (s, 3H, OCH₃), 6.57 (br, 1H, NH), 6.85-6.88 (m, 4H, Ph-2,3,5,6-4H).

Compound C-15: m.p. 174-176° C. δ(CDCl₃): 6.45 (br, 1H, NH), 6.91 (d, J=8.4 Hz, 1H, Ph-6-H), 7.25 (dd, J=8.4 Hz, J=2.4 Hz, 1H, Ph-5-H), 7.50 (d, J=2.4 Hz, 1H, Ph-3-H).

Compound C-16: m.p. 235-236° C. δ(CDCl₃): 6.52 (br, 1H, NH), 7.31 (d, J=8.4 Hz, 1H, Ph-4-1H). 7.45 (d, J=8.4 Hz, 2H, Ph-3,5-2H).

Compound C-17: m.p. 208-210° C. δ(CDCl₃): 6.25 (br, 1H, NH), 7.14 (m, 2H, Ph-3,5-2H), 7.30 (m, 1H, Ph-4-1H).

Compound C-18: m.p. 254-256° C. δ(DMSO): 6.99 (d, J=2.1 Hz, 1H, Ph-6-1H), 7.05 (dd, J=8.4 Hz, J=2.1 Hz, 1H, Ph-4-1H), 7.43 (d, J=8.4 Hz, 1H, Ph-5-1H), 8.79 (br, 1H, NH).

Compound C-19: m.p. 204-206° C. δ(CDCl₃): 6.45 (br, 1H, NH), 6.69 (dd, J=8.7 Hz, J=2.4 Hz, 1H, Ph-4-1H), 6.95 (d, J=2.4 Hz, 1H, Ph-6-1H), 7.37 (d, J=8.7 Hz, 1H, Ph-3-1H).

Compound C-20: m.p. 178-180° C. δ(CDCl₃): 6.45 (br, 1H, NH), 6.85 (t, 2H, Ph-2,6-2H), 6.48 (d, J=1.5 Hz, 1H, Ph-4-1H).

Compound C-21: m.p. 230-232° C. δ(CDCl₃): 6.55 (br, 1H, NH), 6.79 (d, J=8.1 Hz, 1H, Ph-6-1H), 7.18 (t, 1H, Ph-5-1H), 7.18 (d, J=8.4 Hz, 1H, Ph-4-1H).

Compound C-22: m.p. 197-199° C. δ(CDCl₃): 6.44 (br, 1H, NH), 6.82 (d, J=8.4 Hz, 1H, Ph-6-1H), 7.40 (d, J=8.4 Hz, 1H, Ph-5-1H), 7.64 (s, 1H, Ph-3-1H).

Compound C-23: m.p. 216-218° C. δ(CDCl₃): 6.88 (d, J=9.0 Hz, 1H, Ph-6-1H), 7.47 (dd, J=9.0 Hz, J=2.7 Hz, 1H, Ph-5-1H), 9.20 (d, J=2.7 Hz, 1H, Ph-3-1H), 9.96 (s, 1H, NH).

Compound C-24: m.p. 230-231° C. δ(CDCl₃): 1.28 (d, J=6.9 Hz, 12H, CH₃), 2.99 (m, 2H, CH), 5.85 (br, 1H, NH), 6.99 (d, J=7.2 Hz, 1H, Ph-4-1H), 7.10 (d, J=7.2 Hz, 2H, Ph-3,5-2H).

Compound C-25: m.p. 161-162° C. δ(CDCl₃): 2.30 (s, 3H, CH₃), 6.18 (br, 1H, NH), 6.61 (d, J=8.4 Hz, 1H, Ph-6-1H), 7.09 (dd, J=8.4 Hz, J=2.7 Hz, 1H, Ph-5-1H), 7.24 (d, J=2.7 Hz, 1H, Ph-3-1H).

Compound C-26: m.p. 212-214° C. δ(CDCl₃): 2.32 (s, 3H, Ph-3-CH₃), 6.47 (br, 1H, NH), 7.19-7.23 (m, 3H, Ph-3,4,5-3H).

Compound C-27: m.p. 172-174° C. δ(CDCl₃): 6.68 (br, 1H, NH), 6.84 (t, 1H, Ph-6-1H), 8.04-8.13 (m, 2H, Ph-3,5-2H).

Compound C-28: m.p. 172-174° C. δ(CDCl₃): 6.68 (d, 1H, Ph-6-1H), 6.70 (br, 1H, NH), 7.83 (d, 1H, Ph-5-1H), 7.90 (d, 1H, Ph-3-1H).

Compound C-29: m.p. 190-192° C. δ(CDCl₃): 6.58 (br, 1H, NH), 7.63 (d, 1H, Ph-6-1H), 7.67 (s, 1H, Ph-3-1H), 7.97 (s, 1H, Ph-4-1H).

Compound C-30: m.p. 166-168° C. δ(CDCl₃): 6.60 (br, 1H, NH), 6.79 (d, 1H, Ph-6-1H, J=8.4), 7.47 (d, 1H, Ph-5-1H), 7.74 (s, 1H, Ph-3-1H).

Compound C-32: m.p. 178-180° C. δ(CDCl₃): δ6.56 (s, 1H, NH), 7.08 (d, 1H, Ph-6-H), 7.41 (d, 1H, Ph-5-H), 7.62 (d, 1H, Ph-3-H).

Compound C-33: m.p. 162-164° C. δ(CDCl₃): 6.65 (d, 1H, Ph-6-1H), 8.07 (dd, 1H, Ph-5-1H), 8.40 (d, 1H, Ph-3-1H), 9.38 (br, 1H, NH).

Compound C-34: m.p. 154-156° C. δ(CDCl₃): 2.05 (s, 3H, CH₃), 3.89 (s, 3H, OCH₃), 7.29 (t, 1H, Ph-4-1H), 7.46 (d, 1H, Ph-5-1H), 7.93 (d, 1H, Ph-3-1H), 8.66 (s, 1H, NH).

Compound C-35: m.p. 148-150° C. δ(CDCl₁): 4.06 (s, 3H, O—CH₃), 6.66 (d, 1H, Ph-6-1H), 6.84 (br, 1H, NH), 7.82-7.89 (m, 2H, Ph-3,5-2H).

Compound C-36: yellow oil. δ(DMCO): 3.91 (s, 3H, OCH₃), 6.68 (br, 1H, NH), 6.85 (dd, J=8.4 Hz, J=2.1 Hz, 1H, Ph-6-1H), 6.97 (d, J=2.1 Hz, 1H, Ph-2-1H), 7.85 (d, J=8.4 Hz, 1H, Ph-5-1H).

Compound C-37: m.p. 154-156° C. δ(CDCl₃): 2.33 (s, 3H, Ph-4-CH₃), 6.52 (br, 1H, NH), 6.62 (d, J=8.1 Hz, 1H, Ph-6-1H), 6.69 (s, 1H, Ph-2-1H), 7.06 (d, J=8.1 Hz, 1H, Ph-5-1H).

Compound C-39: m.p. 174-176° C. δ(CDCl₃): 6.52 (br, 1H, NH), 6.63 (dd, J=8.4 Hz, J=2.7 Hz, 1H, Ph-6-H), 7.20 (d, J=8.4 Hz, 1H, Ph-5-H), 7.42 (d, J=2.7 Hz, 1H, Ph-2-H).

Compound C-41: m.p. 98-100° C. δ(CDCl₃): 6.61 (s, 1H, NH), 8.51 (s, 2H, Ph-3,5-2H).

Compound C-42: m.p. 206-208° C. δ(CDCl₃): 6.43 (br, 1H, NH), 7.59 (s, 2H, Ph-3,5-2H).

Compound C-45: m.p. 166-168° C. δ(CDCl₃): 6.44 (br, 1H, NH), 7.96 (d, J=8.4 Hz, 2H, Ph-3,5-2H).

Compound C-46: m.p. 196-197° C. δ(CDCl₃): 6.54 (br, 1H, NH), 7.96 (d, J=10.8 Hz, 2H, Ph-3,5-2H).

Compound C-47: m.p. 152-154° C. δ(CDCl₃): 6.50 (br, 1H, NH), 7.55 (s, 2H, Ph-3,5-2H).

Compound C-48: m.p. 132-134° C. δ(DMCO): 8.65 (s, 1H, Ph-5-1H), 8.77 (s, 1H, Ph-3-H), 8.91 (br, 1H, NH).

Compound C-49: m.p. 160-162° C. δ(CDCl₃): 6.58 (br, 1H, NH), 8.34 (d, J=2.7 Hz, 1H, Ph-5-H), 8.47 (d, J=2.7 Hz, 1H, Ph-3-H).

Compound C-50: m.p. 138-140° C. δ(CDCl₃): 6.56 (br, 1H, NH). 7.65 (s, 2H, Ph-3,5-2H).

Compound C-51: m.p. 170-172° C. δ(CDCl₃): 6.92-6.94 (m, 1H, Ph-6-1H), 6.99-7.05 (m, 1H, Ph-5-1H).

Compound C-52: m.p. 204-206° C. δ(CDCl₃): 651 (br, 1H, NH), 6.93 (s, 1H, Ph-6-1H), 758 (s, 1H, Ph-5-1H).

Compound C-53: m.p. 176-178° C. δ(CDCl₃): 9.18 (br, 1H, NH), 7.69 (s, 2H, Ph-3,5-2H).

Compound C-54: m.p. 278-280° C. δ(CDCl₃): 6.49 (br, 1H, NH), 6.74 (d, J=8.7 Hz, 1H, Ph-6-1H), 7.36 (d, J=8.7 Hz, 1H, Ph-S-1H).

Compound C-55: m.p. 174-176° C. δ(CDCl₃): 2.19 (s, 6H, Ph-2,6-2CH₃), 2.30 (s, 3H, Ph-4-CH₃) 6.42 (br, 1H, NH), 6.76 (s, 2H, Ph-3,5-2H).

Compound C-56: m.p. 194-196° C. δ(CDCl₃): 2.56 (s, 3H, Ph-2-CH₃), 3.62 (s, 3H, NHCH₃), 6.44 (br, 1H, NH), 7.57 (s, 1H, Ph-3-1H), 8.06 (s, 1H, Ph-5-1H).

Compound C-58: yellow oil. δ(CDCl₃): 2.91 (s, 3H, NCH₃), 7.77 (d, J=2.4 Hz, 1H, Ph-3-1H), 7.86 (d, J=2.4 Hz, 1H, Ph-5-1H), 11.12 (br, 1H, NH).

Compound C-59: yellow oil. δ(CDCl₃): 3.96 (s, 3H, OCH₃), 7.60 (d, J=2.7 Hz, 1H, Ph-3-1H), 7.98 (d, J=2.7 Hz, 1H, Ph-5-1H), 9.15 (br, 1H, NH).

Compound C-60: m.p. 236-238° C. δ(DMCO): 2.50 (s, 3H, Ph-2-CH₃), 8.67 (s, 1H, Ph-5-1H), 9.11 (br, 1H, NH).

Compound C-62: m.p. 126-128° C. δ(CDCl₃): 3.92 (s, 1H, OMe), 6.57 (s, 1H, NH), 6.83 (d, J=9.0 Hz, 1H, Ph-6-1H), 7.47 (d, J=9.0 Hz, 1H, Ph-5-1H), 7.72 (s, 1H, Ph-3-1H).

Compound C-63: m.p. 272-274° C. δ(DMSO): 2.25 (s, 3H, Ph-2-CH₃), 6.47-6.50 (m, 1H, Ph-6-1H), 6.60-6.63 (m, 1H, Ph-5-1H), 6.84-6.91 (m, 2H, Ph-3,4-2H), 7.91 (br, 1H, NH).

Compound C-64: m.p. 193-195° C. δ(CDCl₃): 6.52 (d, J=7.5 Hz, 1H, Ph-6-1H), 7.15 (t, 1H, Ph-5-1H), 7.53 (t, 1H, Ph-4-1H), 8.27 (d, J=8.1 Hz, 1H, Ph-3-1H), 9.33 (br, 1H, NH).

Compound C-65: yellow oil. δ(CDCl₃): 2.38 (s, 3H, Ph-3-CH₃), 6.88 (br, 1H, NH), 6.92-7.18 (m, 4H, Ph-2,3,4,6-4H).

Compound C-66: m.p. 114-116° C. δ(CDCl₃): 6.75 (d, J=8.1 Hz, 1H, Ph-6-1H), 6.68 (s, 1H, Ph-2-1H), 7.04-7.12 (m, 2H, Ph-4,5-2H), 10.03 (br, 1H, NH).

Compound C-67: m.p. 96-98° C. δ(DMSO): 7.58-7.65 (m, 2H, Ph-5,6-2H), 7.96-8.02 (m, 2H, Ph-2,4-2H), 10.08 (br, 1H, NH).

Compound C-68: m.p. 140-142° C. δ(CDCl₃): 3.83 (s, 3H, OCH₃), 6.16 (br, 1H, NH), 6.91 (d, J=8.7 Hz, 2H, Ph-3,5-2H), 7.09 (d, J=8.7 Hz, 2H, Ph-2,6-2H).

Compound C-69: m.p. 160-162° C. δ(DMSO): 1.32 (9H, t-Bu), 6.18 (br, 1H, NH), 6.98 (d, J=7.8 Hz, 2H, Ph-3,5-2H), 7.38 (d, J=7.8 Hz, 2H, Ph-2,6-2H).

Compound C-70: m.p. 196-198° C. δ(CDCl₃): 6.38 (s, 1H, NH), 6.95 (dd, 2H, Ph-2,6-1H), 8.26 (d, 2H, Ph-3,5-2H).

Compound C-71: m.p. 192-194° C. δ(CDCl₃): 6.57 (br, 1H, NH), 6.63 (d, J=8.7 Hz, 1H, Ph-6-H), 7.23 (dd, J=8.7 Hz, J=2.4 Hz, 1H, Ph-5-H), 7.46 (d, J=2.4 Hz, 1H, Ph-3-H).

Compound C-72: δ(CDCl₃): 6.51 (s, 1H, NH), 7.33 (t, 1H, Ph-4-H, J=7.2 Hz), 7.47 (d, 2H, Ph-3,5-2H, J=7.2 Hz).

Compound C-73: m.p. 104-106° C. δ(CDCl₃): 6.90 (br, 1H, NH), 7.03 (m, 2H, Ph-3,5-2H), 7.25 (m, 1H, Ph-4-1H).

Compound C-74: m.p. 123-131° C. δ(CDCl₃): 6.22 (br, 1H, NH), 6.84 (d, J=2.1 Hz, 1H, Ph-6-1H), 7.09 (dd, J=8.4 Hz, J=2.1 Hz, 1H, Ph-4-1H), 7.39 (d, J=8.4 Hz, 1H, Ph-3-1H).

Compound C-75: yellow oil. δ(DMSO): 6.48 (dd, J=8.7 Hz, J=3.0 Hz, 1H, Ph-4-1H), 6.69 (d, J=3.0 Hz, 1H, Ph-6-1H), 7.08 (d, J=8.7 Hz, 1H, Ph-3-1H), 8.11 (br, 1H, NH).

Compound C-76: m.p. 199-201° C. δ(DMSO): 6.41 6.97 (s, 1H, Ph-4-1H), 6.48 (d, J=1.5 Hz, 2H, Ph-2,6-2H), 7.48 (br, 1H, NH).

Compound C-77: m.p. 132-134° C. δ(CDCl₃): 6.36 (br, 1H, NH), 6.68 (d, J=8.1 Hz, 1H, Ph-6-1H), 6.96 (t, 1H, Ph-5-1H), 7.20 (d, J=8.4 Hz, 1H, Ph-4-1H).

Compound C-78: reddish brown oil. δ(DMCO): 6.76 (d, J=8.7 Hz, 1H, Ph-6-H), 7.37 (d, J=8.7 Hz, 1H, Ph-5-1H), 7.90 (s, 1H, Ph-3-1H), 7.92 (br, 1H, NH).

Compound C-79: δ(CDCl₃): 6.37 (br, 1H, NH), 6.82 (t, 1H, Ph-6-1H), 8.06-8.15 (m, 2H, Ph-3,5-2H).

Compound C-80: m.p. 56-58° C. δ(CDCl₃): 6.75 (d, 1H, Ph-6-1H), 6.81 (br, 1H, NH), 8.12 (d, 1H, Ph-3-1H), 8.37 (s, 1H, Ph-3-1H).

Compound C-81: m.p. 136-138° C. δ(CDCl₃): 6.38 (br, 1H, NH), 7.62 (d, 1H, Ph-6-1H), 7.65 (s, 1H, Ph-3-H), 7.95 (d, 1H, Ph-4-1H).

Compound C-82: m.p. 138-140° C. δ(CDCl₃): 6.43 (br, 1H, NH), 6.83 (d, 1H, Ph-6-1H), 7.49 (d, 1H, Ph-5-1H), 7.72 (s, 1H, Ph-3-1H).

Compound C-83: yellow oil. δ(CDCl₃): 6.34 (br, 1H, NH), 7.09 (s, 1H, Ph-6-1H), 7.36 (d, J=8.4 Hz, 1H, Ph-4-1H), 7.59 (d, J=8.4 Hz, 1H, Ph-3-1H).

Compound C-85: yellow oil. δ(CDCl₃): 2.95 (s, 3H, Ph-2-CH₃) 6.30 (br, 1H, NH), 6.58 (d, J=8.1 Hz, 1H, Ph-6-1H), 6.94-7.00 (m, 2H, Ph-3,5-2H).

Compound C-86: brown oil. δ(CDCl₃): 2.42 (s, 3H, CH₃), 5.67 (br, 1H, NH), 6.63 (d, J=8.4 Hz, 1H, Ph-6-1H), 7.99 (d, J=8.4 Hz, 1H, Ph-5-1H), 8.12 (s, 1H, Ph-3-1H).

Compound C-87: reddish brown oil. δ(CDCl₃): 2.34 (s, 3H, Ph-3-CH₃), 6.03 (br, 1H, NH), 7.12-7.35 (m, 3H, Ph-3,4,5-3H).

Compound C-88: δ(CDCl₃): 6.43 (s, 1H, NH), 8.51 (s, 2H, Ph-3,5-2H).

Compound C-89: m.p. 138-140° C. δ(CDCl₃): 6.72 (d, 1H, Ph-6-1H, J=5.4), 7.53 (dd, 1H, Ph-3-1H), 8.29 (d, 1H, Ph-3-1H), 9.26 (s, 1H, NH).

Compound C-90: m.p. 137-139° C. δ(DMCO): 3.90 (s, 3H, OCH₃), 6.58 (dd, J=8.4 Hz, J=2.1 Hz, 1H, Ph-6-1H), 6.70 (d, J=2.1 Hz, 1H, Ph-2-1H), 7.78 (d, J=8.4 Hz, 1H, Ph-5-1H), 8.72 (br, 1H, NH).

Compound C-91: m.p. 256-258° C. δ(CDCl₃): 6.62 (br, 1H, NH), 7.83 (d, J=8.1 Hz, 1H, Ph-6-1H), 7.49 (s, 1H, Ph-2-1H), 7.56 (d, J=8.1 Hz, 1H, Ph-5-1H).

Compound C-93: m.p. 90-92° C. δ(CDCl₃): 6.81 (s, 1H, NH), 8.30 (s, 2H, Ph-3,5-2H).

Compound C-96: m.p. 110-112° C. δ(CDCl₃): 6.43 (s, 1H, NH), 8.51 (s, 2H, Ph-3,5-2H).

Compound C-97: m.p. 110-112° C. δ(CDCl₃): 6.94 (s, 1H, NH), 8.48 (d, 1H, Ph-5-1H), 8.73 (d, 1H, Ph-5-1H).

Compound C-98: reddish brown oil. δ(CDCl₃): 6.26 (br, 1H, NH), 7.68 (s, 2H, Ph-3,5-2H).

Compound C-100: m.p. 124-126° C. δ(CDCl₃): 6.49 (br, 1H, NH), 7.97 (d, J=10.8 Hz, 2H, Ph-3,5-2H).

Compound C-102: m.p. 91-93° C. δ(CDCl₃): 6.56 (br, 1H, NH), 7.54 (s, 2H, Ph-3,5-2H).

Compound C-103: m.p. 150-152° C. δ(CDCl₃): 6.40 (br, 1H, NH), 7.44 (s, 2H, Ph-3,5-2H).

Compound C-104: m.p. 132-134° C. δ(CDCl₃): 6.31 (br, 1H, NH), 7.15 (d, J=8.7 Hz, 1H, Ph-6-1H), 7.66 (d, J=8.7 Hz, 1H, Ph-5-1H).

Compound C-105: δ(CDCl₃): 6.70 (br, 1H, NH), 6.94 (s, 1H, Ph-6-1H), 7.57 (s, 1H, Ph-5-H).

Compound C-106: δ(CDCl₃): 6.06 (br, 1H, NH), 7.59 (s, 2H, Ph-3,5-2H).

Compound C-107: m.p. 171-173° C. δ(DMCO): 6.62 (br, 1H, NH), 6.89 (s, 2H, Ph-3,5-2H).

Compound C-108: m.p. 76-78° C. δ(CDCl₃): 3.51 (br, 1H, NH), 7.04 (t, 1H, Py-3-1H), 7.57 (t, 1H, Ph-4-1H), 7.74 (t, 1H, Ph-6-1H)

Compound C-110: m.p. 178-180° C. δ(CDCl₃): 2.35 (s, 3H, CH₃), 3.66 (br, 1H, NH) 6.48 (s, 1H, Py-3-1H), 6.82 (d, 1H, Py-5-1H), 8.10 (d, 1H, Py-6-1H).

Compound C-111: m.p. 200-202° C. δ(CDCl₃): 2.36 (s, 3H, Py-5-CH₃), 6.65 (d, J=8.1 Hz, 1H, Py-3-H), 6.86 (br, 1H, NH), 7.46 (d, J=8.1 Hz, 1H, Py-4-H), 8.06 (s, 1H, Py-6-H).

Compound C-114: m.p. 280-281° C. δ(DMCO): 6.97 (s, 1H, NH), 7.89 (s, 1H, Py-3-1H).

Compound C-125: m.p. 120-122° C. δ(CDCl₃): 6.58 (br, 1H, NH), 8.49 (s, 2H, Py-2,6-2H).

Compound C-126: m.p. 154-156° C. δ(DMCO): 6.93 (t, 1H, Py-5-1H), 8.41 (d, J=4.8 Hz, 2H, Ph-4,6-2H), 8.96 (br, 1H, NH).

Compound C-128: m.p. 194-196° C. δ(CDCl₃): 3.81 (s, 6H, 2OCH₃), 5.66 (s, 1H, Py-5-1H), 6.96 (br, 1H, NH).

FORMULATION EXAMPLES

The active ingredient can be selected base on 100% active ingredient (Weight/Weight %).

Example 23

30% Wettable Powders

| | |
|---|---|
| Compound B-54 | 30% |
| Sodium dodecyl sulfate | 2% |
| Lignin sulfonate | 3% |
| Naphthalene sulfonic acid formaldehyde condensate | 5% |
| Precipitated calcium carbonate | Make up to 100% |

The compound and other components are fully mixed, after smashing through ultrafine pulverizer, 30% wettable powder products were obtained.

Example 24

40% Suspension Concentrate

| | |
|---|---|
| Compound B-54 | 40% |
| Glycol | 10% |
| Nonylphenols polyethylene glycol ether | 6% |
| Lignin sulfonate | 10% |
| Carboxymethyl cellulose | 1% |
| 37% of formaldehyde aqueous solution | 0.2% |
| 75% of silicone oil water emulsion | 0.8% |
| Water | Make up to 100% |

Fully mixing the compound and other components, suspension concentrate can be obtained, and then any required dilution can be obtained by diluting the above suspension concentrate with water.

Example 25

60% Water Dispersible Granules

| | |
|---|---|
| Compound B-54 | 60% |
| Naphthalene sulfonate formaldehyde condensate | 12% |
| N-methyl-N-oil acyl-bovine sodium | 8% |
| Polyvinylpyrrolidone | 2% |
| Carboxymethyl cellulose | 2% |
| Kaolin | Make up to 100% |

The compound and other components were mixed and smashed, then kneaded together with water, added to the granulation 10-100 mesh machine for granulation, finally dried and sieved (at the scope screen).

Biological Testing

The compounds of the present invention showed excellent activity against a variety of plant pathogens/diseases in agricultural field. The tests of compounds of the present invention against many kinds of plant diseases caused by fungi were carried out in vitro or in vivo. Contrastive tests were carried out compared with parts of known compounds. The results of fungicidal activity are listed in the following examples.

Example 26

Determination of the Activity In Vitro

The method is as followed: High Through Put is used in the test. The compound is dissolved in a proper solvent to become a testing solution whose concentration is designed. The solvent is selected from acetone, methanol, DMF and so on according to their dissolving capability to the sample. In a no animalcule condition, the testing solution and pathogens suspension are added into the cells of 96 cells culture board, which then should be placed in the constant temperature box. 24 hours later, pathogen germination or growth can be investigated by eyeballing, and the activity in vitro of the compound is evaluated based on germination or growth of control treatment.

The activities in vitro (inhibition rate) of parts of the compounds are as follows:

(1) The inhibition rate against rice blast:

At the dose of 25 mg/L, the inhibition rate of compounds A-9, A-14, A-15, A-16, A-17, A-19, A-27, A-29, A-39, A-42, A-43, A-44, A-45, A-46, A-50, A-61, A-79, A-85, A-87, A-90, B-13, B-15, B-16, B-18, B-22, B-28, B-29, B-30, B-35, B-37, B-38, B-39, B-40, B-41, B-42, B-49, B-50, B-51, B-52, B-53, B-54, B-55, B-57, B-58, B-59, B-62, B-67, B-68, B-69, B-73, B-74, B-75, B-92, B-95, B-109, B-111, B-15, B-116, B-122, B-123, B-124, B-125, B-128, B-128b, B-130, B-131, B-132, B-133, B-137, B-138, B-139, B-141. B-143, B-144, B-146, B-149, B-152, C-8, C-14, C-15, C-23, C-27, C-28, C-29, C-30, C-33, C-35, C-38, C-39, C-40, C-41, C-45, C-46, C-48, C-49, C-50, C-60, C-62, C-68, C-70, C-71, C-79, C-80, C-81, C-82, C-88, C-89, C-93, C-96, C-97, C-98, C-99, C-109, C-111, C-118, C-124, C-125, C-126 and so on was 100%, and that of compounds A-11, A-23, A-50, A-59, A-80, B-62a, B-62b, B-142, C-114 was 80%; that of contrast compound KC28 was 80%, that of compound STM-2 was 50%, that of compounds KC1, KC2, KC3, KC12, KC21, KC22, KC23, KC25, KC26, STM-1 was all 0;

At the dose of 8.3 mg/L, the inhibition rate of compounds A-9, A-14, A-15, A-16, A-17, A-19, A-27, A-29, A-39, A-42, A-43, A-44, A-45, A-46, A-61, A-79, A-85, A-87, B-13, B-16, B-28, B-29, B-30, B-35, B-37, B-39, B-41, B-42, B-49, B-50, B-51, B-52, B-53, B-54, B-55, B-58, B-59, B-62, B-67, B-68, B-73, B-74, B-75, B-92, B-95, B-109, B-111, B-115, B-116, B-122, B-125, B-128, B-128b, B-131, B-132, B-133, B-137, B-138, B-139, B-143, B-149, C-8, C-15, C-27, C-29, C-30, C-33, C-35, C-38, C-39, C-40, C-41, C-45, C-46, C-48, C-49, C-50, C-60, C-62, C-70, C-71, C-79, C-80, C-81, C-82, C-88, C-89, C-93, C-96, C-98, C-99, C-118, C-124, C-125 and so on was 100%, and that of compounds B-69, B-141, B-144, C-14, C-68, C-126 was 80%; that of contrast compound KC28 was 50%:

At the dose of 2.8 mg/L, the inhibition rate of compounds A-9, A-14, A-15, A-16, A-17, A-19, A-29, A-42, A-43, A-44, A-45, A-46, A-61, A-85, A-87, B-13, B-16, B-28, B-29, B-30, B-35, B-37, B-39, B-41, B-42, B-49, B-50, B-51, B-52, B-53, B-55, B-58, B-59, B-62, B-67, B-68, B-73, B-74, B-75, B-92, B-95, B-109, B-111, B-115, B-116, B-125, B-128, B-128b, B-133, B-138, B-139, B-143, B-149, C-8, C-15, C-27, C-29, C-30, C-38, C-39, C-40, C-41, C-45, C-46, C-48, C-49, C-50, C-60, C-62, C-71, C-79, C-80, C-81, C-82, C-89, C-93, C-96, C-98, C-99, C-118, C-124 was 100%, and that of compounds A-27, A-39, B-54, B-122, B-137, C-35, C-70, C-88 was 80%; that of contrast compound KC28 was 0;

At the dose of 0.9 mg/L, the inhibition rate of compounds A-14, A-15, A-16, A-17, A-42, A-43, A-44, A-45, A-46, A-61, A-87, B-28, B-29, B-30, B-35, B-37, B-39, B-41, B-42, B-49, B-50, B-51, B-52, B-53, B-54, B-58, B-62, B-67, B-68, B-73, B-74, B-75, B-92, B-95, B-109, B-111, B-115, B-116, B-125, B-128, B-128b, B-133, B-139, B-149, C-8, C-15, C-27, C-30, C-39, C-40, C-41, C-45, C-46, C-49, C-50, C-89, C-93, C-96, C-98, C-99, C-118, C-124 and so on was 100%, and that of compounds A-9, A-19, A-29, C-29, C-48, C-60, C-62, C-71, C-80, C-81, C-82 was 80%; that of contrast compound KC10 was 50%, that of contrast compounds KC4, KC11 was 0;

At the dose of 0.3 mg/L, the inhibition rate of compounds A-14, A-15, A-16, A-17, A-43, A-44, A-45, A-46, A-87, B-28, B-29, B-30, B-35, B-37, B-39, B-42, B-49, B-50, B-51, B-52, B-53, B-58, B-62, B-68, B-74, B-75, B-115, B-125, B-128, B-128b, B-133, B-139, C-27, C-30, C-40, C-41, C-45, C-46, C-49, C-50, C-99, C-118, C-124 and so on was 100%, and that of compounds B-41, B-54, B-73, B-92 and so on was 80%; that of contrast compounds KC6, KC10 was 0.

(2) The inhibition rate against cucumber gray mold:

At the dose of 25 mg/L, the inhibition rate of compounds A-14, A-15, A-43, A-44, A-45, A-46, A-85, A-87, B-13, B-29, B-35, B-37, B-38, B-42, B-49, B-50, B-51, B-52, B-53, B-54, B-55, B-57, B-58, B-59, B-62b, B-67, B-68, B-73, B-74, B-75, B-92, B-95, B-109, B-111, B-115, B-116, B-122, B-128, B-128b, B-133, B-139, C-23, C-27, C-28, C-30, C-40, C-41, C-45, C-46, C-50, C-71, C-89, C-96, C-97, C-98, C-125 and so on was 100%, and that of compounds A-42, A-61, B-15, B-28, B-40, B-62, B-125, C-48, C-49, C-80, C-82, C-88, C-99 was 80%; that of contrast compound KC28 was 80%, that of contrast compound KC-20 was 50%, that of contrast compounds KC1, KC2, KC3, KC5, KC6, KC13, KC14, KC15, KC19, KC-21, KC-22, KC23, KC24, KC25, KC26, KC27, STM-1, STM-2 was 0;

At the dose of 8.3 mg/L, the inhibition rate of compounds A-14, A-15, A-43, A-44, A-45, A-46, B-35, B-37, B-42, B-49, B-50, B-51, B-52, B-53, B-54, B-55, B-57, B-58, B-68, B-74, B-75, B-92, B-95, B-109, B-115, B-116, B-122, B-128, B-128b, B-133, B-139, C-27, C-30, C-40, C-41, C-45, C-46, C-50, C-71, C-89, C-96 and so on was 100%, and that of compounds A-87, B-29, C-98 was 80%; that of contrast compounds KC7, KC8, KC28 was 0;

At the dose of 2.8 mg/L, the inhibition rate of compounds A-14, A-15, A-43, A-44, A-45, A-46, B-35, B-37, B-42, B-49, B-50, B-52, B-53, B-54, B-57, B-58, B-68, B-74, B-75, B-95, B-109, B-115, B-133, B-139, C-27, C-40, C-45, C-46, C-71, C-96 and so on was 100%, and that of compounds A-87, B-29, B-51, B-55, B-92, B-128, B-128b, C-30, C-41, C-50, C-89, C-98 was 80%; that of contrast compound KC4 was 50%, that of contrast compounds KC9, KC 10 KC11, KC12 was 0;

At the dose of 0.9 mg/L, the inhibition rate of compounds A-14, A-15, A-43, A-44, A-46, B-35, B-37, B-49, B-53, B-54, B-58, B-75, B-15, B-133, B-139, C-40, C-45, C-46, C-96 and so on was 100%, and that of compounds B-68, C-27, C-71 was 80%; that of contrast compound KC4 was 0;

At the dose of 0.3 mg/L, the inhibition rate of compounds A-14, A-15, A-43, A-46, B-35, B-49, B-53, B-133, C-45, C-46 and so on was 100%, and that of compounds B-54, B-58, B-75 was 80%.

Example 27

The Determination of Protectant Activity In Vivo

The method is as followed: The whole plant is used in this test. The compound is dissolved in a proper solvent to get mother solution. The proper solvent is selected from acetone, methanol, DMF and so on according to their dissolving capability to the sample. The volume rate of solvent and testing solution (v/v) is equal to or less than 5%. The mother solution is diluted with water containing 0.1% tween-80 to get the testing solution whose concentration is designed. The testing solution is sprayed to the host plant by a special plant sprayer. The plant is inoculated with fungus after 24 hours. According to the infecting characteristic of fungus, the plant is stored in a humidity chamber and then transferred into greenhouse after infection is finished. And the other plants are placed in greenhouse directly. The activity of compound is obtained by eyeballing after 7 days in common.

The protectant activities in vivo of parts of the compounds are as follows:

(1) The protectant activity against cucumber downy mildew in vivo:

At the dose of 400 mg/L, the protectant activity of compounds A-11, A-14, A-15, A-16, A-17, A-19, A-23, A-27, A-41, A-44, A-45, A-59, A-61, A-79, A-80, A-81, A-85, B-10, B-12, B-13, B-14, B-16, B-22, B-23, B-28, B-29, B-35, B-37, B-38, B-39, B-40, B-49, B-53, B-54, B-57, B-58, B-62b, B-67, B-68, B-69, B-73, B-74, B-92, B-95, B-109, B-111, B-115, B-116, B-125, B-128, B-128b, B-139, B-149, C-12, C-13, C-27, C-28, C-30, C-32, C-33, C-35, C-38, C-40, C-51, C-56, C-70, C-79, C-81, C-82, C-93, C-97, C-118, C-124, C-126 was 100%, and that of compounds A-8, A-21, A-90, B-15, B-26, B-42, B-63, B-133, B-137, B-138, B-146, C-8, C-39, C-60, C-88, C-96 was more than 90%, that of compounds A-50, B-9, B-62a, B-132, B-137, B-141, C-9, C-62, C-69, C-108, C-114 was no less than 80%, that of contrast compounds KC1, KC2, KC3, KC8, KC13, KC17, KC20, KC22, KC24, KC25, KC27, STM-1 was 0;

At the dose of 100 mg/L, the protectant activity of compounds A-14, A-15, A-44, A-45, A-79, A-80, B-28, B-29, B-35, B-40, B-49, B-53, B-54, B-57, B-58, B-68, B-73, B-74, B-92, B-109, B-111, B-125, B-128, B-128b, B-133, B-139, C-27, C-38, C-40, C-124 was 100%, and that of compounds A-11, A-16, A-17, A-27, A-41, A-61, B-37, B-95, B-115, B-138, C-60, C-81, C-82, C-88, C-93, C-96, C-97 was more than 95%, that of compounds B-42, C-30, C-38 was 90%, that of compounds A-19, B-137, C-70, C-79 was no less than 80%, that of contrast compounds KC7, KC12, KC15, KC16 was 20%, KC14 was 0;

At the dose of 50 mg/L, the protectant activity of compounds A-14, A-15, A-45, B-29, B-40, B-49, B-54, B-57, B-58, B-73, B-109, B-133, C-27, C-40, C-124 was 100%, and that of compounds A-79, B-28, B-35, B-53, B-74, B-92, B-111, B-125, B-128, B-139, C-88, C-96 was 98%, and that of compounds A-44, A-61, A-79, B-128b was more than 95%, that of compounds A-16, A-17, A-21, A-27, A-41, B-37, B-95, B-115 was more than 80%, that of contrast compound KC9 was 30%, KC5 was 20%, KC7, KC10, KC15 was 10%, KC11, KC16 was 0;

At the dose of 25 mg/L, the protectant activity of compounds A-14, A-45, B-29, B-57, B-133, C-27, C-40 was 100%, and that of compounds A-15, A-44, A-79, B-35, B-40, B-49, B-53, B-58, B-109, B-125, B-128, B-139, C-124 was no less than 90%, and that of compounds B-92, B-111, B-115 was no less than 80%, that of contrast compound KC9 was 20%, STM-2 was 10%, KC4, KC5, KC7, KC10, KC11, KC15 was 0;

At the dose of 12.5 mg/L, the protectant activity of compounds B-35, B-58, B-139 was 98%, and that of compounds A-14, B-133, C-124 was no less than 90%;

At the dose of 6.25 mg/L, the protectant activity of compounds B-35, B-58, B-139 was no less than 85%, and that of compounds B-133 was 80%.

(2) The protectant activity against corn rust in vivo:

At the dose of 400 mg/L, the protectant activity of compounds A-15, A-43, A-46, A-59, B-1, B-14, B-38, B-50, B-52, B-54, B-55, B-57, B-58, B-62, B-69, B-70, B-73, B-74, B-75, B-92, B-111, B-128b, B-149, C-33, C-39, C-41, C-49, C-50, C-98, C-99, C-114, C-125 was 100%, and that of compounds A-42, A-44, A-87, B-15, B-41, B-132, B-144, B-146, C-40, C-97 was no less than 95%, that of compounds B-130, B-132, B-144, C-30 was no less than 90%, that of compounds A-19, A-23, A-85, C-29, C-46, C-89 was 80%, that of contrast compounds KC1, KC2, KC3, KC4, KC5, KC6, KC8, KC12, KC13, KC14, KC15, KC16, KC17, KC18, KC19, KC20, KC22, KC24, KC25, KC26, KC27, STM-1 was 0;

At the dose of 100 mg/L, the protectant activity of compounds A-87, B-50, B-52, B-55, B-73, B-75, B-92, C-40, C-41 was 100%, and that of compounds A-43, A-46, B-69, B-146, B-149, C-49, C-97 was no less than 90%, that of compounds A-15, A-42, B-54, B-57, B-74 was no less than 80%;

At the dose of 25 mg/L, the protectant activity of compounds B-50, B-52 was no less than 98%, and that of compounds C-41 was 90%, that of compounds A-46, A-87, B-54, B-57, B-75, C-40, C-49 was no less than 80%;

At the dose of 6.25 mg/L, the protectant activity of compounds A-46, B-50, B-52, B-75 was no less than 70%.

(3) The protectant activity against wheat powdery mildew in vivo:

At the dose of 400 mg/L, the protectant activity of compounds B-50, B-52, C-50, C-82, C-91, C-98 was 100%, and that of compound A-42 was 98%, that of compound B-128b was 80%, that of contrast compounds KC1, KC2, KC3, KC4, KC5, KC6, KC7, KC8, KC12, KC13, KC15, KC20, KC21, KC22, STM-1, STM-2 was 0, KC14 was 30%;

At the dose of 100 mg/L, the protectant activity of compounds B-52, C-50 was more than 98%, and that of compound C-91 was 95%, that of compounds A-42, C-98 was 80%, that of contrast compound KC14 was 0;

At the dose of 25 mg/L, the protectant activity of compounds A-42, C-50, C-91 was no less than 75%;

At the dose of 6.25 mg/L, the protectant activity of compound C-91 was 70%.

Example 28

The Contrastive Tests Results of Parts of Compounds and Contrasts

Contrastive tests were carried out between parts of compounds, contrasts and intermediates. The test results are listed in table 21-table 24 ("/" in the following tables means no test).

TABLE 21

The inhibition rate against rice blast

| Compound No. | 0.3 mg/L | 0.1 mg/L | 0.03 mg/L |
|---|---|---|---|
| A-43 | 100 | 100 | 100 |
| A-46 | 100 | 100 | 100 |
| A-87 | 100 | 100 | 100 |
| B-28 | 100 | 100 | 80 |
| B-29 | 100 | 50 | 0 |
| B-30 | 100 | 50 | 0 |
| B-35 | 100 | 80 | 50 |
| B-39 | 100 | 80 | 0 |
| B-41 | 80 | 0 | 0 |
| B-42 | 100 | 80 | 50 |
| B-49 | 100 | 100 | 100 |
| B-50 | 100 | 50 | 0 |
| B-51 | 100 | 50 | 0 |
| B-52 | 100 | 100 | 100 |
| B-53 | 100 | 100 | 100 |
| B-54 | 100 | 0 | 0 |
| B-58 | 100 | 50 | 0 |
| B-62 | 100 | 80 | 0 |
| B-73 | 80 | 0 | 0 |
| B-74 | 100 | 50 | 0 |
| B-75 | 100 | 80 | 0 |
| B-128 | 100 | 100 | 100 |
| B-128b | 100 | 80 | 80 |
| B-133 | 100 | 100 | 100 |
| C-45 | 100 | 100 | 100 |
| C-46 | 100 | 100 | 100 |
| C-49 | 100 | 100 | 100 |
| C-50 | 100 | 100 | 100 |
| C-118 | 100 | 100 | 100 |
| C-124 | 100 | 100 | 100 |
| KC1 | 0 | 0 | 0 |
| KC2 | 0 | 0 | 0 |
| KC3 | 0 | 0 | 0 |
| KC4 | 0 | 0 | 0 |
| KC5 | 0 | 0 | 0 |
| KC6 | 0 | 0 | 0 |
| KC7 | 0 | 0 | 0 |
| KC8 | 0 | 0 | 0 |
| KC10 | 0 | 0 | 0 |
| KC11 | 0 | 0 | 0 |
| KC12 | 0 | 0 | 0 |
| KC14 | 0 | 0 | 0 |
| KC15 | 0 | 0 | 0 |
| KC21 | 0 | 0 | 0 |
| KC22 | 0 | 0 | 0 |
| KC23 | 0 | 0 | 0 |
| KC25 | 0 | 0 | 0 |
| KC26 | 0 | 0 | 0 |
| KC28 | 0 | 0 | 0 |
| STM-1 | 0 | 0 | 0 |
| STM-2 | 50 | / | / |
| chlorothalonil | 100 | 30 | 0 |
| fluazinam | 100 | 80 | 50 |

TABLE 22

The inhibition rate against cucumber gray mold

| Compound No. | 8.3 mg/L | 2.8 mg/L | 0.9 mg/L | 0.3 mg/L |
|---|---|---|---|---|
| A-15 | 100 | 100 | 100 | 100 |
| A-43 | 100 | 100 | 100 | 100 |
| B-29 | 80 | 80 | 50 | / |
| B-35 | 100 | 100 | 100 | 100 |
| B-42 | 100 | 100 | 80 | 50 |
| B-49 | 100 | 100 | 100 | 50 |
| B-50 | 100 | 100 | 100 | 0 |
| B-51 | 100 | 80 | 80 | / |
| B-52 | 100 | 100 | 100 | 0 |

TABLE 22-continued

The inhibition rate against cucumber gray mold

| Compound No. | 8.3 mg/L | 2.8 mg/L | 0.9 mg/L | 0.3 mg/L |
|---|---|---|---|---|
| B-53 | 100 | 100 | 100 | 0 |
| B-54 | 100 | 100 | 100 | 100 |
| B-57 | 100 | 100 | 80 | / |
| B-58 | 100 | 100 | 100 | 80 |
| B-74 | 100 | 100 | 80 | / |
| B-75 | 100 | 100 | 100 | 80 |
| C-45 | 100 | 100 | 100 | 100 |
| C-46 | 100 | 100 | 100 | 100 |
| KC1 | 0 | 0 | 0 | 0 |
| KC2 | 0 | 0 | 0 | 0 |
| KC3 | 0 | 0 | 0 | 0 |
| KC4 | 100 | 50 | 0 | 0 |
| KC5 | / | / | 0 | 0 |
| KC6 | / | / | 0 | 0 |
| KC7 | 0 | 0 | 0 | 0 |
| KC8 | 0 | 0 | 0 | 0 |
| KC9 | 80 | 0 | 0 | 0 |
| KC10 | 80 | 0 | 0 | 0 |
| KC11 | 50 | 0 | 0 | 0 |
| KC12 | 80 | 0 | 0 | 0 |
| KC13 | 0 | 0 | 0 | 0 |
| KC14 | 0 | 0 | 0 | 0 |
| KC15 | 0 | 0 | 0 | 0 |
| KC19 | 0 | 0 | 0 | 0 |
| KC20 | 0 | 0 | 0 | 0 |
| KC21 | 0 | 0 | 0 | 0 |
| KC22 | 0 | 0 | 0 | 0 |
| KC23 | 0 | 0 | 0 | 0 |
| KC24 | 0 | 0 | 0 | 0 |
| KC25 | 0 | 0 | 0 | 0 |
| KC26 | 0 | 0 | 0 | 0 |
| KC27 | 0 | 0 | 0 | 0 |
| KC28 | 0 | 0 | 0 | 0 |
| STM-1 | 0 | 0 | 0 | 0 |
| STM-2 | 0 | 0 | 0 | 0 |
| 百菌清 chlorothalonil | 100 | 100 | 100 | 80 |

TABLE 23

The protectant activity against corn rust

| Compound No. | 400 mg/L | 100 mg/L | 25 mg/L | 6.25 mg/L |
|---|---|---|---|---|
| A-46 | 100 | 95 | 85 | 75 |
| A-87 | 100 | 100 | 80 | 50 |
| B-49 | 100 | 95 | 30 | 0 |
| B-50 | 100 | 100 | 100 | 80 |
| B-52 | 100 | 100 | 98 | 70 |
| B-53 | 100 | 80 | 50 | 30 |
| B-54 | 100 | 90 | 80 | 65 |
| B-55 | 100 | 100 | 25 | 0 |
| B-57 | 100 | 85 | 80 | 60 |
| B-62 | 100 | 60 | 30 | 0 |
| B-73 | 98 | 100 | 70 | 30 |
| B-74 | 100 | 95 | 70 | 40 |
| B-75 | 100 | 100 | 90 | 75 |
| C-40 | 100 | 100 | 80 | 30 |
| C-41 | 100 | 100 | 90 | 50 |
| C-49 | 100 | 90 | 80 | 50 |
| KC1 | 0 | 0 | 0 | 0 |
| KC2 | 0 | 0 | 0 | 0 |
| KC3 | 0 | 0 | 0 | 0 |
| KC4 | 0 | 0 | 0 | 0 |
| KC5 | / | / | 0 | 0 |
| KC6 | 0 | 0 | 0 | 0 |
| KC8 | 0 | 0 | 0 | 0 |
| KC12 | 0 | 0 | 0 | 0 |
| KC13 | 0 | 0 | 0 | 0 |

TABLE 23-continued

The protectant activity against corn rust

| Compound No. | 400 mg/L | 100 mg/L | 25 mg/L | 6.25 mg/L |
|---|---|---|---|---|
| KC14 | 0 | 0 | 0 | 0 |
| KC15 | 0 | 0 | 0 | 0 |
| KC16 | 0 | 0 | 0 | 0 |
| KC17 | 0 | 0 | 0 | 0 |
| KC18 | 0 | 0 | 0 | 0 |
| KC19 | 0 | 0 | 0 | 0 |
| KC29 | 0 | 0 | 0 | 0 |
| KC21 | 80 | / | / | / |
| KC22 | 0 | 0 | 0 | |
| KC24 | 0 | 0 | 0 | 0 |
| KC25 | 0 | 0 | 0 | 0 |
| KC26 | 0 | 0 | 0 | 0 |
| KC27 | 0 | 0 | 0 | 0 |
| STM-1 | 0 | 0 | 0 | 0 |
| STM-2 | 70 | / | / | / |
| chlorothalonil | 50 | / | / | / |

TABLE 24

The protectant activity against cucumber downy mildew

| Compound No | 100 mg/L | 50 mg/L | 25 mg/L | 12.5 mg/L |
|---|---|---|---|---|
| B-28 | 100 | 98 | 80 | 20 |
| B-29 | 100 | 100 | 100 | 30 |
| B-35 | 100 | 98 | 98 | 98 |
| B-40 | 100 | 100 | 98 | 30 |
| B-42 | 95 | 75 | 15 | / |
| B-54 | 100 | 100 | 75 | / |
| B-57 | 100 | 100 | 100 | 30 |
| B-58 | 100 | 100 | 98 | 98 |
| B-73 | 100 | 100 | 50 | / |
| B-74 | 100 | 98 | 80 | / |
| B-133 | 100 | 100 | 100 | 95 |
| B-139 | 100 | 98 | 98 | 100 |
| KC1 | 0 | 0 | 0 | 0 |
| KC2 | 0 | 0 | 0 | 0 |
| KC3 | 0 | 0 | 0 | 0 |
| KC5 | / | / | 0 | 0 |
| KC7 | 20 | 10 | 0 | 0 |
| KC8 | 0 | 0 | 0 | 0 |
| KC9 | 65 | 30 | 20 | / |
| KC10 | 20 | 10 | 0 | 0 |
| KC11 | 0 | 0 | 0 | 0 |
| KC12 | 0 | 0 | 0 | 0 |
| KC13 | 0 | 0 | 0 | 0 |
| KC14 | 0 | 0 | 0 | 0 |
| KC15 | 20 | 10 | 0 | 0 |
| KC16 | 20 | 0 | 0 | 0 |
| KC17 | 0 | 0 | 0 | 0 |
| KC20 | 0 | 0 | 0 | 0 |
| KC21 | 70 | / | / | / |
| KC22 | 0 | 0 | 0 | 0 |
| KC24 | 0 | 0 | 0 | 0 |
| KC25 | 0 | 0 | 0 | 0 |
| KC27 | 0 | 0 | 0 | 0 |
| STM-1 | 0 | 0 | 0 | / |
| chlorothalonil | 100 | 80 | 30 | / |

Compounds for controls, from KC1 to KC28 were synthesized by inventors themselves (The structures of KC1 and KC20 are listed in the technical section of background, and the structures from KC21 to KC28 are listed as follows). Among them, compounds KC21 and KC22 are new structures which have not been reported be fore; STM-1 and STM-2 are intermediates as starting materials (purchased); Compounds from KC23 to KC25 have been reported in CN101391981. The structure of compound KC26 has been disclosed in JP11292835A and JP10182995A without any bioactivity. The structure of compound KC27 has been disclosed in JP10182995A without any bioactivity. The structure of compound KC28 has been disclosed in U.S. Pat. No. 3,965,109 with fungicidal and herbicidal activity.

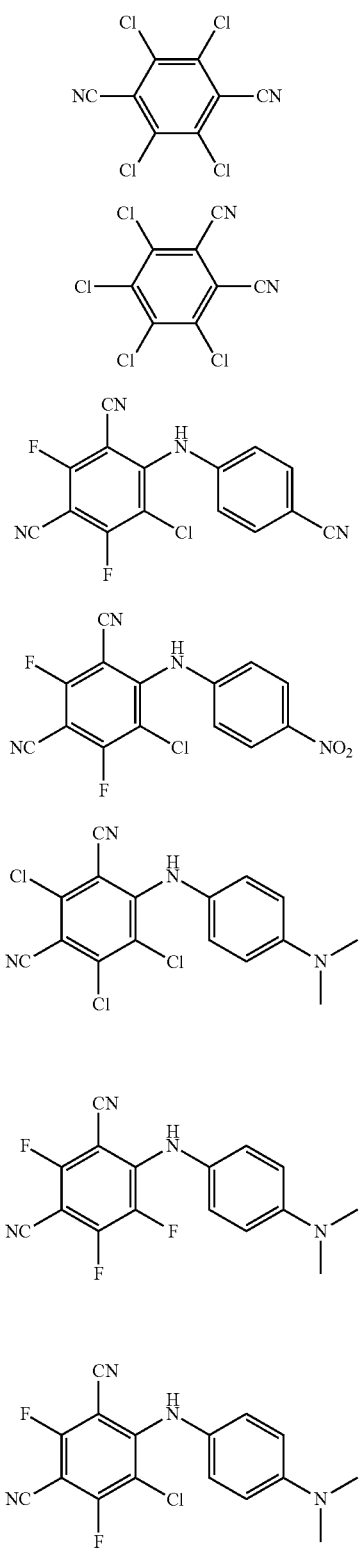

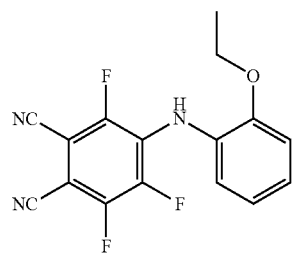

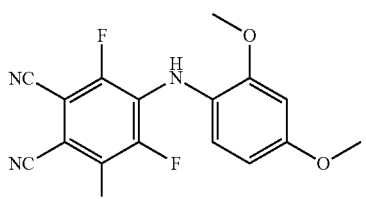

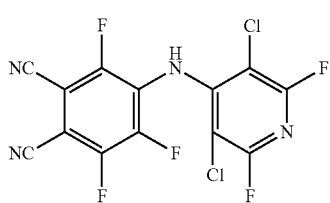

We claim:

1. A kind of substituted cyanoaniline compounds having general formula I:

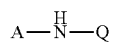

wherein:

A is selected from $A_1$, $A_2$ or $A_3$

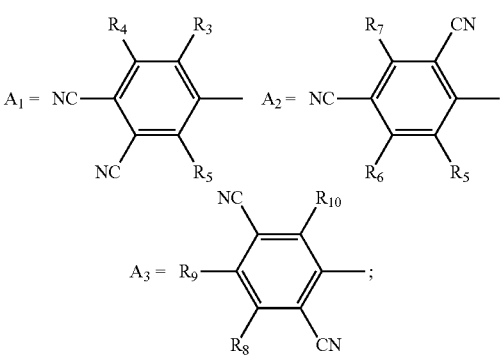

when A is $A_1$, wherein $R_2$, $R_3$ and $R_4$ are Cl;

Q is phenyl, which is mutually independently optionally substituted by $(R_{11})n$, $R_{11}$ is selected from halo, $NO_2$, CN, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl or C(=O)NHCH$_3$; n=2-4; the structure is represented by general formula I-1:

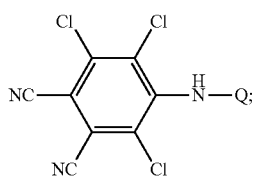

I-1 or, in general formula I when A is $A_2$, wherein $R_5$, $R_6$ and $R_7$ are same, selected from F or Cl;

Q is selected from phenyl, pyridin-2-yl, pyridin-3-yl, pyridin-4-yl, pyrimidin-2-yl, pyrazin-2-yl or pyridazin-3-yl, which is mutually independently optionally substituted by $(R_{11})n$, $R_{11}$ is selected from halo, $NO_2$, CN, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl, $C(=O)NHCH_3$, phenylaminocarbonyl, 4-Clphenylaminocarbonyl, $CO_2H$ or $CO_2Na$; n=0-5; but when Q is phenyl, n≠0 or 1; at the same time, the following compounds are excluded:

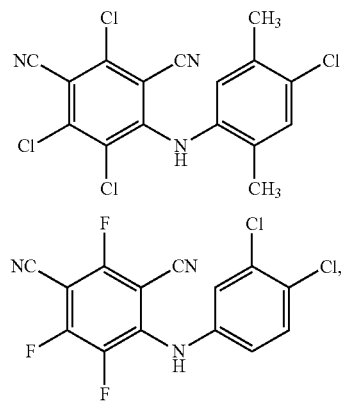

the structure is represented by general formula I-2:

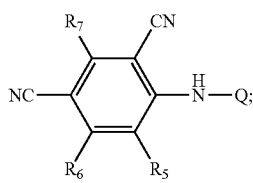

I-2 or, in general formula I when A is $A_3$, wherein $R_8$, $R_9$ and $R_{10}$ are same, selected from F or Cl;

Q is selected from phenyl, pyridin-2-yl, pyridin-3-yl, pyridin-4-yl or pyrimidin-2-yl, which is mutually independently optionally substituted by $(R_{11})n$, $R_{11}$ is selected from halo, $NO_2$, CN, $C_1$-$C_4$alkyl, $C_1$-$C_4$haloalkyl, $C_1$-$C_4$alkoxy, $C_1$-$C_4$ haloalkoxy, $C_1$-$C_4$alkoxycarbonyl or $C(=O)NHCH_3$; n=2-4; the structure is represented by general formula I-3:

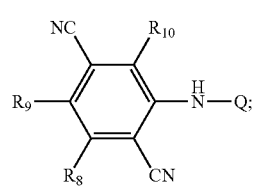

I-3 or the salts formed from the compounds of general formula I-1, I-2 or I-3 with hydrochloric acid, sulfuric acid, phosphoric acid, trifluoroacetic acid, methylsulfonic acid, acetic acid, p-toluenesulfonic acid, sodium or potassium.

2. The compounds according to the claim 1, wherein general formula I-1:

Q is selected from phenyl, which is mutually independently optionally substituted by $(R_{11})n$, $R_{11}$ is selected from F, Cl, Br, $NO_2$, CN, methyl, isopropyl, tert-butyl, trifluoromethyl, methoxyl, trifluoromethoxyl, methoxycarbonyl or $C(=O)NHCH_3$; n=2-4;

or the salts formed from the compounds of general formula I-1 with hydrochloric acid, sulfuric acid, phosphoric acid, trifluoroacetic acid, methylsulfonic acid, acetic acid, p-toluenesulfonic acid, sodium or potassium.

3. The compounds according to the claim 1, wherein general formula I-2:

$R_5$, $R_6$ and $R_7$ are same, selected from F or Cl;

Q is selected from phenyl, pyridin-2-yl, pyridin-3-yl, pyridin-4-yl, pyrimidin-2-yl, pyrazin-2-yl or pyridazin-3-yl, which is mutually independently optionally substituted by $(R_{11})n$, $R_{11}$ is selected from F, Cl, Br, $NO_2$, CN, methyl, ethyl, isopropyl, tert-butyl, trifluoromethyl, methoxyl, trifluoromethoxyl, methoxycarbonyl, ethoxycarbonyl, $C(=O)NHCH_3$, phenylaminocarbonyl, 4-Clphenylaminocarbonyl, $CO_2H$ or $CO_2Na$; n=0-5; but when Q is phenyl, n≠0 or 1; at the same time, the following compounds are excluded:

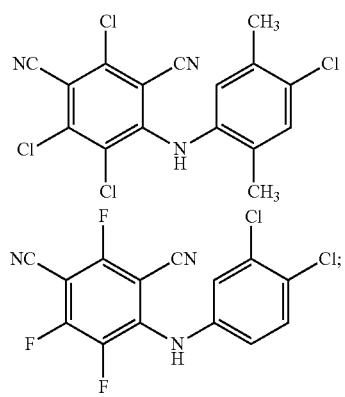

or the salts formed from the compounds of general formula I-2 with hydrochloric acid, sulfuric acid, phosphoric acid, trifluoroacetic acid, methylsulfonic acid, acetic acid, p-toluenesulfonic acid, sodium or potassium.

4. The compounds according to the claim 1, wherein general formula I-3:

$R_8$, $R_9$ and $R_{10}$ are same, selected from F or Cl;

Q is selected from phenyl, pyridin-2-yl, pyridin-3-yl, pyridin-4-yl or pyrimidin-2-yl, which is mutually independently optionally substituted by $(R_{11})n$, $R_{11}$ is selected from F, Cl, Br, $NO_2$, CN, methyl, isopropyl, trifluoromethyl, methoxyl, trifluoromethoxyl, methoxycarbonyl, ethoxycarbonyl or C(=O)NHCH$_3$; n=2-4;

or the salts formed from the compounds of general formula I-3 with hydrochloric acid, sulfuric acid, phosphoric acid, trifluoroacetic acid, methylsulfonic acid, acetic acid, p-toluenesulfonic acid, sodium or potassium.

5. The compounds according to the claim 2, wherein general formula I-1:

Q is selected from 2-F-4-NO$_2$-phenyl, 2-Cl-4-NO$_2$-phenyl, 2-Cl-5-NO$_2$-phenyl, 2-Cl-4-CF$_3$-phenyl, 2-Cl-5-CF$_3$-phenyl, 2,4-2NO$_2$-phenyl, 3-CF$_3$-4-CNphenyl, 2,4-2Clphenyl, 2-Cl-4-Brphenyl, 2-Br-4-Clphenyl, 2,6-2Clphenyl, 3-CF$_3$-4-Clphenyl, 2,3,4-3Fphenyl, 2-Br-6-CN-4-NO$_2$-phenyl, 2,6-2F-4-NO$_2$-phenyl, 2,6-2Cl-4-NO$_2$-phenyl, 2,6-2Br-4-NO$_2$-phenyl, 2-Br-6-Cl-4-NO$_2$-phenyl or 2-CH$_3$-3-Cl-4,6-2NO$_2$-phenyl;

or the salts formed from the compounds of general formula I-1 with hydrochloric acid, sulfuric acid, phosphoric acid, trifluoroacetic acid, methylsulfonic acid, acetic acid, p-toluenesulfonic acid, sodium or potassium.

6. The compounds according to the claim 3, wherein general formula I-2:

when R$_5$, R$_6$ and R$_7$ are F, Q is selected from 2-Cl-4-CF$_3$-phenyl, 2-Cl-4-NO$_2$-phenyl, 2,4-2Clphenyl, 2-Cl-4-Brphenyl, 2-Br-4-Clphenyl, 2,6-2Clphenyl, 2,6-2Br-4-NO$_2$-phenyl, 2,6-2Cl-4-NO$_2$-phenyl, 2,6-2Cl-4-CF$_3$-phenyl or 2-Br-6-CN-4-NO$_2$-phenyl;

when R$_5$, R$_6$ and R$_7$ are Cl, Q is selected from 2,6-2Fphenyl, 2-Cl-4-CF$_3$-phenyl, 2-Cl-5-CF$_3$-phenyl, 2-F-5-CF$_3$-phenyl, 2-Cl-4-NO$_2$-phenyl, 2-NO$_2$-4-Clphenyl, 2,4-2Clphenyl, 2-Cl-4-Brphenyl, 2-Br-4-Clphenyl, 2,6-2Clphenyl, 2,4,6-3Clphenyl, 2,3,4-3Fphenyl, 2,4-2NO$_2$-phenyl, 3-CF$_3$-4-CNphenyl, 2,6-2F-4-NO$_2$-phenyl, 2,4-2Cl-6-CNphenyl, 2,6-2Cl-4-CNphenyl, 2,6-2Cl-4-CF$_3$-phenyl, 2-Cl-6-F-4-NO$_2$-phenyl, 2,6-2Cl-4-NO$_2$-phenyl, 2-Br-6-Cl-4-NO$_2$-phenyl, 2-Br-6-CN-4-NO$_2$-phenyl, 2,6-2Br-4-NO$_2$-phenyl, 2,6-2Cl-4-COOCH$_3$-phenyl, 2-CH$_3$-6-Cl-4-NO$_2$-phenyl, 2-CH$_3$-4-Cl-6-NO$_2$-phenyl, 2,6-2NO$_2$-3-Cl-4-CF$_3$-phenyl, 2-CH$_3$-3-Cl-4,6-2NO$_2$-phenyl, 2,3,5-3Cl-4,6-2CNphenyl, 5-Br-pyridin-2-yl, 3-Cl-5-CF$_3$-pyridin-2-yl, 3,5,6-3Cl-pyridin-2-yl, 3,4,5,6-4Cl-pyridin-2-yl, 2-Cl-pyridin-3-yl, 6-Br-pyridin-3-yl, 2,5-2Cl-pyridin-3-yl, 2-Cl-pyridin-4-yl, 3-Br-pyridin-4-yl, 3,5-2Cl-pyridin-4-yl, pyrimidin-2-yl, 4,6-2OCH$_3$pyrimidin-2-yl, 4-CF$_3$-5-C$_2$H$_5$OCOpyrimidin-2-yl, 6-Cl-pyrazin-2-yl or 6-Cl-pyridazin-3-yl;

or the salts formed from the compounds of general formula I-2 with hydrochloric acid, sulfuric acid, phosphoric acid, trifluoroacetic acid, methylsulfonic acid, acetic acid, p-toluenesulfonic acid, sodium or potassium.

7. The compounds according to the claim 4, wherein general formula I-3:

when R$_8$, R$_9$ and R$_{10}$ are F, Q is selected from 2,4-2Clphenyl, 2-Cl-4-Brphenyl, 2-Br-4-Clphenyl, 2,6-2Clphenyl, 2-F-4-NO$_2$-phenyl, 2-Cl-4-NO$_2$-phenyl, 2-Cl-5-NO$_2$-phenyl, 2-Cl-4-CF$_3$-phenyl, 2-OCH$_3$-4-NO$_2$-phenyl, 2-NO$_2$-4-Clphenyl, 3-CF$_3$-4-Clphenyl, 2,6-2Cl-4-NO$_2$-phenyl, 2,6-2Br-4-NO$_2$-phenyl, 2,6-2Cl-4-CF$_3$-phenyl, 2-Br-6-CN-4-NO$_2$-phenyl, 2-Br-6-Cl-4-NO$_2$-phenyl or 3,5-2Cl-pyridin-4-yl;

when R$_8$, R$_9$ and R$_{10}$ are Cl, Q is selected from 2,4-2Clphenyl, 2-Cl-4-Brphenyl, 2-Br-4-Clphenyl, 2,6-2Clphenyl, 2,4-2NO$_2$-phenyl, 2-Cl-4-NO$_2$-phenyl, 2-Cl-5-NO$_2$-phenyl, 2-NO$_2$-4-Clphenyl, 2-OCH$_3$-4-NO$_2$-phenyl, 3-CF$_3$-4-Clphenyl, 2-F-4-NO$_2$-phenyl, 2-Cl-4-CF$_3$-phenyl, 2-Cl-5-CF$_3$-phenyl, 3-CF$_3$-4-CNphenyl, 2,6-2Cl-4-NO$_2$-phenyl, 2,6-2Br-4-NO$_2$-phenyl, 2,6-2F-4-NO$_2$-phenyl, 2-Cl-6-F-4-NO$_2$-phenyl, 2-Br-6-Cl-4-NO$_2$-phenyl, 2,6-2Cl-4-CF$_3$-phenyl, 2-Br-6-CN-4-NO$_2$-phenyl, 2-CH$_3$-3-Cl-4,6-2NO$_2$-phenyl, 2,5-2Cl-pyridin-3-yl, 3,5-2Cl-pyridin-4-yl or pyrimidin-2-yl;

or the salts formed from the compounds of general formula I-3 with hydrochloric acid, sulfuric acid, phosphoric acid, trifluoroacetic acid, methylsulfonic acid, acetic acid, p-toluenesulfonic acid, sodium or potassium.

8. The compounds according to the claim 5, wherein general formula I-1:

Q is selected from 2-F-4-NO$_2$-phenyl, 2-Cl-4-NO$_2$-phenyl, 2-Cl-5-NO$_2$-phenyl, 2-Cl-4-CF$_3$-phenyl, 2,4-2Clphenyl, 2-Cl-4-Brphenyl, 2-Br-4-Clphenyl, 2,6-2Clphenyl, 2-Br-6-CN-4-NO$_2$-phenyl, 2,6-2F-4-NO$_2$-phenyl, 2,6-2Cl-4-NO$_2$-phenyl, 2,6-2Br-4-NO$_2$-phenyl or 2-Br-6-Cl-4-NO$_2$-phenyl; namely, the compounds having the following structures:

or the salts formed from the compounds of general formula I-1 with hydrochloric acid, sulfuric acid, phosphoric acid, trifluoroacetic acid, methylsulfonic acid, acetic acid, p-toluenesulfonic acid, sodium or potassium.

9. The compounds according to the claim 6, wherein general formula I-2:

when R$_5$, R$_6$ and R$_7$ are F, Q is selected from 2-Cl-4-CF$_3$-phenyl, 2,4-2Clphenyl, 2-Cl-4-Brphenyl, 2-Br-4-Clphenyl, 2,6-2Clphenyl or 2,6-2Br-4-NO$_2$-phenyl;

when R$_5$, R$_6$ and R$_7$ are Cl, Q is selected from 2-Cl-4-CF$_3$-phenyl, 2-Cl-5-CF$_3$-phenyl, 2-F-5-CF$_3$-phenyl, 2-Cl-4-NO$_2$-phenyl, 2,4-2NO$_2$-phenyl, 2-NO$_2$-4-Clphenyl, 2,4-2Clphenyl, 2-Cl-4-Brphenyl, 2-Br-4-Clphenyl, 2,6-2Clphenyl, 2,3,4-3Fphenyl, 2,4,6-3Clphenyl, 2,6-2F-4-NO$_2$-phenyl, 2,4-2Cl-6-CNphenyl, 2,6-2Cl-4-CNphenyl, 2,6-2Cl-4-CF$_3$-phenyl, 2,6-2Cl-4-COOCH$_3$-phenyl, 2-Cl-6-F-4-NO$_2$-phenyl, 2,6-2Cl-4-NO$_2$-phenyl, 2-Br-6-Cl-4-NO$_2$-phenyl, 2-Br-6-CN-4-NO$_2$-phenyl, 2,6-2Br-4-NO$_2$-phenyl, 2-CH$_3$-6-Cl-4-NO$_2$-phenyl, 2-CH$_3$-3-Cl-4,6-2NO$_2$-phenyl, 2,3,5-3Cl-4,6-2CNphenyl, 3-Cl-5-CF$_3$-pyridin-2-yl, 3,5,6-3Cl-pyridin-2-yl, 3,4,5,6-4Cl-pyridin-2-yl, 2,5-2Cl-pyridin-3-yl, 3,5-2Cl-pyridin-4-yl, 6-Cl-pyrazin-2-yl or 6-Cl-pyridazin-3-yl; namely, the compounds having the following structures:

or the salts formed from the compounds of general formula I-2 with hydrochloric acid, sulfuric acid, phosphoric acid, trifluoroacetic acid, methylsulfonic acid, acetic acid, p-toluenesulfonic acid, sodium or potassium.

10. The compounds according to the claim 7, wherein general formula I-3:

when R$_8$, R$_9$ and R$_{10}$ are F, Q is selected from 2,4-2Clphenyl, 2-Cl-4-Brphenyl, 2-Br-4-Clphenyl, 2,6-2Clphenyl, 2-Br-6-CN-4-NO$_2$-phenyl or 2-Br-6-Cl-4-NO$_2$-phenyl;

when R$_8$, R$_9$ and R$_{10}$ are Cl, Q is selected from 2-F-4-NO$_2$-phenyl, 2-Cl-4-CF$_3$-phenyl, 2,4-2Clphenyl, 2-Cl-4-Brphenyl, 2-Br-4-Clphenyl, 2,6-2Clphenyl, 2,6-2Cl-4-NO$_2$-phenyl, 2,6-2Br-4-NO$_2$-phenyl, 2,6-2F-4-NO$_2$-phenyl, 2-Cl-6-F-4-NO$_2$-phenyl, 2-Br-6-Cl-4-NO$_2$-phenyl, 2,6-2Cl-4-CF$_3$-phenyl, 2,5-2Cl-pyridin-3-yl or 3,5-2Cl-pyridin-4-yl; namely, the compounds having the following structures:

or the salts formed from the compounds of general formula I-3 with hydrochloric acid, sulfuric acid, phosphoric acid, trifluoroacetic acid, methylsulfonic acid, acetic acid, p-toluenesulfonic acid, sodium or potassium.

11. A method of controlling plant pathogens and diseases which comprises applying the compound having general formula I or its salts according to claim 1 to a suspected pathogen site.

12. A composition of fungicides, comprising the compounds having general formula I as an active ingredient and acceptable carrier in agriculture, wherein the weight percentage of the active ingredient in the composition is 0.5-90%.

* * * * *